United States Patent
Charles et al.

(10) Patent No.: US 9,724,015 B2
(45) Date of Patent: *Aug. 8, 2017

(54) SYSTEMS, METHODS, COMPOSITIONS AND DEVICES FOR IN VIVO MAGNETIC RESONANCE IMAGING OF LUNGS USING PERFLUORINATED GAS MIXTURES

(71) Applicant: Duke University, Durham, NC (US)

(72) Inventors: Hal Cecil Charles, Chapel Hill, NC (US); Brian J. Soher, Chapel Hill, NC (US)

(73) Assignee: Duke University, Durham, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/987,356

(22) Filed: Jan. 4, 2016

(65) Prior Publication Data

US 2016/0113548 A1 Apr. 28, 2016

Related U.S. Application Data

(63) Continuation of application No. 13/577,926, filed as application No. PCT/US2011/025011 on Feb. 16, 2011, now Pat. No. 9,254,098.

(Continued)

(51) Int. Cl.
*A61B 5/055* (2006.01)
*A61B 5/08* (2006.01)
(Continued)

(52) U.S. Cl.
CPC ............ *A61B 5/0813* (2013.01); *A61B 5/055* (2013.01); *A61B 5/08* (2013.01); *A61B 5/082* (2013.01);
(Continued)

(58) Field of Classification Search
CPC ........ A61B 2560/0223; A61B 2576/02; A61B 5/055; A61B 5/08; A61B 5/0813; A61B 5/082; A61B 5/087; A61B 5/7285; A61M 16/0054; A61M 16/12; A61M 2016/1025; A61M 2202/0476; A61M 2230/432; A61M 2230/435; G01R 33/5601;
(Continued)

(56) References Cited

U.S. PATENT DOCUMENTS 4,725,779 A 2/1988 Hyde et al.
4,782,298 A 11/1988 Arakawa et al.
(Continued)

FOREIGN PATENT DOCUMENTS

WO WO 2007/117853 10/2007

OTHER PUBLICATIONS

Adolphi et al., Quantitative Mapping of Ventilation-Perfusion Ratios in Lungs by 19 F Imaging of T1 of Inert Fluorinated Gases, Magnetic Resonance in Medicine, 2008, pp. 739-746, vol. 59.
(Continued)

*Primary Examiner* — Ruth S Smith
(74) *Attorney, Agent, or Firm* — Myers Bigel, P.A.

(57) ABSTRACT

Systems and methods for generating MRI images of the lungs and/or airways of a subject using a medical grade gas mixture comprises between about 20-79% inert perfluorinated gas and oxygen gas. The images are generated using acquired $^{19}$F magnetic resonance image (MRI) signal data associated with the perfluorinated gas and oxygen mixture.

24 Claims, 23 Drawing Sheets

Related U.S. Application Data

(60) Provisional application No. 61/435,599, filed on Jan. 24, 2011, provisional application No. 61/305,025, filed on Feb. 16, 2010.

(51) Int. Cl.

| | |
|---|---|
| *A61B 5/00* | (2006.01) |
| *A61M 16/00* | (2006.01) |
| *A61M 16/12* | (2006.01) |
| *G01R 33/56* | (2006.01) |
| *G01R 33/563* | (2006.01) |
| *A61B 5/087* | (2006.01) |
| *G01R 33/567* | (2006.01) |
| *A61M 16/10* | (2006.01) |
| *G01R 33/50* | (2006.01) |

(52) U.S. Cl.
CPC ....... *A61B 5/7285* (2013.01); *A61M 16/0054* (2013.01); *A61M 16/12* (2013.01); *G01R 33/5601* (2013.01); *G01R 33/56325* (2013.01); *A61B 5/087* (2013.01); *A61B 2560/0223* (2013.01); *A61B 2576/02* (2013.01); *A61M 2016/1025* (2013.01); *A61M 2202/0476* (2013.01); *A61M 2230/432* (2013.01); *A61M 2230/435* (2013.01); *G01R 33/50* (2013.01); *G01R 33/5673* (2013.01); *G01R 33/56366* (2013.01)

(58) Field of Classification Search
CPC ........ G01R 33/56325; G01R 33/56366; G01R 33/5673; G01R 33/50
See application file for complete search history.

(56) References Cited

U.S. PATENT DOCUMENTS

| | | |
|---|---|---|
| 5,075,624 A | 12/1991 | Bezjak |
| 5,363,845 A | 11/1994 | Chowdhury et al. |
| 5,435,302 A | 7/1995 | Lenkinski et al. |
| 5,437,272 A | 8/1995 | Fuhrman |
| 5,646,530 A | 7/1997 | Strenk et al. |
| 5,675,254 A | 10/1997 | Fiat et al. |
| 6,076,005 A | 6/2000 | Sontag et al. |
| 6,211,677 B1 | 4/2001 | Burl et al. |
| 6,323,648 B1 | 11/2001 | Belt et al. |
| 6,414,488 B1 | 7/2002 | Chmielewski |
| 6,552,544 B2 | 4/2003 | Wong et al. |
| 6,567,686 B2 | 5/2003 | Sexton et al. |
| 6,677,755 B2 | 1/2004 | Belt et al. |
| 6,927,575 B2 | 8/2005 | Burl et al. |
| 6,940,282 B2 | 9/2005 | Dumoulin et al. |
| 7,622,928 B2 | 11/2009 | Gauss et al. |
| 8,013,609 B2 | 9/2011 | Vartiovaara |
| 8,390,287 B2 | 3/2013 | Crozier et al. |
| 2001/0037063 A1 | 11/2001 | Albert et al. |
| 2002/0043267 A1 | 4/2002 | Weller et al. |
| 2006/0264736 A1 | 11/2006 | Ehaman et al. |
| 2006/0275836 A1 | 12/2006 | Kirkpatrick et al. |
| 2008/0077038 A1 | 3/2008 | McDonough et al. |
| 2008/0132778 A1 | 6/2008 | Shankaranarayanan et al. |
| 2008/0208038 A1 | 8/2008 | Schreiber et al. |
| 2009/0160442 A1 | 6/2009 | Mazurkewitz et al. |
| 2010/0145186 A1 | 6/2010 | McGrath et al. |
| 2010/0182009 A1 | 7/2010 | Crozier et al. |
| 2010/0301862 A1 | 12/2010 | Tropp et al. |

OTHER PUBLICATIONS

Ball et al., Regional Pulmonary Function Studied with Xenon[133], Journal of Clinical Investigation, 1962, pp. 519-531, vol. 41, No. 3.

Bauman et al., Non-Contrast-Enhanced Perfusion and Ventilation Assessment of the Human Lung by Means of Fourier Decomposition in Proton MRI, Magnetic Resonance in Medicine, 2009, pp. 656-664, vol. 62.

Chon et al., Effect of low-xenon and krypton supplementation on signal/noise of regional CT-based ventilation measurements, J Appl Physiol, 2007, pp. 1535-1544, vol. 102.

Chon et al., Differences in regional wash-in and wash-out time constants for xenon-CT ventilation studies, Respiratory Physiology & Neurobiology, 2005, pp. 65-83, vol. 148.

Cleveland et al., Hyperpolarized $^{129}$Xe MR Imaging of Alveolar Gas Uptake in Humans, PLoS ONE, Aug. 2010, 8 pages, vol. 5, Issue 8, e12192.

Conradi et al., Hyperpolarized $^3$He and perfluorocarbon gas diffusion MRI of lungs, Progress in Nuclear magnetic Resonance Spectroscopy, 2006, pp. 63-83, vol. 48.

Coxson et al., New and Current Clinical Imaging Techniques to Study Chronic Obstructive Pulmonary Disease, Am J Respir Crit Care Med, 2009, pp. 588-597, vol. 180.

Crapo et al., ATS Statement: Guidelines for the Six-Minute Walk Test, Am J Respir Crit Care Med, 2002, pp. 111-117, vol. 166.

De Lange et al., Changes in Regional Airflow Obstruction over Time in the Lungs of Patients with Asthma: Evaluation with $^3$He MR Imaging, Radiology, Feb. 2009, pp. 567-575, vol. 250, No. 2.

Diaz et al., Hyperpolarized $^3$He Apparent Diffusion Coefficient MRI of the Lung: Reproducibility and Volume Dependency in Healthy Volunteers and Patients With Emphysema, Journal of Magnetic Resonance Imaging, 2008, pp. 763-770, vol. 27.

Donnelly et al., Cystic Fibrosis: Combined Hyperpolarized $^3$He-enhanced and Conventional Proton MR Imaging in the Lung—Preliminary Observations, Radiology, 1999, pp. 885-889, vol. 212, No. 3.

Driehuys et al., Chronic Obstructive Pulmonary Disease: Safety and Tolerability of Hyperpolarized $^{129}$Xe MR Imaging in Healthy Volunteers and Patients, Radiology, 2012, pp. 279-289, vol. 262, No. 1.

Driehuys et al, Pulmonary Perfusion and Xenon Gas Exchange in Rats: MR Imaging with Intravenous Injection of Hyperpolarized $^{129}$Xe[1], Radiology, 2009, pp. 386-393, vol. 252, No. 2.

Fain et al., Early Emphysematous Changes in Asymptomatic Smokers: Detection with $^3$He MR Imaging, Radiology, Jun. 2006, pp. 875-883, vol. 239, No. 3.

Fain et al., Imaging of Lung Function using Hyperpolarized Helium-3 Magnetic Resonance Imaging: review of Current and Emerging Translational Methods and Applications, J Magn Reson Imaging, Dec. 2010, pp. 1398-1408, vol. 32, No. 6.

Halaweish et al., Effect of Lung Inflation Level on Hyperpolarized 3He Apparent Diffusion Coefficient Measurements in Never-Smokers, Radiology, 2013, pp. 572-580, vol. 268, No. 2.

Halaweish et al., Physiorack: An Integrated MRI Safe/Conditional, Gas Delivery, Respiratory Gating, and Subject Monitoring Solution for Structural and Functional Assessments of Pulmonary Function, Journal of Magnetic Resonance Imaging, 2013, pp. 1-7.

Halaweish et al., Perfluoropropane gas as a Magnetic Resonance Lung Imaging Contrast Agent in Humans, CHEST Journal, 2013, pp. 1-30, vol. 144, No. 4.

He et al., Extending Semiautomatic ventilation Defect Analysis for Hyperpolarized 129Xe Ventilation MRI, Academic Radiology, 2014, pp. 1530-1541, vol. 21, No. 12.

Holmes et al., Imaging of Lung Ventilation and Respiratory Dynamics in a single Ventilation Cycle Using Hyperpolarized He-3 MRI, Journal of Magnetic Resonance Imaging, 2007, pp. 630-636, vol. 26.

Holmes et al., 3D hyperpolarized He-3 MRI of ventilation using a multi-echo projection acquisition, Magn Reson Med, May 2008, pp. 1062-1071, vol. 59, No. 5.

International Search Report & Written Opinion for corresponding PCT application No. PCT/US2011/025011, date of mailing Oct. 17, 2011.

Jacob et al., $^{19}$F MR Imaging of Ventilation and Diffusion in Excised Lungs, Magnetic Resonance in Medicine, 2005, pp. 577-585, vol. 54.

Kauczor et al., Assessment of lung ventilation by MR imaging current status and future perspectives, Eur Radiol, 2002, pp. 1962-1970, vol. 12.

(56) References Cited

OTHER PUBLICATIONS

Kauczor et al., Computed Tomographic Imaging of the Airways in COPD and Asthma, Journal of Thoracic Imaging, Nov. 2011, pp. 290-300, vol. 26, Issue 4, Abstract.

Kuethe et al., Imaging Lungs Using Inert Fluorinated Gases, MRM, 1998, pp. 85-88, vol. 39.

Kuethe et al., Imaging obstructed ventilation with NMR using inert fluorinated gases, . Appl Physiol, 2000, pp. 2279-2286, vol. 88.

Kuethe et al., Volume of Rat Lungs Measured Throughout the Respiratory Cycle Using $^{19}$F NMR of the Inert Gas $SF_6$, Magnetic Resonance in Medicine, 2002, pp. 547-549, vol. 48.

Ley-Zaporozhan et al., Imaging Phenotypes of Chronic Obstructive Pulmonary Disease, Journal of Magnetic Resonance Imaging, 2010, pp. 1340-1352, vol. 32.

MacFall et al., Human Lung Air Spaces: Potential for MR Imaging with Hyperpolarized He-3[1], Radiology, 1996, pp. 553-558, vol. 200, No. 2.

Ohno et al., Oxygen-enhanced MR Imaging: Correlation with Postsurgical Lung Function in Patients with Lung Cancer, Radiology, 2005, pp. 704-711, vol. 236, No. 2.

Parraga et al., Hyperpolarized $^3$He Magnetic Resonance Imaging of Ventilation Defects in Healthy Elderly Volunteers Initial Findings at 3.0 Tesla, Acad Radiol, Jun. 2008, pp. 776-785, vol. 15, No. 6.

Parraga et al., Hyperpolarized $^3$He Ventilation Defects and Apparent Diffusion Coefficients in Chronic Obstructive Pulmonary Disease, Investigative Radiology, Jun. 2007, pp. 384-391, vol. 42, No. 6.

Patz et al., Human Pulmonary Imaging and Spectroscopy with Hyperpolarized $^{129}$Xe at 0.2T, Acad Radiol, 2008, pp. 713-727, vol. 15, No. 6.

Perez-Sanchez et al., In Vivo diffusion Weighted $^{19}$F MRI Using $SF_6$, Magnetic Resonance in Medicine, 2005, pp. 460-463, vol. 54.

Rinck et al., NMR-Imaging of Fluorine-containing substances, RoFo, 1984, pp. 239-243, vol. 140, No. 3., Summary.

Ruiz-Cabello et al., Diffusion-weighted $^{19}$F-MRI of lung periphery: Influence of pressure and air-$SF_6$ composition on apparent diffusion coefficients, Respiratory Physiology & Neurobiology, 2005, pp. 43-56, vol. 148.

Scholz et al., Comparison of magnetic resonance imaging of inhaled $SF_6$ with respiratory gas analysis, Magnetic Resonance Imaging, 2008, 8 pages.

Schreiber et al., Dynamic $^{19}$F-MRI of Pulmonary Ventilation Using Sulfur Hexafluoride ($SF_6$) Gas, Magnetic Resonance in Medicine, 2001, pp. 605-613, vol. 45.

Schreiber et al., Breathhold $^{19}$F-Magnetic Resonance Imaging of Lung Ventilation using $SF_6$ Gas, Fortschr Rontgenstr, 2000, pp. 500-503, vol. 172.

Soher et al., Lung Imaging in Humans at 3T Using Perfluorinated Gases as MR Contrast Agents, International Society of Magnetic Resonance in Medicine, May 2010, pp. 3389, vol. 18.

Sverzellati et al., New insights on COPD imaging via CT and MRI, International Journal of COPD, 2007, pp. 301-312, vol. 2, No. 3.

Tzeng et al., The difference in ventilation heterogeneity between asthmatic and healthy subjects quantified using hyperpolarized 3He MRI, Journal of Applied Physiology, Mar. 2009, pp. 813-822, vol. 106.

Van Beek et al., Functional Imaging: CT and MRI, Clin Chest Med., Mar. 2008, 32 pages, vol. 29, No. 1.

Van Beek et al., Hyperpolarised $^3$He MRI *versus* HRCT in COPD and normal volunteers: PHIL trial, European respiratory Journal, 2009, pp. 1311-1321, vol. 34, No. 6.

Van Beek et al., Functional MRI of the Lung Using Hyperpolarized 3-Helium Gas, Journal of Magnetic Resonance Imaging, 2004, pp. 540-554, vol. 20.

Wolf et al., Subsecond Fluorine-19 MRI of the Lung, Magnetic Resonance in Medicine, 2006, pp. 948-951, vol. 55.

Woods et al., Hyperpolarized $^3$HE Diffusion MRI and Histology in Pulmonary Emphysema, Magnetic Resonance in Medicine, 2006, pp. 1293-1300, vol. 56.

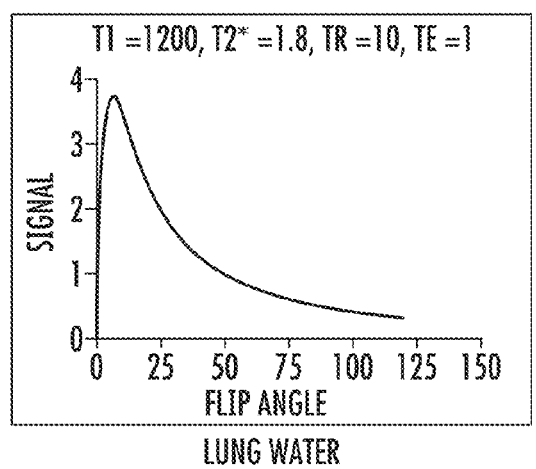
FIG. 5A  LUNG WATER
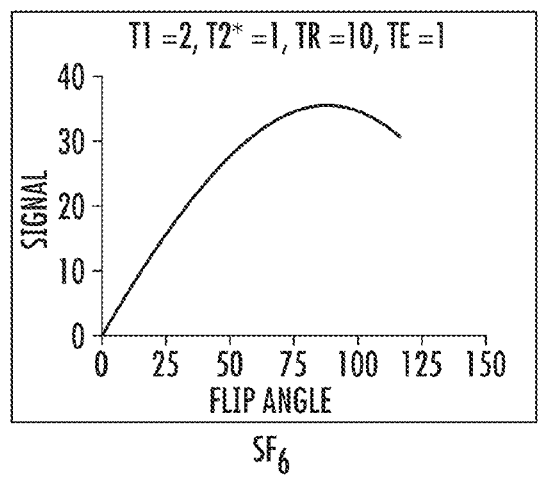
FIG. 5B  SF$_6$
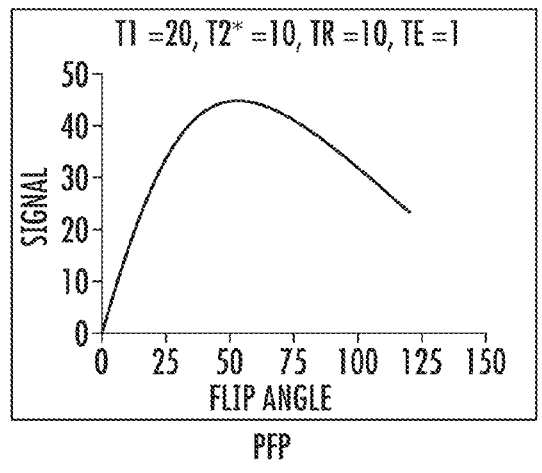
FIG. 5C  PFP

FIG. 17A (VDS=39)

| Vol.# | SLICE | NAME | AREA | AREA mm2 | PERIM | PERIM mm | MERAang1 | MERAarea | MERAasp | REF | Circ. | C/API | Cen.X | Cen.Y | WCen.X | WCen.Y | DIFX | DIFY | ASYM |
|---|---|---|---|---|---|---|---|---|---|---|---|---|---|---|---|---|---|---|---|
| | 6 | 1.OBJECT | 275 | 2685.55 | 103.57 | 323.65 | 181 | 502.86 | 0.56 | 0.55 | 39.01 | 3.1 | 41.71 | 53.84 | 41.78 | 54.28 | -0.07 | -0.44 | -0.51 |
| | 7 | 1.OBJECT | 1240 | 12109.33 | 185.61 | 580.03 | 6 | 1772.74 | 0.39 | 0.7 | 27.78 | 2.21 | 41.71 | 54.4 | 42.25 | 54.54 | -0.54 | -0.14 | -0.69 |
| | 8 | 1.OBJECT | 1794 | 17519.53 | 204.3 | 638.43 | 6 | 2486.23 | 0.4 | 0.73 | 23.28 | 1.85 | 42.34 | 58.16 | 43.65 | 56.13 | 1.31 | 2.03 | 0.72 |
| | 9 | 1.OBJECT | 2100 | 20507.81 | 217.61 | 680.03 | 9 | 2832.11 | 0.46 | 0.74 | 22.55 | 1.79 | 42.89 | 59.68 | 44.61 | 56.74 | -1.92 | 2.94 | 1.02 |
| | 10 | 1.OBJECT | 2442 | 23847.66 | 222.44 | 695.12 | 12 | 3208.71 | 0.51 | 0.76 | 20.26 | 1.61 | 43.57 | 59.84 | 44.46 | 57 | -0.89 | 2.84 | 1.95 |
| | 11 | 1.OBJECT | 2534 | 24746.09 | 222.78 | 696.19 | 9 | 3202.19 | 0.33 | 0.79 | 19.59 | 1.5 | 44.11 | 51.67 | 42.93 | 58.58 | 1.18 | 3.09 | 4.27 |
| | 12 | 1.OBJECT | 2335 | 22802.73 | 218.2 | 681.86 | 12 | 3013.94 | 0.51 | 0.77 | 20.39 | 1.62 | 43.68 | 62.76 | 41.57 | 58.62 | 2.11 | 4.14 | 6.25 |
| | 13 | 1.OBJECT | 2125 | 20751.95 | 210.54 | 657.93 | 12 | 2497.89 | 0.51 | 0.79 | 20.86 | 1.66 | 43.57 | 61.85 | 40.74 | 58.12 | 2.83 | 5.73 | 8.56 |
| | 14 | 1.OBJECT | 1978 | 19316.41 | 198.3 | 619.08 | 12 | 2462.1 | 0.53 | 0.77 | 19.88 | 1.58 | 43.8 | 59.18 | 40.9 | 52.61 | 2.9 | 6.57 | 9.47 |
| | 15 | 1.OBJECT | 1677 | 16374.95 | 178.2 | 556.86 | 15 | 2370.81 | 0.56 | 0.71 | 18.93 | 1.51 | 43.94 | 54.03 | 42.26 | 49.7 | 1.18 | 4.33 | 5.51 |
| | 16 | 1.OBJECT | 1313 | 12822.27 | 152.88 | 477.76 | 18 | 1878.17 | 0.6 | 0.77 | 17.8 | 1.42 | 44.77 | 49.54 | 45.19 | 47.46 | -0.42 | 2.08 | 1.66 |
| | 17 | 1.OBJECT | 788 | 7695.31 | 118.4 | 368.99 | 27 | 1019.54 | .73 | 0.77 | 17.79 | 1.42 | 46.22 | 45.5 | 46.56 | 44.5 | -0.34 | 1 | 0.66 |
| | 18 | 1.OBJECT | 271 | 2646.48 | 83.53 | 261.02 | 0 | 442 | 0.65 | 0.61 | 25.74 | 2.05 | 43.67 | 40.49 | 43.76 | 40.23 | -0.09 | 0.26 | 0.17 |

FIG. 17B (VDS=116)

| Vol.# | SLICE | NAME | AREA | AREA mm2 | PERIM | PERIM mm | MERAang | MERAarea | MERAasp | REF | Circ. | C/API | CEBx | Cen.Y | WCEBx | WCEBy | DIFX | DIFY | ASYM |
|---|---|---|---|---|---|---|---|---|---|---|---|---|---|---|---|---|---|---|---|
| | 5 | 1.OBJECT+3.012747 | 1706.55 | 241.89 | 735.92 | 0 | 2353.61 | 0.37 | 0.74 | 33.49 | 2.67 | 44.33 | 56.4 | 42.48 | 53.28 | 1.85 | 3.14 | 4.99 | |
| | 6 | 1.OBJECT+3.012827 | 2370.117 | 242.2 | 756.88 | 3 | 3111.67 | 0.4 | 0.79 | 24.17 | 1.92 | 43.93 | 59.14 | 40.23 | 59.84 | 3.7 | 6.3 | 10 | |
| | 7 | 1.OBJECT+3.012931 | 2862.015 | 254.68 | 785.88 | 6 | 3684.16 | 0.45 | 0.8 | 22.13 | 1.76 | 43.74 | 60.64 | 38.38 | 53.01 | 5.36 | 6.63 | 12.19 | |
| | 8 | 1.OBJECT+3.013173 | 3098.33 | 265.85 | 830.79 | 6 | 4122.08 | 0.51 | 0.77 | 22.27 | 1.77 | 44.21 | 62.79 | 37.48 | 57.14 | 6.73 | 5.65 | 12.38 | |
| | 9 | 1.OBJECT+3.013263 | 3185.525 | 271.31 | 848.47 | 3 | 4317.35 | 0.54 | 0.76 | 22.59 | 1.8 | 45.27 | 64.14 | 38.3 | 58.38 | 7.73 | 5.56 | 13.29 | |
| | 10 | 1.OBJECT+3.013272 | 3195.312 | 275.65 | 862.34 | 0 | 4550 | 0.55 | 0.72 | 22.88 | 1.85 | 45.86 | 64.76 | 38.38 | 59.59 | 7.56 | 5.17 | 12.73 | |
| | 11 | 1.OBJECT+3.013104 | 3031.25 | 266.38 | 823.36 | 6 | 4576.01 | 0.61 | 0.71 | 29.38 | 1.82 | 45.73 | 66.2 | 39.14 | 61.76 | 6.64 | 4.44 | 11.08 | |
| | 12 | 1.OBJECT+3.012564 | 2539.06 | 275.41 | 823.65 | 9 | 4264 | 0.63 | 0.6 | 22.76 | 2.25 | 43.04 | 66.04 | 38.06 | 63.5 | 4.98 | 2.54 | 7.52 | |
| | 13 | 1.OBJECT+3.012192 | 2408.25 | 223.37 | 698.22 | 6 | 3300.61 | 0.5 | 0.66 | 23.03 | 1.81 | 40.26 | 67.02 | 37.15 | 66.89 | 3.11 | 0.13 | 3.24 | |
| | 14 | 1.OBJECT+3.012130 | 2094.09 | 222.54 | 695.43 | 3 | 3083.46 | 0.52 | 0.73 | 22.03 | 1.83 | 40.51 | 65.82 | 38.39 | 69.55 | 2.12 | -3.73 | 5.65 | |
| | 15 | 1.OBJECT+3.012115 | 2064.3 | 214.54 | 670.43 | 6 | 2972.81 | 0.54 | 0.77 | 21.63 | 1.73 | 41.19 | 63.8 | 39.85 | 70.45 | 1.34 | -6.65 | 7.99 | |
| | 16 | 1.OBJECT+3.012175 | 2174.022 | 211.81 | 661.91 | 0 | 2517.19 | 0.51 | 0.76 | 20.63 | 1.64 | 42.38 | 62.36 | 41.73 | 68.38 | 0.65 | -6.69 | 7.34 | |
| | 17 | 1.OBJECT+3.012179 | 2177.93 | 203.23 | 635.88 | 3 | 2844.59 | 0.57 | 0.72 | 18.85 | 1.51 | 43.76 | 60.78 | 44.09 | 66.08 | -0.33 | -5.3 | 4.97 | |
| | 18 | 1.OBJECT+3.011920 | 1875.6 | 189.33 | 591.64 | 12 | 2487.57 | 0.47 | 0.69 | 18.67 | 1.49 | 45.22 | 58.55 | 45.4 | 61.85 | -1.18 | 3.3 | 2.12 | |
| | 19 | 1.OBJECT+3.011374 | 1341.77 | 164.98 | 515.57 | 15 | 1741.26 | 0.47 | 0.6 | 19.81 | 1.59 | 47.12 | 54.41 | 47.97 | 56 | -0.85 | -1.59 | 0.74 | |
| | 20 | 1.OBJECT+3.011363 | 5693.36 | 125.33 | 391.64 | 27 | 843.91 | 0.33 | 0.69 | 26.94 | 2.14 | 47.9 | 45.96 | 47.98 | 46 | -0.08 | -0.04 | 0.04 | |

SYSTEMS, METHODS, COMPOSITIONS AND DEVICES FOR IN VIVO MAGNETIC RESONANCE IMAGING OF LUNGS USING PERFLUORINATED GAS MIXTURES

RELATED APPLICATIONS

This application is a continuation application of U.S. patent application Ser. No. 13/577,926, filed Sep. 14, 2012, which is a 35 USC 371 national phase application of PCT/US2011/025011, filed Feb. 16, 2011, which claims the benefit of and priority to U.S. Provisional Application Ser. No. 61/305,025 filed Feb. 16, 2010 and U.S. Provisional Application Ser. No. 61/435,599 filed Jan. 24, 2011, the contents of which are hereby incorporated by reference as if recited in full herein.

FIELD OF THE INVENTION

The present invention relates to non-invasive in vivo $^{19}$F Magnetic Resonance Imaging ("MRI") using perfluorinated gas mixtures.

BACKGROUND OF THE INVENTION

The Centers for Disease Control (CDC) has stated that COPD (chronic obstructive pulmonary disease) has escalated to the 3$^{rd}$ leading cause of death in this country. See, A M, Miniño, Xu J Q, and Kochanek K D (2010), 'Deaths: Preliminary Data for 2008.', *National Vital Statistics Reports,* 59 (2), John Walsh (President, COPD Foundation) remarked that "It's unacceptable that COPD has gone from the fourth leading cause to the third twelve years sooner than what was originally projected. This wake-up call intensifies our declaration of war on COPD and points to the importance of improved awareness, prevention, detection and treatment to decrease the burden of COPD". {Foundation, COPD (2010), 'New CDC Report Puts COPD in #3 Spot in Mortality Rates'} In contrast to other top causes of death, COPD is the only disease in the top ten that has consistently increased in frequency over the past 4 decades. Consequently COPD represents one of the largest uncontrolled disease epidemics in the U.S.; it currently includes 15-20 million diagnosed cases with perhaps a similar number undiagnosed. In the U.S., there are approximately 90 million current or former smokers, (Association, 2008); thus, a huge population is at risk of developing COPD. COPD is defined by the Global Initiative for Chronic Obstructive Lung Disease (GOLD) as a disease state characterized by airflow limitation that is not fully reversible. Heron et al., "Deaths: Final Data for 2006." *National Vital Statistics Reports* 57(14): 1-135 (2009).

There is clear recognition that COPD includes both emphysema and small airway disease; however, there is little appreciation of how to identify COPD early—before there is significant airflow obstruction and clinical impairment. In addition, evidence from the COPD Gene study suggests that COPD is likely several diseases but currently the only tool that seems to provide any clinical differentiation of the genotypes is "gas trapping" patterns assessed by HRCT (High Resolution X-ray Computed Tomography).

Current approaches for the evaluation of pulmonary lung function use global measures of pulmonary function such as spirometry (e.g., forced expiratory volume in 1 second ("FEV1")) and whole body plethysmography. While spirometry is low cost and widely available, it does not yield any regional information about ventilation distribution or ventilation dynamics in the lung.

Currently available lung imaging methods include x-ray CT, which offers anatomic detail but limited functional information, and nuclear techniques such as scintigraphy, which provide regional information at low resolution in two dimensions rather than three (or more). Also, these modalities deliver ionizing radiation, which limits their repeat use in patients, especially in clinical trials.

More recently, hyperpolarized gas MRI using the stable isotopes $^3$He and $^{129}$Xe has offered hope for non-invasive, regional assessment of lung function. Unfortunately, this technology is relatively expensive and has not been widely disseminated.

SUMMARY OF EMBODIMENTS OF THE INVENTION

Embodiments of the invention provide systems, methods and related devices that allow for static and/or dynamic in vivo $^{19}$F MRI of the lungs using perfluorinated gas and oxygen gas mixtures.

The term "perfluorinated gas" ("PFx" gas) refers to inert medical grade gases derived from common organic perfluorocarbon or other perfluorinated compounds with the hydrogen atoms replaced with fluorine atoms.

Embodiments of the invention provide ways to evaluate ventilation dynamics (e.g., function) of a patient's lungs.

Embodiments of the invention can provide images of the gas spaces in the lung and be used for quantitative analysis of MR image data for lung function and/or regional ventilation assessment of the lung. For example, the MRI data can be used to assess, identify and/or visualize regional ventilation data (e.g., pattern) associated with function, ventilation defects and/or gas trapping (regional and temporal).

Embodiments of the invention can provide dynamic "free-breathing" cine images of a breathing lung (corresponding to a respiratory cycle). Some embodiments can provide dynamic images or pseudo-static images using gated image data collection over a plurality of respiratory cycles of a subject and reconstructed in a variety of manners to accommodate the respiratory cycle. Other embodiments employ short and/or long breath-hold techniques. Other embodiments include prospective or retrospective signal averaging of multiple image sets to improve the image quality (signal to noise and contrast to noise).

Embodiments of the invention can generate be used to obtain both $^1$H images and $^{19}$F images in a single imaging session of a subject. Optionally, air-breaths and the PFx/oxygen gas breaths can be cycled during the imaging session to alternate the $^1$H and $^{19}$F image data collection and/or to provide gas trapping data. Other embodiments include sequential breath-hold images or time gated images to identify wash-in and wash-out information. These embodiments can be used to grade the severity of any ventilation defects.

Changes in signal intensity of some of the PFx mixtures are sensitive to local oxygen concentration. In such an embodiment an estimate of oxygen gas exchange (perfusion) can be accomplished using T1 weighed images or calculated T1 images. It is noteworthy that this latter embodiment can use a PFx agent with longer T1 relaxation times, e.g., above about 10 ms, such as perfluoropropane (with a T1 relaxation time about 20 ms).

Embodiments of the invention can be used to obtain data to identify ventilation and/or perfusion variations (deficits or increases) before and after a physiologically active substance is administered to a human or animal body to evaluate the efficacy of the drug treatment.

Embodiments of the invention can be carried out post-administration of the PFx gas mixture as a post administration data collection analysis method to analyze signal data. The methods can, post administration and/or post signal collection, generate images, generate ventilation defect index, generate visual model of lung impairment and the like. The post-collection analysis can be carried out at any point in time after the delivery of the gas mixture, such as, for example, after the patient is removed from the MRI suite or magnet or when the patient is breathing oxygen, but in the MRI suite/magnet.

Embodiments of the invention are directed to post-collection analysis ventilation assessment methods. The methods include generating at least one of the following using pre-acquired $^{19}$F magnetic resonance image (MRI) signal data of a patient associated with a perfluorinated gas and oxygen mixture: (i) a cine of free-breathing images of the lungs of the subject illustrating a temporal and spatial distribution of the perfluorinated gas in the lung space and lungs of the subject to provide ventilation image data over at least one respiratory cycle;

(ii) at least one ventilation defect index for each of the right and left lungs;

(iii) a ventilation defect index map showing a spatial distribution (pixel wise) of the lungs;

(iv) a visual output to a display, the output including a time sequence of airflow data of the subject with a plurality of MRI images positioned aligned with an acquisition time, in the time sequence;

(v) a ventilation pattern associated with a forced ejection volume;

(vi) at least one histogram associated with wash-in and/or wash-out of the gas mixture;

(vii) at least one regional ventilation defect model showing intensity variation pixel to pixel;

(viii) gas trapping images using wash in and/or wash out $^{19}$F MRI signal data;

(ix) a visual output of a graphic analysis fit to a lung model of ventilation wash-in and/or wash-out with a plurality of MRI images depicting functional information;

(x) a pattern of signal intensity depicting gas exchange to capillary blood flow based on relaxation parameters (T1 and/or T2) and an impact of local oxygen concentration on the relaxation parameters; and (xi) at least one histogram associated with wash-in and/or wash-out of the delivered gas mixture.

Still other embodiments are directed to methods of obtaining image data of the lungs and/or airways of a subject. The methods include: (a) positioning a subject in a magnetic field associated with a high-field magnet of an MRI scanner; (b) delivering a medical grade gas mixture to the lung space of the subject, the gas mixture comprising between about 20-79% inert perfluorinated gas and at least about 21% oxygen gas; (c) acquiring $^{19}$F magnetic resonance image (MRI) signal data associated with the delivered perfluorinated gas and oxygen mixture; and (d) generating at least one of the following using the acquired signal data: (i) a cine of free-breathing images of the lungs of the subject illustrating a temporal and spatial distribution of the perfluorinated gas in the lung space and lungs of the subject to provide ventilation image data over at least one respiratory cycle; (ii) at least one ventilation defect index for each of the right and left lungs; (iii) a ventilation defect index map showing a spatial distribution (pixel wise) of the lungs; (iv) a visual output to a display, the output including a time sequence of airflow data of the subject with a plurality of MRI images positioned aligned with an acquisition time, in the time sequence; (v) a ventilation pattern associated with a forced ejection volume; (vi) at least one histogram associated with wash-in and/or wash-out of the gas mixture; (vii) at least one regional ventilation defect model showing intensity variation pixel to pixel; (viii) gas trapping images using wash in and/or wash out $^{19}$F MRI signal data; (ix) a visual output of a graphic analysis fit to a lung model of ventilation wash-in and/or wash-out with a plurality of MRI images depicting functional information; (x) a pattern of signal intensity depicting gas exchange to capillary blood flow based on relaxation parameters (T1 and/or T2) and an impact of local oxygen concentration on the relaxation parameters; and (xi) at least one histogram associated with wash-in and/or wash-out of the delivered gas mixture.

Some embodiments generate a plurality of the generated images, maps, indexes, or data (per items i-xi).

The methods can include generating free breathing cine images of the lungs of the subject illustrating a temporal and spatial distribution of the perfluorinated gas in the lung space and lungs of the subject to provide ventilation image data over at least one respiratory cycle (typically over a plurality of respiratory cycles and during at least one of wash in and wash out of the gas mixture).

Optionally, the delivering step can be carried out using free-breathing, thereby allowing the subject to inhale and exhale the gas mixture over a plurality of respiratory cycles during the acquiring step.

In some embodiments, the methods can further include terminating the delivering step, then allowing the subject to breathe room air while remaining in the magnetic field of the MRI Scanner. The method then acquires additional $^{19}$F MRI signal data gas and evaluates ventilation data associated with gas trapping using the additionally acquired MRI signal data.

The evaluating step may be carried out by generating images using the acquired MRI data illustrating a temporal and spatial distribution of the perfluorinated gas in the subject.

The perfluorinated gas mixture can include medical grade sulfur hexafluoride that is in a gaseous state at room temperature and pressure. The perfluorinated gas mixture can include a medical grade perfluoropropane gas that is in the gaseous state at room temperature and pressure. Other embodiments can include other medical grade perfluorinated gases such as perfluoroethane, etc., although at this time only sulfur hexafluoride and perfluoropropane are available in medical grades.

In some embodiments, the method can also include directing the subject to carry out a forced ejection volume breathing maneuver in one second (FEV1) of the gas mixture. Then the method can acquire MRI signal data during and/or after the forced ejection of the gas mixture and generate and evaluate a ventilation pattern based on the acquired MRI signal data of the FEV procedure.

Optionally, the method may also include performing a spirometry procedure of the subject while the subject is in a supine position proximate in time to the positioning step.

In some embodiments, the method can include generating at least one histogram of image intensity data using the acquired MRI signal data to identify ventilation defects.

The acquiring step can include acquiring the $^{19}$F MRI signal data from a flexible or rigid lung coil positioned about the subject and the method can further include proton blocking the lung coil and substantially concurrently or sequentially acquiring $^{1}$H and $^{19}$F MR image signal data.

In some embodiments, the method can further include generating images using respiratory cycle gating so that the acquiring step is performed over several respiratory cycles. The generating step can generate gated cine images of a breathing lung of the patient with temporal and spatially distributed ventilation data in near-real time.

Other embodiments are directed to MRI systems. The systems include: (a) an MRI scanner comprising a magnet with a magnetic field and a body coil configured to obtain $^1$H MRI signal data; (b) a flexible, semirigid or rigid lung coil configured to obtain $^{19}$F MRI signal data and sized and configured to reside about a patient; (c) an MRI scanner interface in communication with the scanner and the lung coil, the interface comprising a proton blocking circuit; and (d) a gas delivery system. The gas delivery system includes: (i) a gas mixture source comprising perfluourinated gas in a level that is between about 20-79% and oxygen gas in a level that is at least about 21%; (ii) a gas flow path in communication with the gas mixture source comprising at least one conduit extending from the gas mixture source to a dispensing member residing over, on or in a patient while the patient resides inside the magnetic field to deliver the gas mixture to the patient; and (iii) optionally, at least one oxygen sensor in communication with the gas mixture. In operation, the MRI system is configured to substantially concurrently obtain $^1$H and $^{19}$F MRI signal data of lungs and associated lung airspaces of the patient and generate images showing a temporal and spatial distribution of the perfluorinated gas mixture in the lungs.

The system can optionally be configured to acquire the $^1$H and $^{19}$F MRI signal data while (a) the patient carries out free-breathing of the gas mixture for a plurality of respiratory cycles then (b) the patient carries out free-breathing of room air for a plurality of respiratory cycles, and wherein the system is configured to generate cine images of a breathing lung using the acquired signal data.

Some embodiments are directed to MRI systems that include: (a) an MRI scanner comprising a magnet with a magnetic field and a body coil configured to obtain $^1$H MRI signal data; (b) a lung coil configured to obtain $^{19}$F MRI signal data and sized and configured to reside proximate a patient; (c) an MRI scanner interface in communication with the scanner and the lung coil, the interface comprising a proton blocking circuit; and (d) a gas delivery system. The gas delivery system can include: a gas mixture source comprising perfluourinated gas in a level that is between about 20-79% and oxygen gas in a level that is at least about 20.5%; a gas flow path in communication with the gas mixture source comprising at least one conduit extending from the gas mixture source to a free-breathing dispensing member residing over, on or in a patient while the patient resides inside the magnetic field to deliver the gas mixture to the patient; and at least one oxygen sensor in communication with the gas mixture.

In operation, the MRI system is configured to obtain $^1$H and $^{19}$F MRI signal data of lungs and associated lung airspaces of the patient and generate images showing a temporal and spatial distribution of the perfluorinated gas in the lungs, wherein the system is configured to acquire the $^{19}$F MRI signal data while the patient carries out at least one of (a) free-breathing of the gas mixture during equilibrium and wash in and/or wash out for a plurality of respiratory cycles, (b) a single or a plurality of breath holds of the gas mixture; and (c) an FEV of the gas mixture.

The system can be configured to generate at least one of the following:

(i) a cine of free-breathing images of the lungs of the subject illustrating a temporal and spatial distribution of the perfluorinated gas in the lung space and lungs of the subject to provide ventilation image data over at least one respiratory cycle;

(ii) at least one ventilation defect index for each of the right and left lungs;

(iii) a ventilation defect index map showing a spatial distribution (pixel wise) of the lungs;

(iv) a visual output to a display, the output including a time sequence of airflow data of the subject with a plurality of MRI images positioned aligned with an acquisition time, in the time sequence;

(v) a ventilation pattern associated with a forced ejection volume;

(vi) at least one histogram associated with wash-in and/or wash-out of the gas mixture;

(vii) at least one regional ventilation defect model showing intensity variation pixel to pixel;

(viii) gas trapping images using wash in and/or wash out $^{19}$F MRI signal data;

(ix) a visual output of a graphic analysis fit to a lung model of ventilation wash-in and/or wash-out with a plurality of MRI images depicting functional information;

(x) a pattern of signal intensity depicting gas exchange to capillary blood flow based on relaxation parameters (T1 and/or T2) and an impact of local oxygen concentration on the relaxation parameters; and (xi) at least one histogram associated with wash-in and/or wash-out of the delivered gas mixture.

The MRI system can be configured to substantially concurrently obtain the obtain $^1$H and $^{19}$F MRI signal data of the lungs. The system can include an image analysis circuit that is configured to electronically terminate the gas delivery and allow the patient to breathe room air for a plurality of respiratory cycles.

Still other embodiments are directed to MRI systems that include: (a) an MRI scanner having a control console in a first room and a magnet with a magnetic field in a scan room; and (b) a gas delivery system. The gas delivery system includes: (i) a pressurized container of a gas mixture comprising perfluorinated gas in a level that is between about 20-79% and oxygen gas in a level that is at least about 21%; (b) a gas flow path in communication with the gas mixture source comprising at least one conduit and at least one flexible bag extending from the container to a dispensing member while the patient resides inside the magnetic field; and (c) optionally, at least one oxygen sensor in communication with the gas mixture in the gas flow path. In operation, the MRI system is configured to obtain $^{19}$F MRI signal data and generate images showing a temporal and spatial distribution of the perfluorinated gas in the lungs.

The system can optionally be configured to acquire the $^1$H and $^{19}$F MRI signal data while (a) the patient carries out free-breathing of the gas mixture for a plurality of respiratory cycles, then (b) the patient carries out free-breathing of room air for a plurality of respiratory cycles, and wherein the system is configured to generate cine images of a breathing lung using the acquired signal data.

Still other embodiments are directed to gas delivery systems for an MRI system. The gas delivery system includes: (a) a medical grade gas mixture source of perfluorinated gas and oxygen gas; (b) a mouthpiece and/or mask residing downstream of the gas mixture source configured to reside inside a magnetic field of the MRI system; and (c) a flow path extending from the gas mixture source to the mouthpiece and/or mask. The flow path includes a first Douglas bag in fluid communication with the gas mixture source and may include a first spirometer filter residing downstream of the first Douglas bag.

The gas delivery system may optionally also include a one-way valve in communication with the mouthpiece or mask residing downstream of the first spirometer filter, a second spirometer filter residing downstream of the mouthpiece or mask, and a second Douglas bag residing downstream of the second spirometer filter whereby a patient can passively intake and exhale the gas mixture.

The system can include a display in communication with the MRI scanner and a respiratory cycle gating circuit and an image analysis circuit in communication with the MRI scanner. The MRI system can be configured to generate gated free-breathing cine images with image data registered to a respiratory cycle using $^{19}F$ image data acquired over a plurality of patient respiratory cycles, and wherein the display is configured to present the gated cine images in near real-time showing the lungs of the patient with temporal and spatially distributed ventilation data associated with the $^{19}F$ image data.

The gas flow path can include an inspire gas flow path and an expire gas flow path, the system further comprising a first pneumotachometer residing in the inspire gas flow path and a second pneumotachometer residing in the expire gas flow path, and wherein the respiratory gating circuit is configured to use pneumotachometer data for respiratory gating input.

The system can include an image analysis circuit that is configured to register $^{19}F$ MRI lung images to a set of $^{1}H$ MRI lung images of the subject, create lung masks from the $^{1}H$ MRI images, apply the created masks to the registered $^{19}F$ images, then extract summary parameters from the $^{19}F$ image data to assess ventilation defects. The summary parameters can be extracted by volume and slice and include at least one of pixel intensity, pixel count, histogram, summary statistics and 2-D shape factors.

The system can include a gas chamber in fluid communication with an expire portion of the gas flow path positioned upstream of a Douglas bag for gas capture. The gas chamber can be in communication with a chemical analyzer configured to analyze oxygen and carbon dioxide content in substantially real time.

The system can include a display and an image analysis circuit in communication with the MRI Scanner, the image analysis circuit configured to generate an overlay presentation of patient airflow data over time aligned with a plurality of MRI images taken at different points in time including inspire and expire breath-hold images of air, wash-in and wash out images of the perfluorinated gas mixture and free-breathing perfluorinated cine MRI images.

Still other embodiments are directed to a gas delivery system for an MRI system. The gas delivery systems include: (a) a medical grade gas mixture source of perfluorinated gas and oxygen gas; (b) a mouthpiece and/or mask residing downstream of the gas mixture source configured to reside inside a magnetic field of the MRI system; and (c) an inspire flow path extending from the gas mixture source to the mouthpiece and/or mask. The flow path can include: a first Douglas bag in fluid communication with the gas mixture source; and a first spirometer filter residing downstream of the first Douglas bag. The gas delivery system can be a passive system that allows a patient to "breath-hold" and freely breathe the gas mixture.

The gas delivery system can also include enclosed expire gas flow path residing downstream of the mouthpiece or mask. The gas delivery system can also include: a one-way valve in communication with the mouthpiece and/or mask residing downstream of the first spirometer filter; a second spirometer filter residing downstream of the mouthpiece and/or mask in the expire gas flow path; and a second Douglas bag with a larger size than the first Douglas bag residing downstream of the second spirometer filter.

The delivery system can include an enclosed expire gas flow path residing downstream of the mouthpiece or mask, a first pneumotachometer in fluid communication with the inspire gas flow path; a second pneumotachometer in fluid communication with the expire gas flow pathmask; at least one pneumotachometer recorder in communication with the first and second pneumotachometers; a gating circuit interface in communication with the at least one recorder configured to provide MRI respiratory gating input; a gas chamber in the expire gas flow path upstream of a Douglas gas recovery bag; and a gas analyzer in communication with the gas chamber configured to analyze oxygen and carbon dioxide content of gas in the chamber.

Still other embodiments are directed to cines of free-breathing $^{19}F$ MRI images showing breathing lungs with a temporal and spatial distribution of perfluorinated gas associated with a ventilation pattern.

Yet other embodiments are directed to at least one right lung ventilation defect index and at least one left lung ventilation defect index, wherein the respective at least one index is determined based on MRI pixel signal intensity to thereby provide a patient-specific measure of lung function.

Additional embodiments are directed to a regional ventilation defect graph showing right and left lung ventilation of $^{19}F$ pixel signal intensity of perfluorinated gas in a subject's lungs over a defined time with signal intensity at the defined time used to identify a ventilation defect for each of a right and left lung of the subject.

Other embodiments are directed to regional ventilation indexes and/or maps of pixel variation in the lungs associated with $^{19}F$ signal data.

Yet other embodiments are directed to a cine of MRI images showing breathing lungs with a temporal and spatial distribution of perfluorinated gas associated with a ventilation pattern.

Additional embodiments are directed to pressurized canisters of a medical grade gas mixture comprising at least about 21% oxygen and between about 20% to about 79% inert pefluorinated gas.

The canister may also include a temperature sensor on the canister for indicating whether the canister has been exposed to a temperature below 5° C.

Some embodiments are directed to a trifunctional medical grade gas composition for administration to a human patient, comprising about 21% oxygen gas and between about 20% to about 78% inert perfluorinated gas, and the balance anesthesia gas.

Embodiments of the invention are directed to systems and methods of imaging a spatial distribution of a perfluorinated gas by nuclear magnetic resonance spectrometry, which include detecting a spatial distribution of at least one perfluorinated gas by NMR spectrometry (e.g., MRI scanner) and generating a representation of the spatial distribution of the perfluorinated gas. The representation can be generated in 3-D volume or 2-D Multislice or projection images with an additional temporal dimension related to the ventilation pattern of the gas including the inhalation and exhalation phase. The perfluorinated gas may be imaged according to the invention in chemical or biological systems, preferably in a human or animal subject or organ system or tissue thereof.

Also, apparatus for nuclear magnetic resonance imaging of the spatial distribution of the perfluorinated gas includes means for imaging a perfluorinated gas by NMR spectrometry and means for providing and/or storing imageable quantities of a perfluorinated gas as well as the delivery of the gas to the subject.

Further, a medical composition may include a trifunctional gas mixture including a medical grade (inert) perfluorinated gas, medical grade oxygen and a third gas which may include an anesthetic gas or other relevant support gas (e.g., He).

Embodiments of the invention can employ a mathematical model that can be used to interrogate the image data and generate a map of regional ventilation function.

It is noted that aspects of the invention described with respect to one embodiment, may be incorporated in a different embodiment although not specifically described relative thereto. That is, all embodiments and/or features of any embodiment can be combined in any way and/or combination. Applicant reserves the right to change any originally filed claim or file any new claim accordingly, including the right to be able to amend any originally filed claim to depend from and/or incorporate any feature of any other claim although not originally claimed in that manner. These and other objects and/or aspects of the present invention are explained in detail in the specification set forth below.

The foregoing and other objects and aspects of the present invention are explained in detail herein.

BRIEF DESCRIPTION OF THE DRAWINGS

FIGS. 5A-5C are graphs of signal versus flip angle, each graph using a TR of 10 ms and a TE of 1 ms (all other T numbers are also shown in ms units). FIG. 5A is a signal plot of lung water. FIG. 5B is a signal plot of SF6 and FIG. 5C is a signal plot of PFP.

FIG. 13A shows two regions of interest 'grown' using a seeded approach while 13B shows a region of the entire 'object'.

FIGS. 17A and 17B are charts of examples of extracted summary parameters in slices of an image volume according to embodiments of the present invention.

DETAILED DESCRIPTION

Figure 1A:
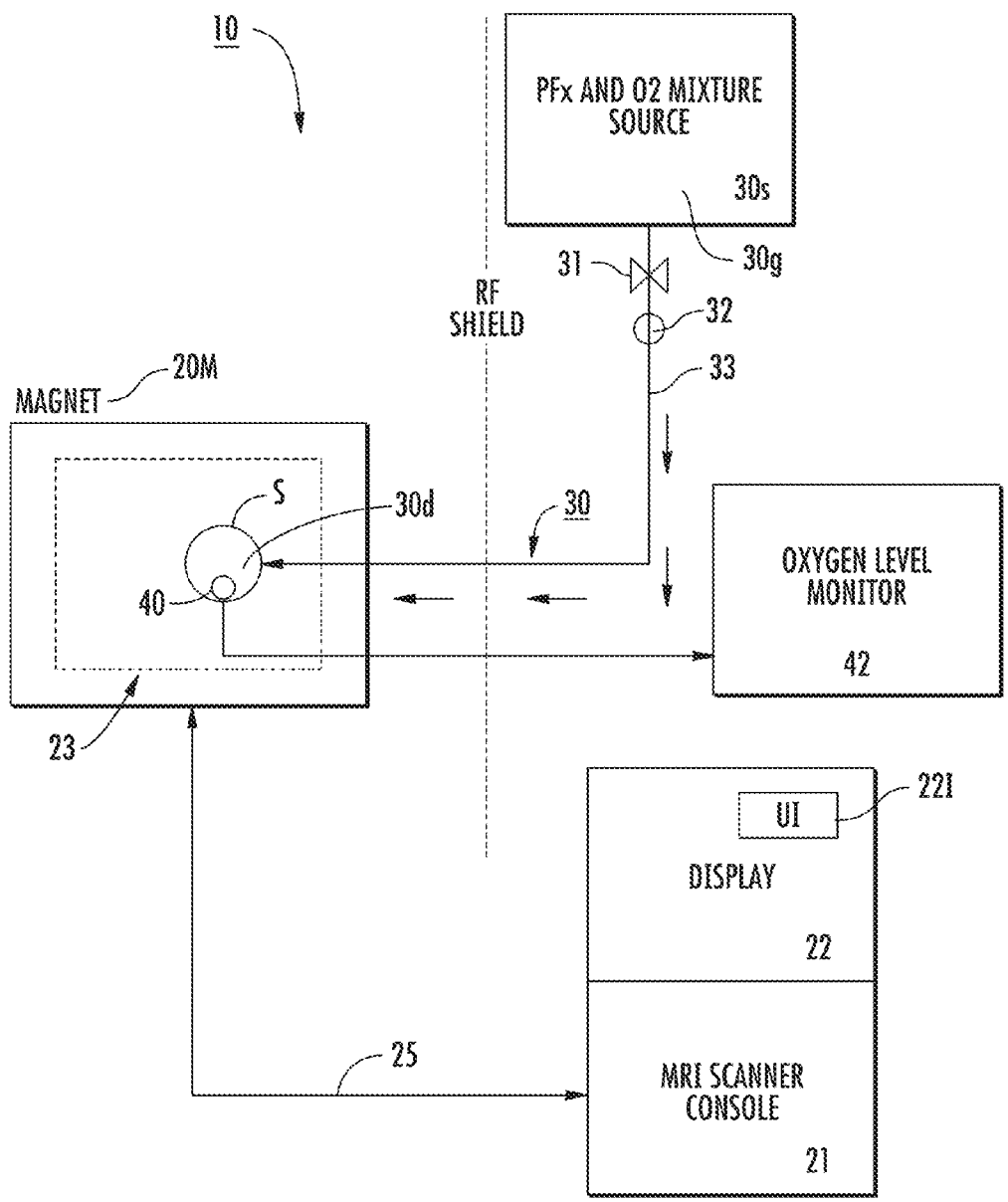
FIG. 1A is a schematic illustration of an MRI system with a gas delivery system according to embodiments of the present invention.

The present invention will now be described more fully hereinafter with reference to the accompanying figures, in which embodiments of the invention are shown. This invention may, however, be embodied in many different forms and should not be construed as limited to the embodiments set forth herein. Like numbers refer to like elements throughout. In the figures, certain layers, components or features may be exaggerated for clarity, and broken lines illustrate optional features or operations unless specified otherwise. In addition, the sequence of operations (or steps) is not limited to the order presented in the figures and/or claims unless specifically indicated otherwise. In the drawings, the thickness of lines, layers, features, components and/or regions may be exaggerated for clarity and broken lines illustrate optional features or operations, unless specified otherwise. Features described with respect to one figure or embodiment can be associated with another embodiment of figure although not specifically described or shown as such.

It will be understood that when a feature, such as a layer, region or substrate, is referred to as being "on" another feature or element, it can be directly on the other feature or element or intervening features and/or elements may also be present. In contrast, when an element is referred to as being "directly on" another feature or element, there are no intervening elements present. It will also be understood that, when a feature or element is referred to as being "connected", "attached" or "coupled" to another feature or element, it can be directly connected, attached or coupled to the other element or intervening elements may be present. In contrast, when a feature or element is referred to as being "directly connected", "directly attached" or "directly coupled" to another element, there are no intervening elements present. Although described or shown with respect to one embodiment, the features so described or shown can apply to other embodiments.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items.

It will be understood that although the terms "first" and "second" are used herein to describe various components, regions, layers and/or sections, these regions, layers and/or sections should not be limited by these terms. These terms are only used to distinguish one component, region, layer or section from another component, region, layer or section. Thus, a first component, region, layer or section discussed below could be termed a second component, region, layer or section, and vice versa, without departing from the teachings of the present invention. Like numbers refer to like elements throughout.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein. Well-known functions or constructions may not be described in detail for brevity and/or clarity.

In the description of the present invention that follows, certain terms are employed to refer to the positional relationship of certain structures relative to other structures. As used herein, the term "front" or "forward" and derivatives thereof refer to the direction that the gas mixture flows during use toward a patient (and where captured upon exhale, then away from a patient); this term is intended to be synonymous with the term "downstream," which is often used in manufacturing or material flow environments to indicate that certain material traveling or being acted upon is farther along in that process than other material. Conversely, the terms "rearward" and "upstream" and derivatives thereof refer to the direction opposite, respectively, the forward or downstream direction.

The term "circuit" refers to an entirely software embodiment or an embodiment combining software and hardware aspects, features and/or components (including, for example, a processor and software associated therewith embedded therein and/or executable by, for programmatically directing and/or performing certain described actions or method steps).

The term "map" refers to a rendered visualization of one or more selected parameters, conditions, or behaviors of pulmonary (lung) tissue or airway using MR image data, e.g., the map is a rendered partial or global anatomical map that shows ventilation and/or perfusion information in a manner that illustrates relative degrees or measures of function, typically using different colors, opacities and/or intensities.

The actual visualization can be shown on a screen or display so that the map or ventilation information images and/or anatomical structure is in a flat 2-D and/or in a 2-D projection image in what appears to be 3-D volumetric images with data representing features with different visual characteristics such as with differing intensity, opacity, color, texture and the like. A 4-D map can either illustrate a 3-D or 2-D projection image of the lung with movement (e.g., wall movement associated with a respiratory cycle) or a 3-D map with ventilation information during inhale and/or exhale.

The term "5-D visualization" means a 4-D visualization image (e.g., a dynamic/moving 3-D or 2-D projection image of a breathing lung) with functional (ventilation) spatially encoded or correlated information shown on the moving visualization.

The term "programmatically" means that the operation or step can be directed and/or carried out by a digital signal processor and/or computer program code. Similarly, the term "electronically" means that the step or operation can be carried out in an automated manner using electronic components rather than manually or using any mental steps.

The terms "MRI scanner" or MR scanner" are used interchangeably to refer to a Magnetic Resonance Imaging system and includes the high-field magnet and the operating components, e.g., the RF amplifier, gradient amplifiers and processors that typically direct the pulse sequences and select the scan planes. Examples of current commercial scanners include: GE Healthcare: Signa 1.5 T/3.0 T; Philips Medical Systems: Achieva 1.5 T/3.0 T; Integra 1.5 T; Siemens: MAGNETOM Avanto; MAGNETOM Espree; MAGNETOM Symphony; MAGNETOM Trio; and MAGNETOM Verio. As is well known, the MR scanner can include a main operating/control system that is housed in one or more cabinets that reside in an MR control room while the MRI magnet resides in the MR scan suite. The control room and scan room can be referred to as an MR suite and the two rooms are generally separated by an RF shield wall.

The term "cine" refers to a series of images shown dynamically, e.g., a breathing lung in motion during a respiratory cycle or cycles, and is typically carried out by looping image slices of a stack of images of the lungs and/or lung airways to form a dynamic series of images at a certain frame rate (typically stated in frames per second "fps"). The frame rate may be adjusted by a user to have a faster or lower speed for ease of review of lung function or the like.

The term "MRI compatible" means that the so-called component(s) is suitable for use in an MRI environment and as such is typically made of a non-ferromagnetic MRI compatible material(s) suitable to reside and/or operate in or proximate a conventional medical high magnetic field environment. The "MRI compatible" component or device is "MR safe" when used in the MRI environment and has been demonstrated to neither significantly affect the quality of the diagnostic information nor have its operations affected by the MR system at the intended use position in an MR system. These components or devices may meet the standards defined by ASTM F2503-05. See, American Society for Testing and Materials (ASTM) International, Designation: F2503-05. Standard Practice for Marking Medical Devices and Other Items for Safety in the Magnetic Resonance Environment. ASTM International, West Conshohocken, Pa., 2005.

The term "high-magnetic field" refers to field strengths above about 0.5 T, typically above 1.0 T, and more typically between about 1.5 T and 10 T. Embodiments of the invention may be particularly suitable for 3.0 T systems, or higher field systems such as future commercial systems at 4.0 T, 5.0 T, 6.0 T and the like, but can also be implemented at 1.5 T.

Generally stated, perfluorinated (which can be abbreviated by the term "PFx") gases can be used as imaging agents during MRI to allow data capture of regional ventilation information. As noted above, the term "perfluorinated gas" ("PFx" gas) refers to inert medical grade gases derived from common organic perfluorocarbon or other perfluorinated compounds with the hydrogen atoms replaced with fluorine atoms. For medical administration to humans and animals, the PFx gas should be formulated as a medical grade gas with toxic chemicals/elements removed or present at levels defined as acceptable for medical use and with microbial limits in compliance with (and testing performed to meet) regulatory microbe and medical grade guidelines, such as the those stated in USP Chapter 1111 as issued by the United States Food and Drug Administration in 2009 and USP 61 and 62. Examples of suitable PFx gases include sulfur hexafluoride gas ($SF_6$) and perfluoroalkanes, such as, but not limited to, Perfluoropropane ("PFP", also known as $C_3F_8$) that are gaseous at room temperatures and pressures. The nominal room temperatures are believed to be between about 20-25° C. and 1 atm (sea level) but the gas mixture can be used at lower and higher temperatures and a range of pressures, but below a pressure that can cause the gas to liquefy so as to maintain the composition of the gas. Other PFx gases may also be suitable such as perfluoroethane, perfluorocyclobutane, and perfluoromethane. The perfluorinated gas is at least thermally or equilibrium polarized by a static magnetic field generated by a magnet that is large enough to contain the subject "S".

Embodiments of the invention can generate a representation of the perfluorinated gas spatial distribution in the lungs/airways that includes at least one dimension, but preferably 2 or 3 dimensions of the spatial distribution. In addition, the representation can be provided in a fourth dimension (temporal) related to the ventilation pattern of the gas including the inhalation and exhalation phase.

Embodiments of the invention use conventional 'thermally' polarized perfluorinated gases (PFx) mixed with oxygen for use as inhaled inert MRI contrast agents to image lung function, e.g., ventilation and various ventilation defects. These PFx agents attain a relatively high thermal polarization exceptionally quickly, which, coupled with a large $^{19}F$ MR signal (magnetic moment) and molecular symmetry, allows imaging ventilation with a quality similar to that of hyperpolarized $^{129}Xe$ MRI, but at lower cost and with reduced technical complexity. SF6 has a T1 of about 2 ms while perfluoropropane has a T1 of about 20 ms. Thus, because of the different physicochemical properties and/or T1's, one or the other may be more suitable for different breathing patterns. The PFx gases can allow for rapid image acquisition with near real-time imaging of ventilation dynamics. The term "near real-time" means that the ventilation dynamic images can be generated while a patient is in the MRI scanner suite, typically within about 30 seconds to about 5 minutes from initial signal acquisition. An entire lung evaluation image session can be relatively short, typically between about 5-30 minutes, and more typically between about 10-15 minutes. The images can be obtained in a (gated) cine mode with free-breathing delivery.

It is also contemplated that from a ventilation information viewpoint, embodiments of the present invention can evaluate the MR image data from the PFx gas mixture to assess and/or measure gas trapping and can allow a temporal domain analysis of gas trapping that is not easily obtained with current imaging strategies. In addition, or alternatively, sequential breath-hold images or time gated images can identify wash-in and wash-out information. These embodiments can be used to grade the severity of the ventilation defects an approach also not easily obtained with current imaging strategies. Also, due to the relatively optimum relaxation conditions due to dominance of spin rotation relaxation on these agents and the ability to obtain a signal from the incoming gas delivery system, the contemplated systems may provide a more quantitative analysis and display of lung ventilation and/or functional information. Changes in signal intensity of the PFx mixtures are sensitive to local oxygen concentration. In some embodiments, an estimate of oxygen gas exchange (perfusion) can be accomplished using T1 weighed images, ratio or subtraction images or calculated T1 images. It is noteworthy that these embodiments can employ a PFx agent with longer T1 relaxation times, e.g., PFx agents having a T1 above about 10 ms, such as, for example, perfluoropropane.

Embodiments of the invention may be used with "free-breathing" delivery of the PFx gas mixture in contrast to breath-hold methodologies. The term "free-breathing" means that the subject is able to passively inhale and exhale the gas mixture in a substantially normal breathing or respiratory cycle without the requirement of "breath-hold" or a ventilator or regulated gas delivery system. It is noted that "free-breathing" may be carried out by directing the subject to inhale or exhale at a different rate, e.g., with faster or lower respiratory cycles, shallow or deep breaths or a forced ventilation breath (e.g., FEV1/FEC). The respiration can be via the nose and/or mouth but does not require that a patient actually hold his or her breath during the imaging. It is believed that the free-breathing delivery can provide improved accuracy in information regarding actual lung ventilation in the human lung(s) where a combination of convection and diffusion provide the ventilation dynamics over several breaths as the tidal volume is roughly ⅙th of the total volume. It is possible that ventilation defects found with other conventional (e.g., breath-hold) methods may not be accurate. In addition, "free-breathing" may make the system particularly suitable for patients with impaired breathing function and/or for pediatric use.

The lung contains three primary components: air (during normal breathing), blood and tissue. Generally stated, the structural and physiologic arrangement of these components provides for gas exchange and (typically) efficient resistance to the movement of air and blood. Also, the lung can provide for removal of particulate matter in inspired air by a specialized transport mechanism referred to as mucocilliary clearance (a homeostatic process). An example of a model used to describe geometric and/or morphologic changes can be obtained from R. Weibel, Morphometry of the Human Lung, Spinger-Verlag, Berlin, (1963), pp. 1-151; and The Physiology of Breathing, Grune & Stratton, 1977, New York, pp. 60-79; 173-232. It is contemplated that embodiments of the invention can generate images with ventilation data/patterns showing morphology and function based on the temporal and spatial distribution of the $^{19}$F (and $^{1}$H) signals in the lung space and tissue. It is noted that 19F is used interchangeably with the superscript version $^{19}$F and 1H is also used interchangeably with its superscript version $^{1}$H in this document.

Turning now to the figures, FIG. 1A illustrates a system 10 with an MRI scanner 20 and a gas delivery system 30. The MRI scanner 20 includes a high-field magnet 20M (typically in the scan room of the MRI suite). The magnet is typically at least about a 3.0 T magnet, but embodiments of the system 10 may be used with a 1.5 T magnet or a magnet at other higher field strengths. The MRI scanner 20 includes a control console 21 and a display 22. The display 22 can be integral with the console 21 and/or may be provided in a clinician workstation to display images. The scanner 20 can communicate with the body coil 23 typically included in the magnet housing in the scan room via lead 25 to direct the pulse sequence and transmit receive operation as is known to those of skill in the art.

The gas delivery system 30 includes a source 30s of perfluorinated gas ("PFx") and oxygen gas mixture 30g. The oxygen gas is typically provided in a normoxic amount, typically between about 20% and 21%, more typically between 20.5% to about 21%. The oxygen level should be maintained above 19.2%. Other gases may be included in the blend (mixture) as suitable for medical use. However, the PFx gas is typically provided in an amount that is between about 20%-79% of the gas mixture, and more typically between about 40% to about 79%.

The gas delivery system 30 includes at least one conduit 33 (e.g., typically flexible MRI compatible tubing) that extends from the source 30s to the delivery device 30d located proximate the subject "S" in the magnet 20M. The system 30 can include at least one valve 31 and flow regulator 32. The gas flow can be provided as a demand flow rate (controlled by the patient) or at suitable flow rates as is known to those of skill in the art and may vary by patient size age or breathing capacity.

The at least one conduit 33 can be provided as about a 15-50 mm diameter tubing, typically about a 38 mm diameter tubing, and may be single-use disposable. However, other size conduits may be used. Further, the subject can be isolated from the system by a high efficiency spirometry filter situated just after the delivery device 30d. The delivery device 30d can be in any suitable form, typically a mask or mouthpiece. However, the delivery device 30d can comprise an intubation tube as appropriate for a particular patient. The system 10 can include at least one oxygen sensor 40 that can be placed along the gas delivery path. An electrical and/or optical lead can extend from the sensor to the oxygen level monitor 42. Alternately, the (non-destructive) oxygen sensor system may continuously sample the source gas 30s using a pump system and return the gas to the source. The sensor 40 may also communicate with the monitor 42 wirelessly, e.g. Bluetooth.

As shown in FIG. 1A, the oxygen sensor 40 is placed proximate the delivery device 30d to confirm that the correct oxygen level is present in the gas mixture just prior to delivery to a patient. This sensor 40 can reside inside or outside of the magnet 20M. However, in other embodiments, the sensor 40 can reside upstream of the delivery device, such as proximate the source 30s. In other embodiments, a plurality of oxygen sensors 40 (FIGS. 1B, 3) can be used to provide redundancy in the oxygen verification/monitoring system. In some embodiments, a pulse oximetry system, such as a finger tip pulse oximetry system (for example, In Vivo MVS 3155 or the NONIN 7500FO) can also be used to measure patient oxygen saturation level (SpO2) (not shown) while the patient is in position in the scanner bore. A small drop in oxygen saturation (SpO2 about 1-2%) may be expected, in particular if breathhold techniques are used. The SpO2 may be monitored for larger changes which could determine if the study is to be terminated. A minimum SpO2 can be set with an alarm feature on most oximetry systems.

The source 30s can comprise two separate gas supplies, one for oxygen and one for PFx that can be mixed in situ at a clinical use site, such as in real time or prior to the procedure, to provide the desired blend for the procedure and monitor for and/or filter any undesired microbes. A monitor can include one or more lasers or other sensor(s) to confirm the correct oxygen percentage is present. In such an embodiment, the microbial levels can be determined on the source gases independently.

Figure 2A:
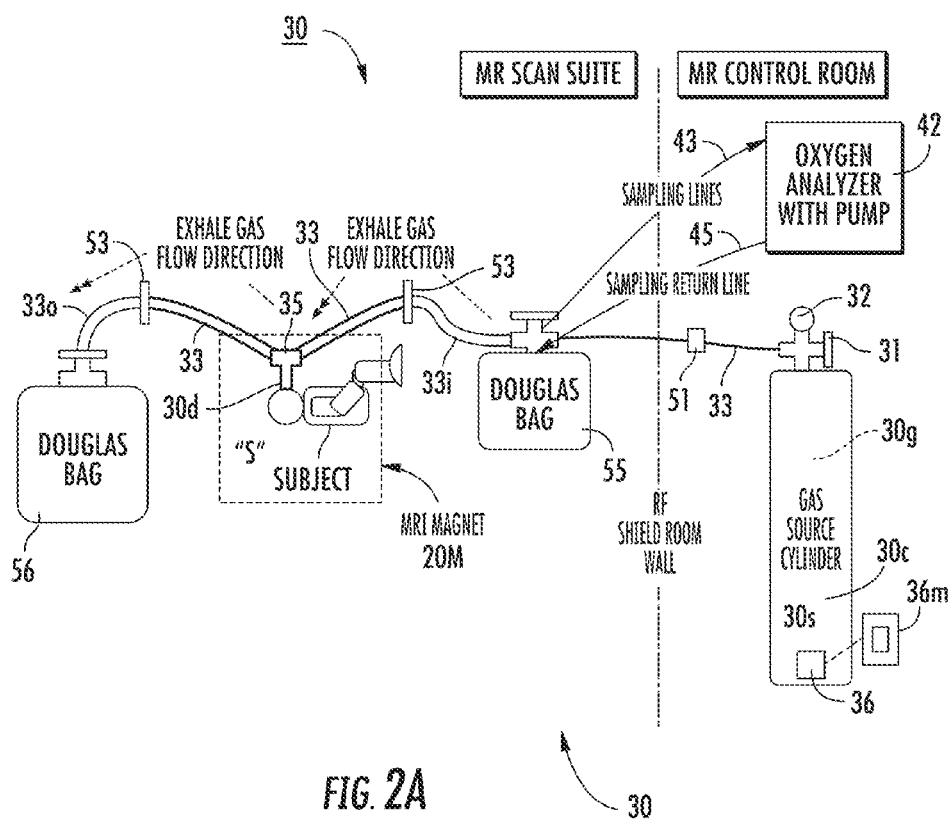
FIG. 2A is a schematic illustration of another gas delivery system according to embodiments of the present invention.

In other embodiments, the PFx gas and oxygen gas 30g may be supplied as a pre-mixed gas at low pressure in a pressurized canister 30c (FIG. 2A). For example, an 8 inch diameter 52 inch canister of SF6 (at about 79%) and $O_2$ (at about 21%) at 234 psig can provide about 472 liters of the $SF_6$ gas mixture. An 8 inch diameter 52 inch canister of PFP (at about 79%) and $O_2$ (at about 21%) at 68 psig can provide about 136 liters of the gas mixture. Smaller (e.g., personal use) size canisters or larger canisters may be used. Suitable medical grade gas mixtures can be obtained from Air Liquide, Scott Medical Products, Plumsteadsville, Pa. The source 30s can be placed in the control room or in the scan room or even outside the MR suite and flowably directed into the suite via delivery lines. If placed in the scan room (inside the RF shield), then aluminum or other suitable MRI-compatible material can be used to form the canister or components of the system. The gases are supplied at low pressure so that the dense gas component remains in the gaseous state under normal operating conditions of about 21 degrees C. or room temperature. Because both components are in the gaseous phase at this temperature, the component ratio of the mix that is drawn out of the cylinder will remain constant.

Exposures to low temperatures should be avoided (store and use above about 5° C./41° F. or, in some embodiments, above about 10° C./50° F.) as condensation of one of the components (namely, the $SF_6$ or $C_3F_8$) may occur, thereby disturbing the component ratio of the vapor phase. In such a situation, the gas cylinder can be warmed to room temperature and 'mixed' by rotation of the cylinder and the concentration checked as previously described, particularly, the oxygen level by an oxygen sensor 40. Thus, where pre-mixed pressurized gas sources are used, a low temperature indicator or sensor can be placed on or in the container 30c. The gas mixture is formulated to have a "dew point" of 0 degrees C. so that it will not condense above this temperature. The vapor pressure of PFP at 0 degrees C. is 60.41 psi and the vapor pressure of SF6 at 0 degrees C. is 182.01 psi. To determine the overall pressure of the mixture (at 0 degrees C.), the vapor pressure is divided by the concentration of the mixture. Then this number can be multiplied by 294/273 (degree Kelvin to degree C. conversion) to find the pressure at 21 degrees C./70 degrees F.

For 79% PFP:

$$60.41/0.79=76.46 \text{ psia}@0° \text{ C.}\times 294/273=82.35$$
$$\text{psia}@21° \text{ C.}-14.7=67.65 \text{ psig}@21° \text{ C.}$$

For 79% SF6:

$$182.01/0.79=230.39 \text{ psia}@0° \text{ C.}\times 294/273=248.11$$
$$\text{psia}@21° \text{ C.}-14.7=233.41 \text{ psig }@21° \text{ C.}$$

Figure 1B:
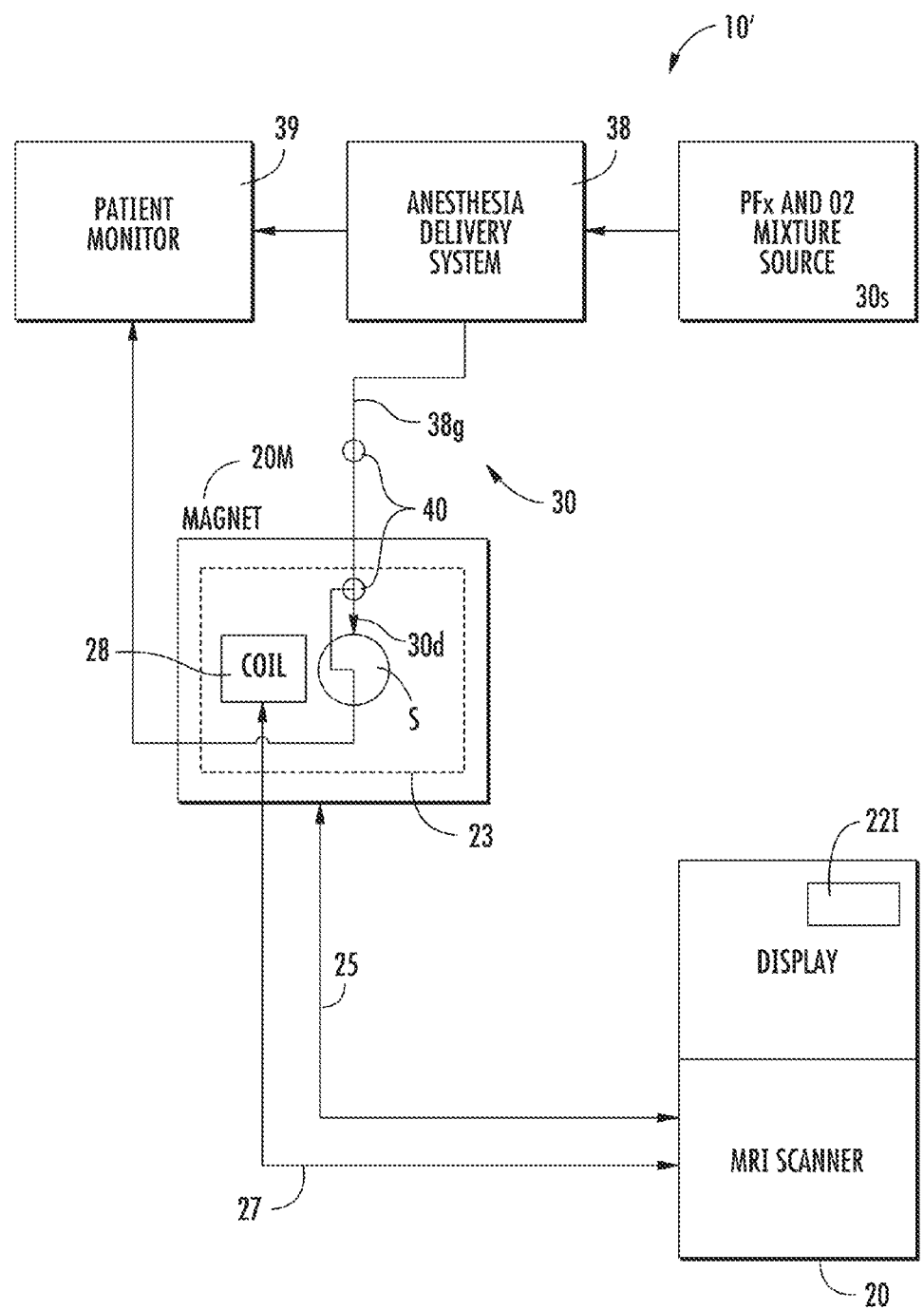
FIG. 1B is a schematic illustration of an MRI system with an alternate gas delivery system according to embodiments of the present invention.

FIGS. 1A and 1B illustrate a display 22 configured with a user interface (UI) 22I. The display 22 can present a ventilation map or a display of lungs with regional ventilation information data. For example, the ventilation map can comprise a 3-D anatomical map of at least a region of the lung with spatially correlated intensity data associated with, for example, gas trapping and/or wash in and wash out of a PFx gas, taken from MR image data incorporated therein. The UI 22I may also be configured to display intensity histograms (pixel intensity over time), typically correlated to a lung/ventilation defect, a ventilation defect (numeric or alphanumeric) index and the like. The UI 22I can be configured to allow a user to zoom, crop, rotate, or select views of the map. The UI 22I can include multiple different GUI (Graphic User Input) controls for different functions and/or actions. The GUI controls may also be a toggle, a touch screen with direction sensitivity to pull in a desired direction or other graphic or physical inputs.

Figure 1C:
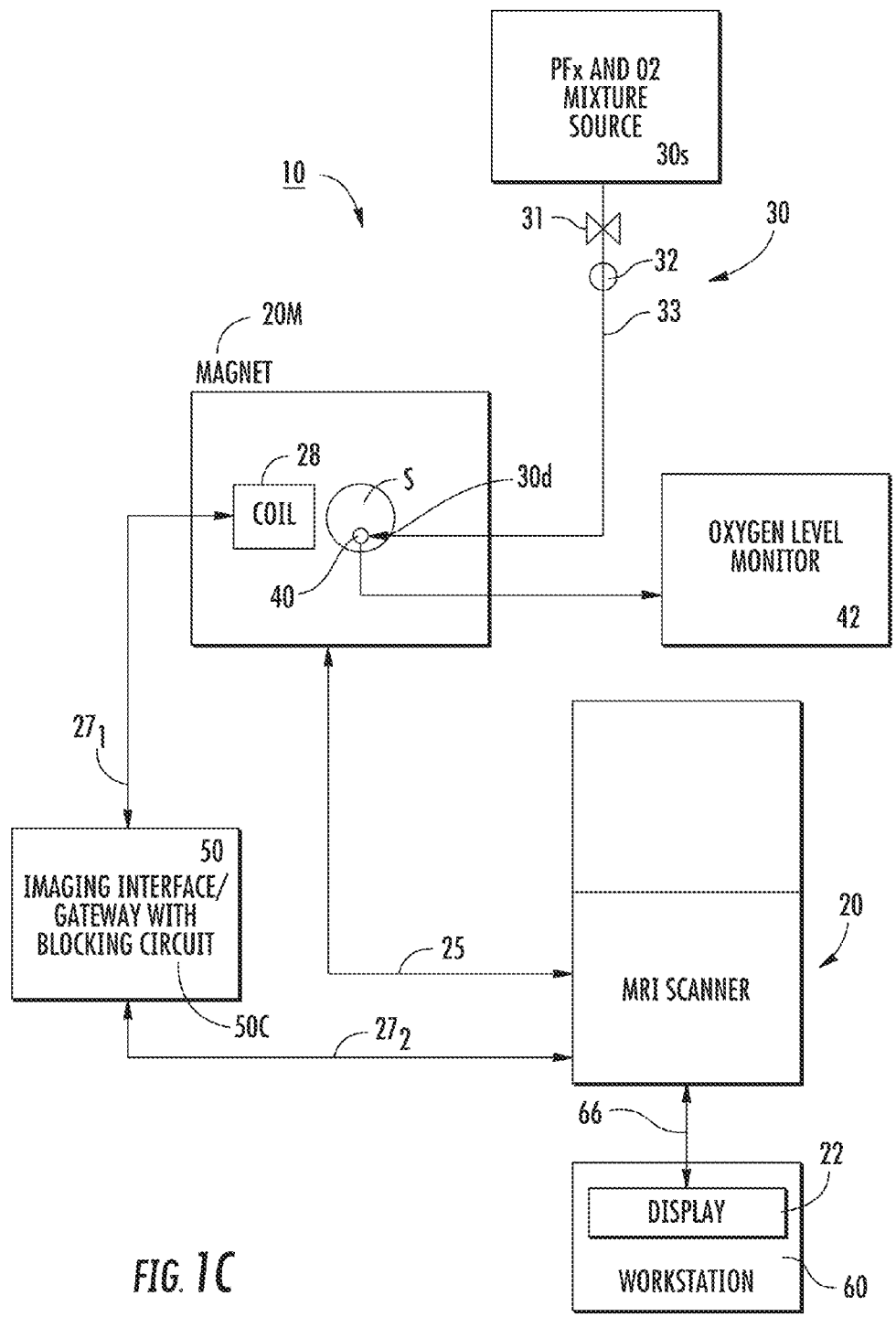
FIG. 1C is a schematic illustration of an MRI system and gas delivery system similar to those shown in FIGS. 1A and 1B but with an imaging gateway/interface according to embodiments of the present invention.

The UI 22I can include a list of user selectable images associated with the procedure that can be selected for viewing by a user. The UI 22I can also include GUI controls that allow a user to select two or more of the images, typically maps, to be shown together (overlaid and registered such as fused $^1H$ and $^{19}F$ lung images). As shown in FIG. 1C, the display 22 can be provided in or associated with a stand alone workstation 60 in communication with the MRI scanner 20. The workstation 60 can include a circuit (e.g., ASIC and/or processor with software) that includes or executes part or all of the computer readable program code for generating the ventilation map(s), ventilation images with regional ventilation information, and/or cines of a breathing lung showing lung function. However, part or all of the circuit can reside in the MRI scanner 20 or in one more remote processors.

Optionally, an MRI scanner interface 66 may be used to allow communication between the workstation 60 and the scanner 20. The interface 66 and/or circuit may be hardware, software or a combination of same. The interface 66 and/or circuit may reside partially or totally in the scanner 20, partially or totally in the workstation 60, or partially or totally in a discrete device therebetween. The display 20 can be configured to render or generate near real-time visualizations of the target anatomical space/lungs using MRI image data.

FIG. 1B illustrates that the system 10' can include an MRI compatible anesthesia delivery system 38 that provides an anesthesia (such as a general anesthesia) along with the gas mixture from the source 30s. Where this type of anesthesia-based system is used, the oxygen can be at a level that is between about 20-21%, the anesthesia gas can be at a level between about 5-20%, typically about 15%, and the PFx gas can be at a level of between about 75%-59%.

FIG. 1B also illustrates that the system 10' can include a patient monitor 39 which can monitor oxygen level in the general anesthesia delivery gas 38g as well as other patient vital signs. The patient monitor 39 can be separate from or integral with the anesthesia delivery system 38 monitoring system.

FIGS. 1B and 1C also illustrate that the system 10, 10' can also include a $^{19}F$ transmit/receive lung coil 28. The coil 28 is tuned to a selected frequency range associated with $^{19}F$ for the MRI field strength in use (e.g., about 115 MHz for a 3 T system) and positioned on a subject/patient to transmit the excitation pulses and to detect responses to the pulse sequence generated by the MRI unit. The coil 28 can be a quadrature coil in a relatively flexible wrap-around (vest- or jacket-like) configuration (FIG. 4A) with conductors positioned on both the front and back of the chest. Alternately, a semi-rigid or rigid coil configuration is also possible using 'birdcage' geometry, 'phased array' geometries and or parallel imaging geometries. A suitable (prototype) coil is made by Clinical MR Solutions, Brookfield, Wis. In other embodiments, the coil 28 can be a multi-piece (e.g., two-piece) coil that provides the front and back (top and bottom) conductors for signal transmit/receive (Tx/Rx). Different coil sizes may be used for different size patients, e.g., S, M, L, child and the like, each having different radial and/or longitudinal extension and/or fit. Examples of other coil types known to those of skill in the art include a bird cage configuration, a Helmholtz pair, and a phased array.

Embodiments of the present invention use multifrequency imaging, e.g., concurrent $^1H$ and $^{19}F$ imaging. Thus, the system 10 can be configured to scan using $^1H$ imaging either with the body coil 23 (the $^{19}F$ coil 28 can be $^1H$ blocked) or with a two frequency array or other coil and operational arrangement with the lung coil 28 in position. Other embodiments of the present invention can use parallel imaging to improve the speed of acquisition or decrease the specific absorbed radiation (SAR) of the acquisition.

FIG. 1C illustrates that the system 10 can include an interface/gateway 50 with a blocking circuit 50C that can be in communication with the coil 28. The coil 28 is actively proton-blocked to allow $^1H$ imaging through the coil 28 or coil 23 while the coil 28 is in place on the subject. The MR scanner can transmit either 1H or 19F frequencies in one embodiment of the invention and in other embodiments may alternate the frequencies in real time or simultaneously transmit 1H and 19F frequencies for image formation and acquisition. In all embodiments the 19F coil will be statically or dynamically disabled during the 1H transmission.

The interface/gateway 50 can be connected to the coil 28 via lead 27₁ and to a channel associated with the scanner via lead 27₂. The interface/gateway 50 can reside in the control room or in the scan room. The gateway/interface 50 with blocking circuit 50c will be discussed further below.

FIG. 2A illustrates another example of a delivery system 30. As shown, the system 30 includes a pressurized canister 30c with the PFx/O₂ gas mixture 30g. The canister 30c can include a flow regulator 33 and valve 31. The canister 30c can also include a temperature sensor 36 to confirm that the canister 30s has not been exposed to elevated temperatures so that the mixture is suitable for dispensing. The sensor 36 can be a sensor that changes color if exposed to a temperature above the defined threshold (e.g., green is "good" and red is "bad"). The sensor 36 can include or be in communication with an electronic monitor 36m with a power source (such as an on-board battery) that can provide an audio and/or visual alert if the canister 30c has been exposed to an undesired temperature (e.g., a temperature below about 5° C./41° F.). The electronic monitor 36m can also include a circuit that can receive and hold data indicative of the date/time filled and store temperature readings taken at desired intervals, such as, for example, every 10 seconds to every 30 minutes, typically every 1-10 minutes. The electronic monitor 36m can include a circuit with memory that holds the temperature information (and lot number, supplier and/or other relevant gas information) and the memory and/or monitor can form part of the patient record. If, during or after filling the canister 30c with the gas mixture 30g, the canister 30c has been exposed to an undesired temperature, the length and date of the over-exposure can be identified to allow a user to address the shipment/handling issue. In such a situation, the gas cylinder can optionally be warmed to room temperature and 'mixed' by rotation of the cylinder and the concentration checked as previously described by an oxygen sensor 40.

As shown in FIG. 2A, the system 30 can include a conventional Douglas bag arrangement with continuous monitoring of the source gas 30g oxygen level using oxygen analyzer 42 with a pump in fluid communication with a sampling supply line 43 and return line 45. Thus, the system 30 can provide a continuous (circulating) sampling system of the gas mixture 30g.

As shown in FIG. 2A the system 30 can include a flow path 33 with a microbe filter 51 (such as a 0.22 micron millipore filter) residing between an intake-side Douglas bag 55 and a high-efficiency spirometer filter 53. The Douglas bag 55 can be between about 1-200 liters and is typically about a 25 liter bag. The high efficiency spirometer filter can provide low flow resistance and suitable a bacterial & Viral filter, e.g., a bacterial filtration efficiency of about 99.9999%. In this example, the microbe filter is a Cole Parmer, Vernon Hills, Ill., Nylon Sterile Syringe Filters; Pore Size; 0.20, microns Item#: EW-02915-04. The spirometer filter can include a Resp Therapy Filter Item#: MQ 303 from Vacumed, Ventura, Calif. The oxygen analyzer can include the Oxigraf Oxygen Analyzer Item #: 07-0006. The one way valves can be obtained from Vacumed (Item# R5010). The non-rebreathing T-valve can be obtained from Vacumed Item#1464. Other components such as the tubing, Douglas Bags and connectors can also be obtained from Vacumed.

The flow path 33 can also include a mouthpiece 30d in communication with a one-way breathing valve 35. The inhale gas flows into the mouthpiece 30d. The mouthpiece 30d can include or be in communication with a (non-rebreathing) "Y" valve and/or a one-way valve 35 to allow for free-breathing. The system 30 can also optionally include a laser oxygen level sensor 40 (FIGS. 1A-1C) downstream of the spirometer filter 53. The system 30 can also include another (high efficiency) spirometer filter 53 residing downstream of the mouthpiece 30d in communication with the exhale Douglas bag 56 (where used). The exhale-side Douglas bag 56 can be larger than the inhale-side bag 55, typically at least four times as large, such as, for example, about 150 liters. The tubing forming the flow path 33 and the valve 35 and mouthpiece 30d can be single-use disposable.

Figure 2B:
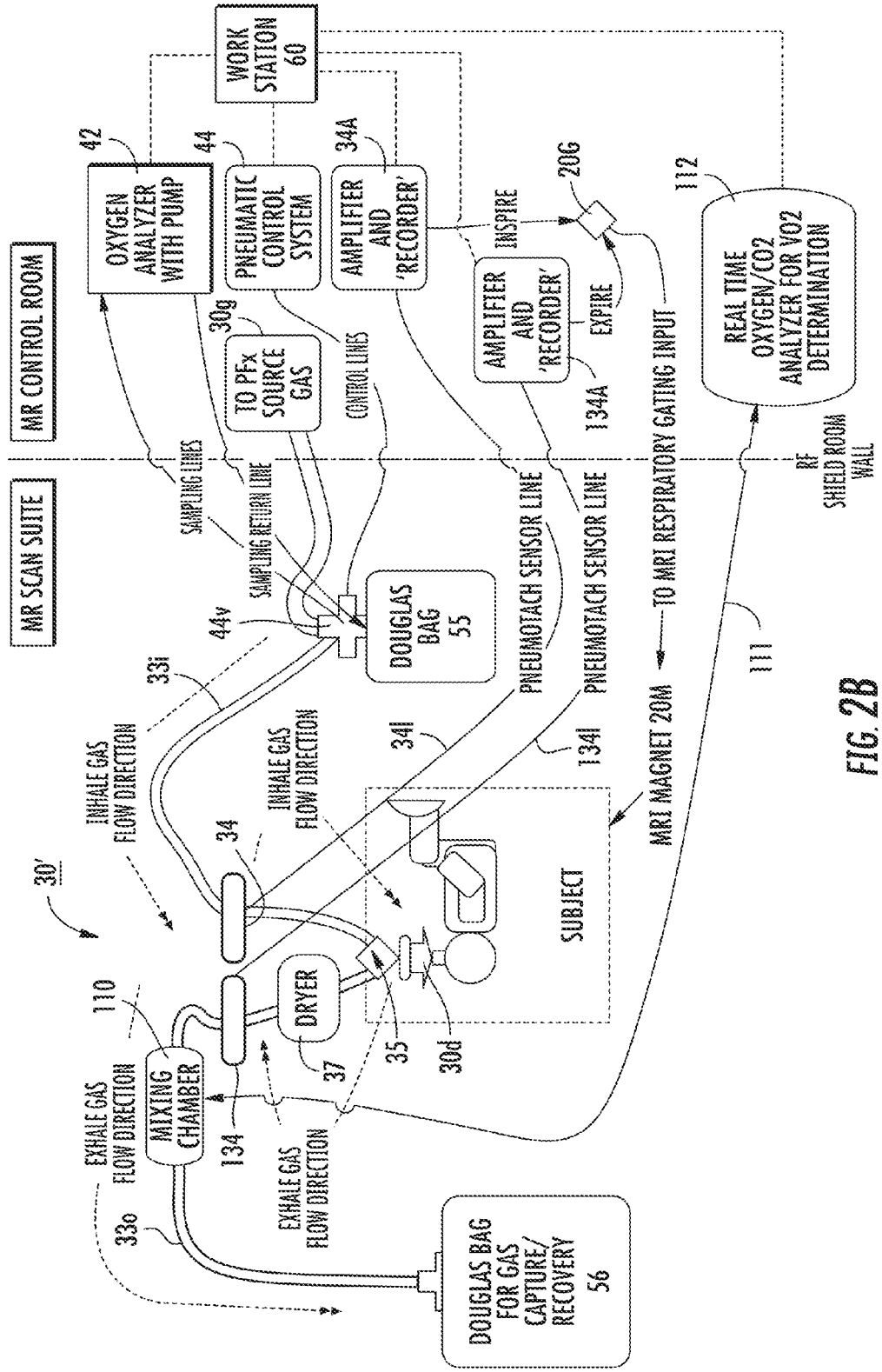
FIG. 2B is a schematic illustration of yet another gas delivery/monitoring system according to embodiments of the present invention.

The system can include a three-way pneumatically controlled valve 44v connected to the pneumatic control 44 in the control room (FIG. 2B).

FIG. 2B illustrates a system 30' similar to that shown in FIG. 2A. Features described with the above system 30 can be included with this system 30' and features described with this system 30' can be used with the above system 30 although not specifically described or shown therewith. Further, not all components shown with either system 30, 30' are required for either one.

The system 30' shown in FIG. 2B can also include an MRI compatible pneumotachometer 34 positioned along the intake flow path 33i with a connecting line 34l extending to an amplifier and data recorder 34A. The amplifier/recorder 34A typically resides in the MR control room but may also reside offsite or even in the magnet room (with proper shielding). The system 30' may also include An MRI compatible pneumotachometer 134 along the outgoing flow path 33o. This pneumotachometer 134 may also include a line 134l that connects to an amplifier/data recorder 134A. Although shown as two pneumotachometers 34, 134, these may be integrated into a single device. The recorder 134A may also reside in the control room but can reside elsewhere (offsite or in the magnet room). A single, typically dual channel, recorder may be used instead of two recorders as shown. The system may include a dryer 37 in fluid communication with and upstream of the outgoing pneumotachometer 134 to dry gas in the expiratory gas flow path. Inspire and expire data from the pneumotachometers 34, 134, typically via the associated recorders 34A, 134A, can be used to provide an MRI respiratory gating input 20G for the gateway interface circuit 50 of the MR Scanner used to obtain MR image signal in a manner that is gated to the respiratory cycle. The pneumotachometers can be Lilly type pneumotachometers.

The system 30' may also include a receiving chamber 110 in fluid communication with the outgoing flow 33o path residing downstream of the pneumotachometer 134 (where used). The chamber 110 can be a "mixing" chamber that collects a desired volume of output gas from the patient. The term "mixing" means that more than one sequential breath is allowed to equilibrate before external sampling of the oxygen and carbon dioxide levels. An alternative is to sample the exhaled gases at the valve 35. The system 30' can include an analyzer 112 that connects 111 to the chamber 110 that analyzes the content of the mixing chamber 110. The analyzer can be a real-time oxygen/CO2 analyzer. The term "real-time" means that the analysis can be carried out within about 1 second or less, typically substantially concurrently with, a measurement or reading at the chamber 110 or valve 35. The analyzer 112 can provide data for VO2 assessment/determination. The analyzer 112 can reside in the MR control room but may also reside remote of the control room or even in the magnet room (with proper shielding).

In some embodiments, a time constant τ for PFx/O2 and room air can be determined or used to calibrate the signal intensity and/or to help define the desired times for obtaining image data for "gas trapping" evaluation. The volume "V" and/or content of the "V inhale and the V exhale can be sampled. Vroom air and V PFx can be established based on interpolations of N2/PFx at different concentrations ($O_2$ sampled, $CO_2$ sampled). For example, for an input of 21% $O_2$ and 79% PFx, the output gas in the chamber 110 downstream of the patient or sampled at valve 35 can be analyzed. In a sample, there can be $O_2$ and $CO_2$, $N_2$ and $H_2O$. The $H_2O$ can be captured in a dryer 37 (weighed over a number of breaths). With the sequential breaths of the PFx mixture, the output gas is 79% Pfx (due to the extremely low solubility in water), oxygen (~14%), $CO_2$ and water. With the water 'trapped' in the drying system 37, it is possible to know the composition of both the input gas mixture (certificate of analysis) and the output gas mixture with the sampling systems so that global exchange of oxygen can be determined. This data can act as a defining factor in the regional analysis of the $^{19}F$ lung images.

Figure 3:
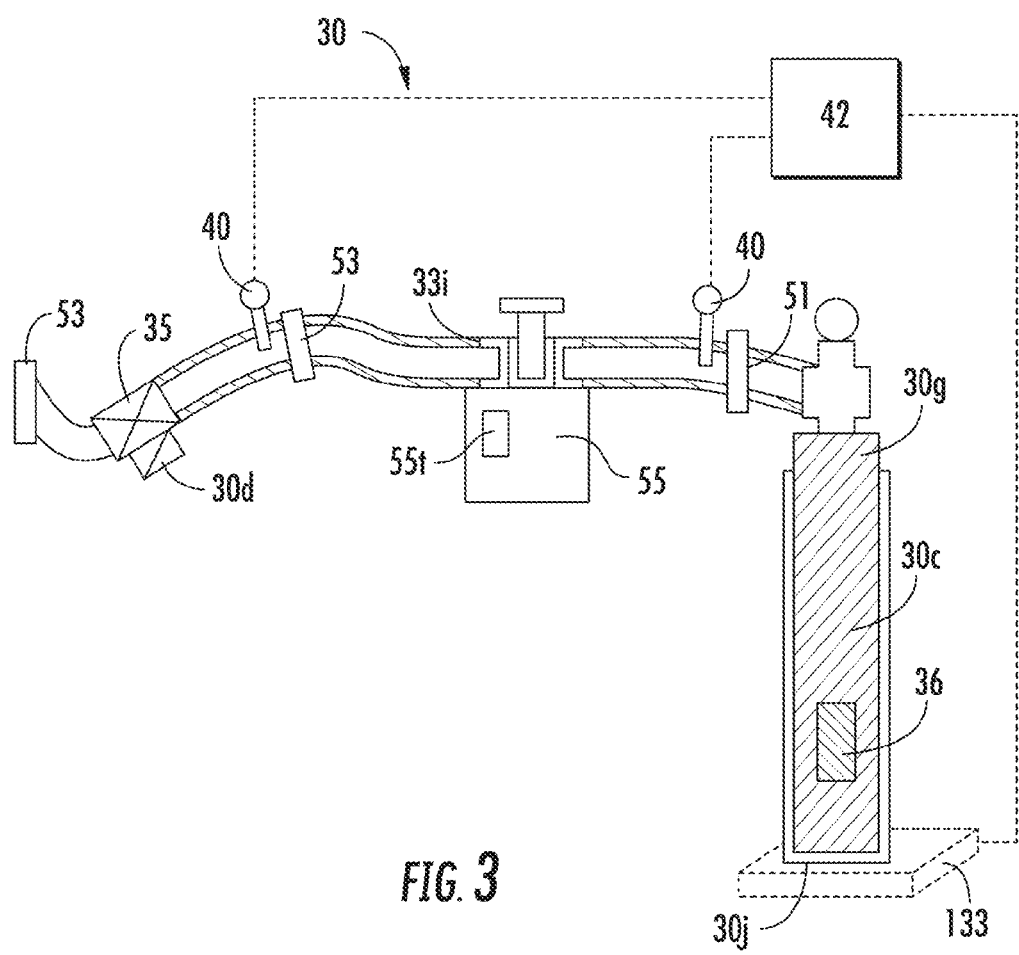
FIG. 3 is a schematic illustration of another exemplary gas delivery system according to embodiments of the present invention.

FIG. 3 illustrates another embodiment of the delivery system 30 and/or further or alternative features that can be used with any of the delivery systems described or illustrated herein.

The system 30 may include a single flexible bag to assist in the passive delivery of the gas 30g, such as a Douglas bag 55. The bag 55 can include a temperature sensor 55t and the system 30 can include a plurality of oxygen sensors 40 of the same or different types to confirm that the oxygen level is at a desired level prior to delivery to a subject/patient.

The system 30 may also optionally include a scale or other weighing device 133 that can communicate with the electronic monitor 42 to alert a user if the supply is below a certain amount, e.g., when less than 5 liters remain, or when below a certain weight corresponding to a low level of the gas mixture. The monitor 42 can be the same monitor as the oxygen monitor or may be a separate monitor.

The pressurized canister 30c of premixed gas 30g can be held in a portable insulated case 33j. The case 33j can include insulation that can help keep the canister above about 10° C./50° F. during transport and/or storage. The case 33j can include a thermometer or other temperatures sensor that communicates with an on-board heat/cool source so as to be temperature controlled. The case can hold a single canister 30c or a plurality of canisters. The canister 30c can hold a single patient bolus supply or multiple-patient bolus amounts. Examples of suitable single patient bolus supplies include about 1-100 liters, typically about 10-25 liters. The electronic monitor 36m (FIG. 2A) and/or 42, where used, can reside inside the case or outside the case. The temperature sensor 36 can be placed inside the case instead of directly on a canister in the case or in addition to individual sensors 36 on each canister 30c. A single monitor 36m can monitor the temperature of all temperature sensors for the respective canisters in the case. The case can optionally include a scale or other weighing device that can communicate with the electronic monitor to alert a user if the supply is below a certain amount, e.g., when less than about 10% of the "full" weight remains. Alternately a pressure sensor sampling at 35 can also detect a empty delivery bag at 55. Each canister 30c in the case can be in communication with such a scale or a single "dispensing" position in the case can include the scale and the canister 30c in active use can be placed in this position for capacity/level sensing so that the delivery of the gas mixture 30g during a procedure is not disrupted by an inadvertent "empty" gas source.

Figure 4A:
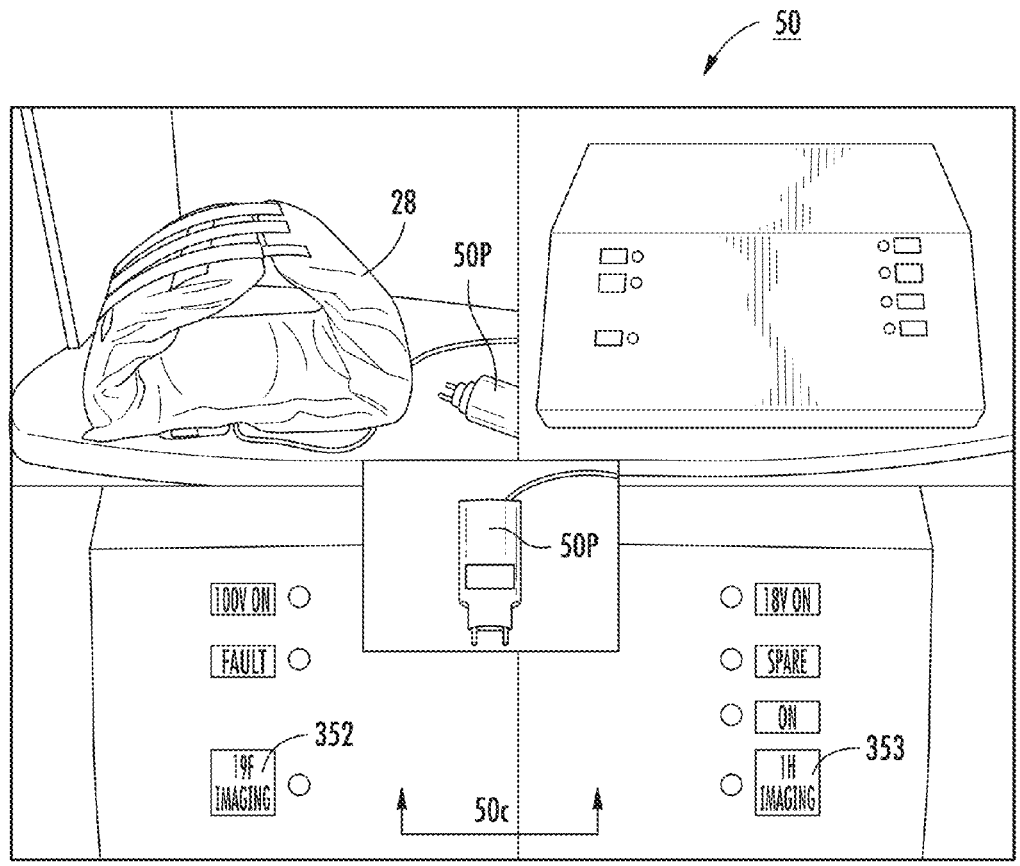
FIG. 4A is an illustration of a lung imaging coil jacket in communication with a gateway interface and blocking network power supply according to embodiments of the present invention.

FIG. 4A illustrates that the interface/gateway 50 can also include a power supply 50P and two operational modes 352, 353 as shown in FIG. 4A. The gateway/interface 50 can include safety indicators for the blocking circuit 50C as shown in FIG. 4A. The lung (also known as "chest") coil can be configured to be "proton-blocked" allowing the MR scanner body coil to be used to make a proton image of the subject in substantially the same position as the subject during the $^{19}F$ image. Thus, the proton blocked chest coil allows the body coil to obtain supplemental proton-based data image (without the interference of the $^{19}F$ coil) which can be combined in a signal processor to provide a more detailed diagnostic evaluation of the target region of interest. The blocking circuit can be of a passive crossed diode design, active pin diode design or combination design. The purpose of the blocking circuitry when activated is to provide a high impedance at the 1H frequency. Indicators on the blocking circuit power supply include general power (110V) available, blocking voltage (100 V reverse bias or −100 V) available during 1H transmit and blocking voltage disabled (10 V forward bias or +10 V) during 19F transmit. The coil 28 and the interface/gateway 50 can be used with all other embodiments of the invention.

FIG. 4A also illustrates that the coil 28 can be a relatively flexible wrap-around vest- or jacket-like coil with conductors positioned on both the front and back of the chest. The rectangular dimensions can be about 30-40 cm by about 110-140 cm to give nominal coverage of about 38-40 cm diameter which may be particularly suitable for most adult patients.

For a 3.0 T system, the $^1H$ resonance is nominally 123-128 MHz while the $^{19}F$ resonance is about 115 MHz. These frequencies are relatively close. Thus, as discussed above the coil 28 can be proton blocked to allow $^1H$ imaging while the subject S is in the scanner 20M. The interface/gateway 50 can be configured to allow a user to manually select and/or the system 10 to electronically select either a $^1H$ imaging mode or a $^{19}F$ imaging mode.

During at least a portion of the imaging session, before, after or during delivery of the gas mixture 30g, the body coil 23 can collect $^1H$ signal while the lung coil 28 collects $^{19}F$ signal, thus allowing substantially concurrent, generally simultaneous, $^1H$ imaging with $^{19}F$ imaging. It is also contemplated that two frequency array coil can be used to obtain the two different frequency image data signals concurrently.

Figure 22:
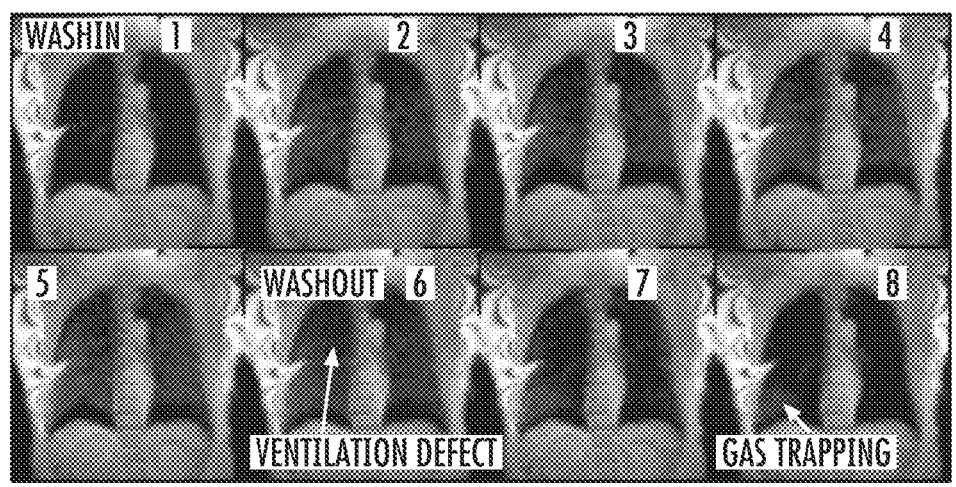
FIG. 22 is a set of images taken at sequential times (and incremental gas dose) for wash-in kinetic analysis of ventilation defect severity followed by wash-out after switching to room air.

The system 10 can be configured to transmit and receive excitation pulses at both the $^1H$ and $^{19}F$ resonances during a single imaging session and acquire image data signals using the body coil 23 and the lung coil 28. To evaluate "wash in", "wash out" or other ventilation information, the $^{19}F$ imaging can continue for a plurality of respiratory cycles before, during and/or after the gas mixture 30g delivery, while the patient breathes room air. For a "wash out" cycle from saturation of the gas mixture in the lungs, the wash out cycle can be carried out for as long as there is detectable $^{19}F$ signal, which is believed to be between about 2-10 respiratory cycles in duration. The air breathing intake imaging with $^{19}F$ in lung spaces/tissue may allow gas trapping evaluation in both a regional and temporal manner. Examples of such images are shown in FIG. 22.

The system 10 can be configured to generate cine images of the lungs and lung spaces/airways. The cine images can be gated to the respiratory cycle. Gated imaging techniques are known. See, e.g., U.S. Patent Application Publication No. 2008/0132778, the contents of which are hereby incorporated by reference as if recited in full herein.

Figure 4B:
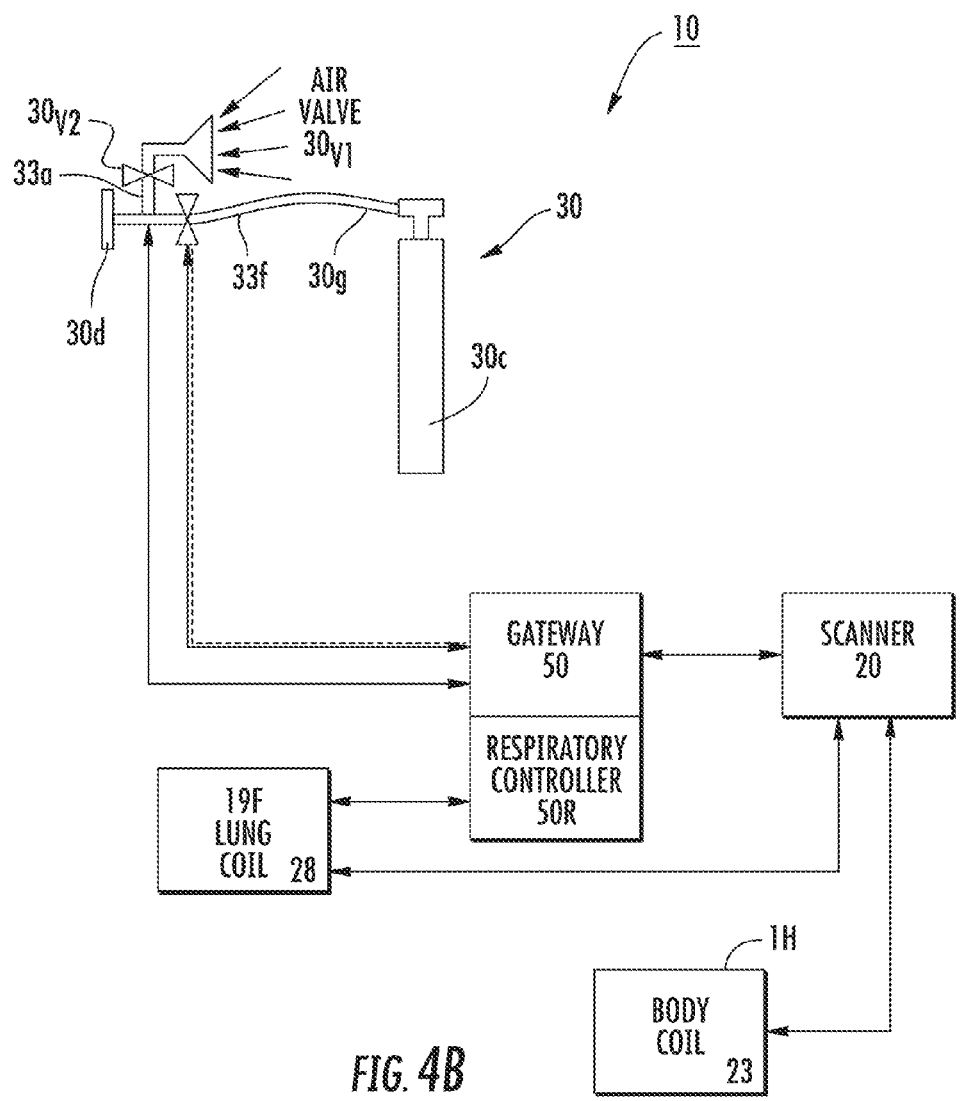
FIG. 4B is a schematic illustration of an imaging system that can temporally switch between the PFx and O2 gas mixture delivery and alternate gas delivery (e.g. room air, 100% O2, etc) according to embodiments of the present invention.

As shown in FIG. 4B, the system 10 can include an automated cycling system that electronically controls the gas delivery system 30 using, for example, a valve 30v, located proximate the patient to close the flow path 33f and a valve 30$v_2$ residing between the air intake and the mask or mouthpiece 30d to open the air flow path 33a to allow the patient to breathe air during a portion of the imaging session. Typically, the patient will breathe normal room air for the first 1-5 minutes with $^1$H MRI Tx/Rx operation. The patient will then be changed over to the gas mixture 30g for 1-10 minutes, then switched back to room air, during which time $^{19}$F signal can be obtained. The system 10 can then close the air flow path 33a and open the gas flow path 33f to deliver the PFx gas mixture 30g. The dispensing member (e.g., mask, nasal input or mouthpiece) can also be associated with a (one-way and/or "Y") valve 55 that directs the exhaled room air or gas mixture to a downstream container such as a bag which can be a Douglas bag 56 (FIG. 2A, 2B).

As shown in FIG. 4B, the gateway/interface 50 can include a respiration controller 50R that electronically controls the opening and closing of the valves 30$v_1$, 30$v_2$ during the imaging session. However, the valves may also or alternatively allow for manual operation. However, the air to gas mixture controller 50R can be a separate circuit in a different device and can, for example, be interfaced to the scanner 20 or a dedicated workstation.

The use of medical grade inert PFx gas and oxygen gas mixtures as imaging agents during MRI can provide regional ventilation information. The PFx gas attains a relatively high thermal polarization exceptionally quickly which coupled with the large $^{19}$F MR signal, allowing for imaging ventilation with a quality similar to that of hyperpolarized $^{129}$Xe MRI, but at lower cost and with reduced technical complexity. Additional parameters such as 'gas trapping', 'wash-in' and 'wash-out' time/dose curves and ventilation defect severity can be determined with these mixtures. Oxygen extraction can be indirectly determined from images obtained proximal to inspiration and compared to images >2 seconds post inspiration.

The scanner 20 can be configured to employ suitable MRI pulse sequences, including, for example, a gradient echo sequence in both or either 2D and 3D modes, such as a GRE (gradient recalled echo) sequence and the GRE VIBE (Volume Interpolated Breath hold Examination) sequence modified for very fast imaging. Both of these pulse sequences allow physiologic gating and standard imaging modes which allow for washout measurements of regional ventilation. The currently contemplated imaging methodologies do not have extraneous background signal, thus allowing the use of non-selective excitations and extremely short echo times (TE) on the order of about 500 microseconds (μs) at high pixel bandwidths (BW) of about 1500 Hz/pixel (appropriate for SF6) and a lower BW of about 200 Hz/pixel with a TE of about 0.8-1.2 milliseconds (ms) for PFP (because of the longer T2 and T2* for this agent). A 3D image (5 mm in-plane resolution and 15 mm slices) can be sampled in a few seconds, which allows a full 3-D volumetric reconstruction. Voxel dimensions can be any suitable volumes but are typically 5 mm in-plane and 10-20 mm slices. However, it is also contemplated that alternate or optimized pulse sequences will be developed for use with the PFx gas mixtures in the future.

The pulse sequence can be generated to use a suitable flip angle to obtain the signal data of the target gas. FIGS. 5A-5C illustrate examples of signal plots (signal versus flip angle) for TR=10 ms and TE=1 ms (TR refers to the repetition time and TE refers to echo time). For lung parenchyma (FIG. 5A), the T1 is about 1200 ms, and T2* is about 1.8 ms. As shown in FIG. 5B, for SF6, T1=2 ms and T2*=1 ms. As shown in FIG. 5C, for PFP, T1=20 ms, T2*=10 ms. T1 is the decay time constant (T1) corresponding to the gas polarization life and T2* is a transverse relaxation time.

Figure 6:
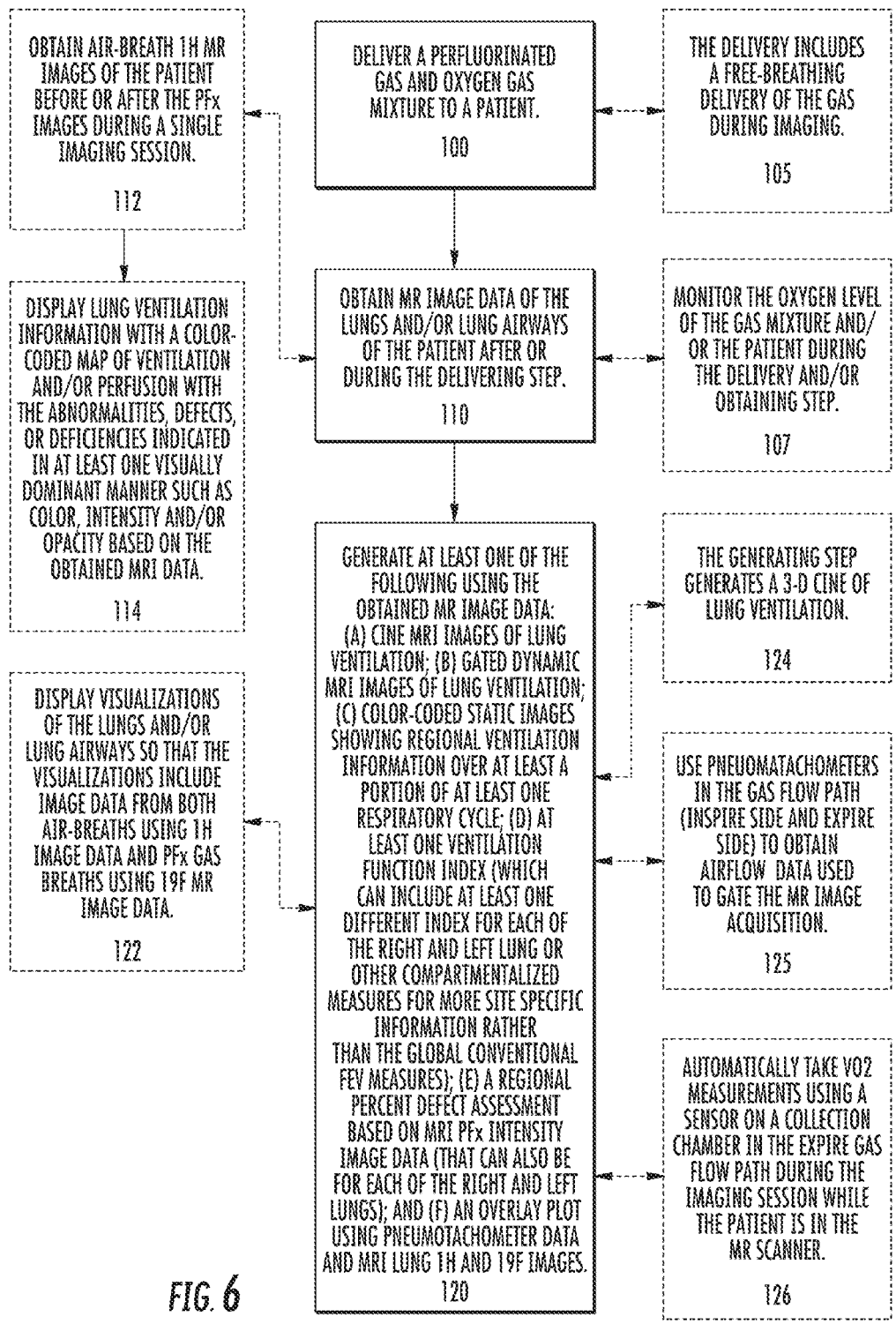
FIG. 6 is a flow chart of operational steps that can be used to carry out embodiments of the present invention.

FIG. 6 illustrates exemplary operations that can be used to carry out methods contemplated by embodiments of the present invention. A perfluorinated gas and oxygen gas mixture is administered/delivered to a patient (block 100). Optionally, the delivery is a free-breathing delivery of the gas mixture during the image data acquisition (block 105) (note that step 105 could breath-held, free breathing or paced breathing where pacing could be accomplished with a visual or aural (tone) for the subject to match their breathing pattern). MR image data of the lungs and/or lung airways of the patient are obtained during and/or after the delivering step (block 110). At least one of the following is generated using the obtained MR image data: (a) Cine MRI images of lung ventilation; (b) gated dynamic MRI images of lung ventilation; and (c) color-coded static images showing regional ventilation information over at least a portion of at least one respiratory cycle; (d) at least one ventilation function index (which can include at least one different index for each of the right and left lung or other compartmentalized measures for more site-specific information rather than the global conventional FEV measures); (e) a regional percent defect assessment based on MRI PFx (intensity) image data (that can also be for each of the right and left lungs); and (f) an overlay plot using pneumotachometer data and MRI lung 1H and 19F images (block 120). The system may also be configured to display or provide FEV1 measures using both oxygen and the PFx gas used for the MRI images. It is contemplated that pulmonologists may be able to interpret the new data better if conventional FEV1 measures are provided as a "baseline" or reference information (at least while the new technology is initially clinically implemented to facilitate clinician acceptance and understanding of the new measures of ventilation defects).

In some embodiments, the generating step generates a 3-D cine of lung function/ventilation (typically including image data collected based on free-breathing of the PFx and O2 gas mixture) (block 124). The cine images may be gated to the respiratory cycle and obtained over a plurality of breathing cycles using signal averaging.

Optionally, the method can also include the step of monitoring the oxygen level of the gas mixture and/or the patient during the delivery and/or obtaining step (block 107).

Optionally, but typically, air-breath $^1$H MR images of the patient are obtained before or after the PFx images during a single imaging session (block 112). This can be performed to include "wash in" and "wash out periods" which may provide gas trapping or other ventilation defect information. See, e.g., FIGS. 15-19, 22 and 23. Optionally, lung ventilation information is displayed with a color-coded map of ventilation and/or perfusion with the abnormalities, defects, or deficiencies indicated in at least one visually dominant manner such as color, intensity and/or opacity based on the obtained MRI data (block 114).

Optionally, visualizations of the lungs and/or lung airways are displayed so that the visualizations include image data from both air-breaths using $^1$H image data and PFx gas breaths using $^{19}$F MR image data (block 122).

The static and/or dynamic ventilation images can be based on fused images of registered $^1$H image data and $^{19}$F image data obtained concurrently during a single imaging session.

The systems can include pneuomtachometers in the gas flow path (inspire side and expire side) that ca be used to obtain airflow data used to gate the MR image acquisition (block 125). The systems/methods can be configured to automatically take VO2 measurements using a sensor on a collection chamber in the expire gas flow path during the imaging session while the patient is in the MR Scanner (block 126).

In some embodiments, baseline ventilation images can be electronically compared to ventilation images taken during or after treatment with a therapeutic agent to analyze effect on lung function. The electronic comparison can be based on intensity differences of spatially correlated imaging data or changes in gas trapping function of the lung and the like.

Generally stated, in some embodiments, a patient is positioned in a bore of an MRI scanner magnet 20M and exposed to a magnetic field. As is well known to those of skill in the art, the MRI scanner 20 typically includes a super-conducting magnet 20M, gradient coils (with associated power supplies), a body and/or surface coil (transmit/receive RF coil), and a RF amplifier for generating RF pulses set at predetermined frequencies. The RF pulse(s) is transmitted to the patient with a defined pulse sequence and flip angle(s) to excite the target nuclei. The body 23 and surface (lung) coil 28 are each tuned to a different selected frequency range to transmit the excitation pulses and to receive signal in response to the TX pulse sequence generated by the MRI unit.

The patient inhales a quantity of the PFx/O2 gas mixture into the pulmonary region (i.e., lungs and trachea). After inhalation, the patient can hold his or her breath for a predetermined time such as 5-20 seconds. This can be described as a "breath-hold" delivery. However, in other embodiments, the patient can freely inhale the PFx/O2 gas mixture during the image session and signal acquisition.

During or shortly after inhalation of a suitable amount of gas mixture, the MRI scanner delivers a desired pulse sequence typically with a large flip angle, such as, for example, a flip angle of about 40 degrees for PFP and a TR of 5 ms. As used herein, the term "large flip angle" refers to a flip angle which is greater than about 30 degrees and up to 90 degrees.

The patient can then freely breathe air from the room and additional $^{19}F$ signal can be obtained during additional respiratory cycles. The dissipation or trapping of the signal can be evaluated to assess regional or global measures of ventilation.

Figure 15:
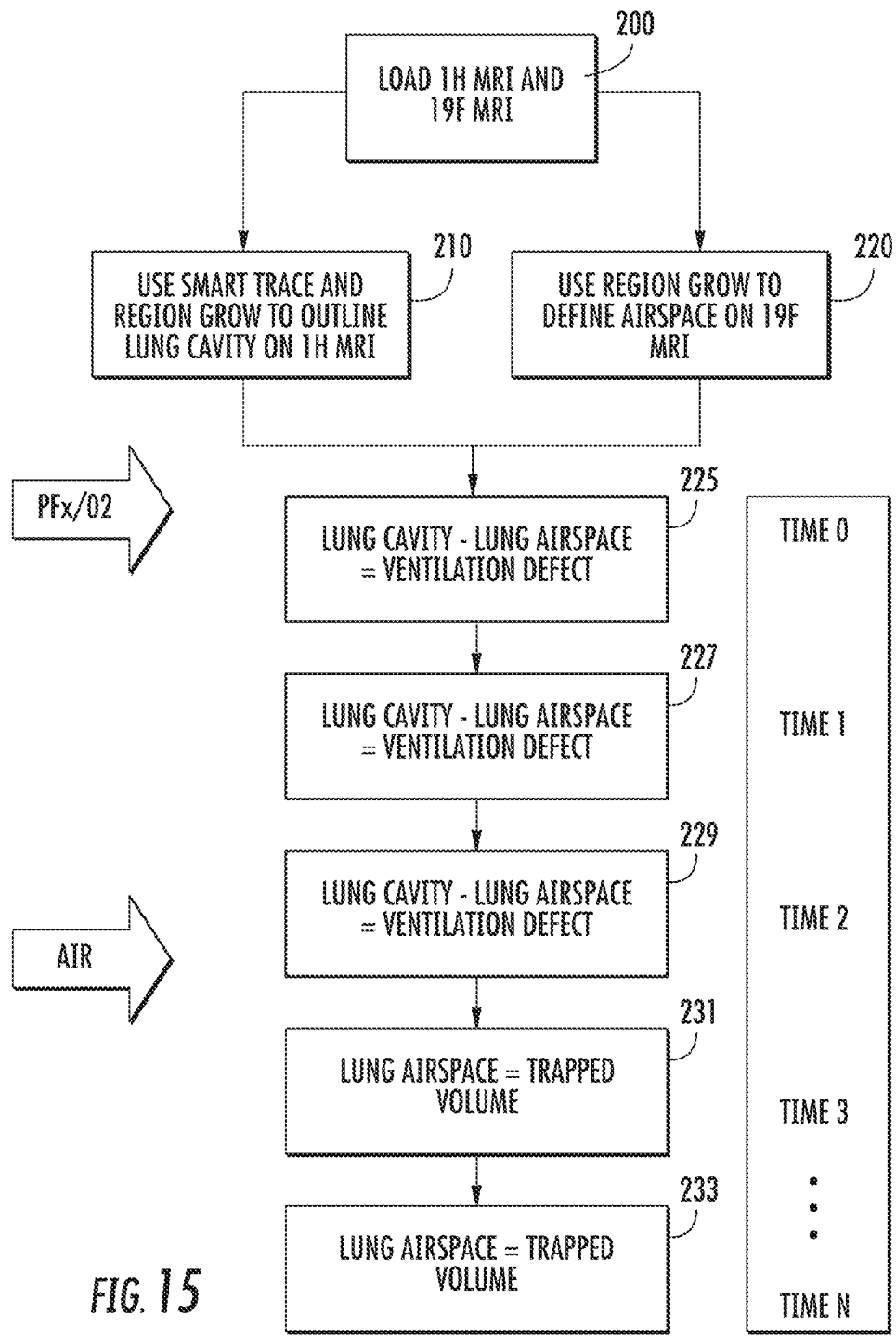
FIG. 15 is a flow chart of exemplary image analysis steps that can be used to identify ventilation defects and trapped gas volume according to embodiments of the present invention.

FIG. 15 illustrates a series of steps that can be carried out along a time line to obtain different MRI signal data using both 1H and 19F MRI. As shown, the MR Scanner can be loaded (e.g., activated or selected to run) with 1H and 19F protocols (coils, pulse sequences, gating, etc. . . . ) (block 200). A smart trace and region grow algorithm can be used to outline a lung cavity or cavities using 1H MRI (block 210). The region grow algorithm can be used to define the airspace(s) using 19F MRI (block 220). An example time course is set out at the right side margin, from time t=0 which is set to match the delivery of PFx/O2 gas to time N, which is a few breath cycles after the cessation of the PFx gas/O2 mixture and the intake of air (which is shown at time t=2). During the time sequence, MRI image data can be obtained. At time t=0 to t=2, during a "wash in" period of PFx gas to an equilibrium or saturation period (t=2), image data is obtained (including images and/or cine images). The previously defined lung cavity outline and airspace regions can be used. The image data can be used to show a ventilation defect, by subtracting the lung airspace from the lung cavity (blocks 225, 227, 229). The PFx gas/O$_2$ mixture can be shut off and the patient can intake air (t=3). Image data can be obtained during the "wash out" period times t=3 to t=n. The trapped volume of gas can be defined based on the lung airspace images (blocks 231, 233).

Figure 16:
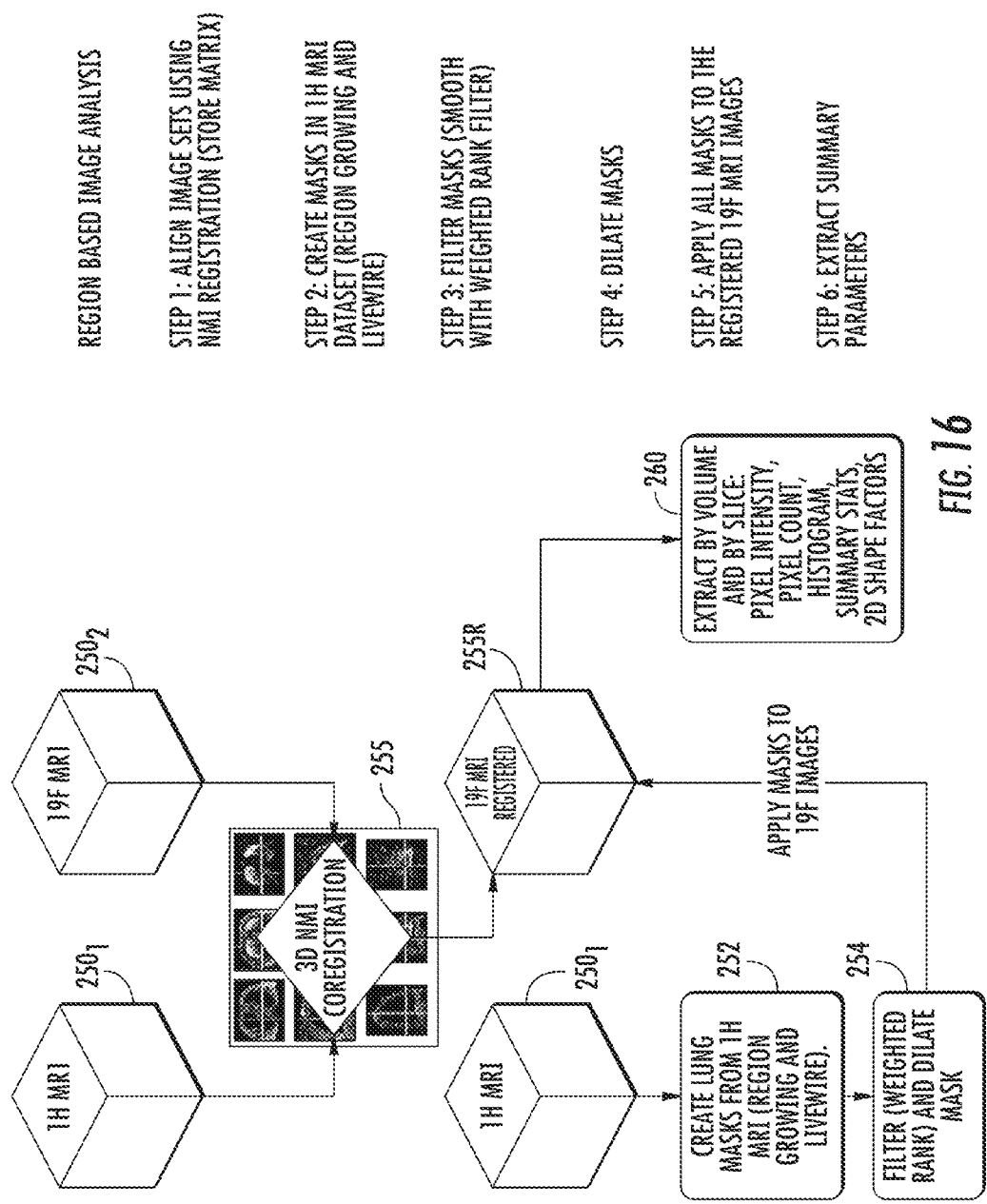
FIG. 16 is a schematic illustration of an image analysis protocol that can be used to identify ventilation defects or abnormalities using extracted summary parameters according to embodiments of the present invention.

FIG. 16 is a schematic illustration of region based image analysis using both 1H and 19F (registered) MRI image data. As shown, two image data sets are obtained, one 1H MRI data set $250_1$ and one 19F MRI data set $250_2$. The two image sets are aligned using, for example, 3-D normalized mutual information co-registration (block 255). This matrix can be electronically stored for future use. Lung masks can be created using the 1H MRI data set $250_1$, the masks can be created using Region Growing and LiveWire or other suitable algorithms (block 252). {Examples of such algorithms are described in numerous texts, for example, in "Handbook of Medical Imaging: Processing and Analysis", Isaac N Bankman, Ed., Academic Press, 2000} The masks can be filtered (e.g., weighted rank) and optionally dilated (block 254). These masks can be applied to the registered 19F images 255R (e.g., NMI co-registered 19F image data). Summary parameters can be extracted from the 19F MRI image data using the applied masks (block 260). Summary parameters can be extracted by volume and/or slice, including, for example, pixel intensity, pixel count, histogram, summary statistics, 2D shape factors and the like. The term "summary statistics" includes, for example, mean, variance, range, etc. and the term "2-D shape factors" includes, for example, centroids, pixel weighted centroids, etc.

FIGS. 17A and 17B are tables of summary parameter data that is generated for one volume and a plurality of slices. The ventilation defect score (or "index") for FIG. 17A is 39 while that for FIG. 17B is 116. The ventilation defect score can be determined by calculating the centroid in each slice as well as the image pixel intensity weighted centroid in each slice. By summing the difference (x and y positions) of these parameters, a volume displacement score can be obtained. For instance, if the image is homogeneous in intensity the ventilation defect score ("VDS") would be zero. Larger values of the VDS give a single global index of inhomogeneous image intensity.

Figure 18:
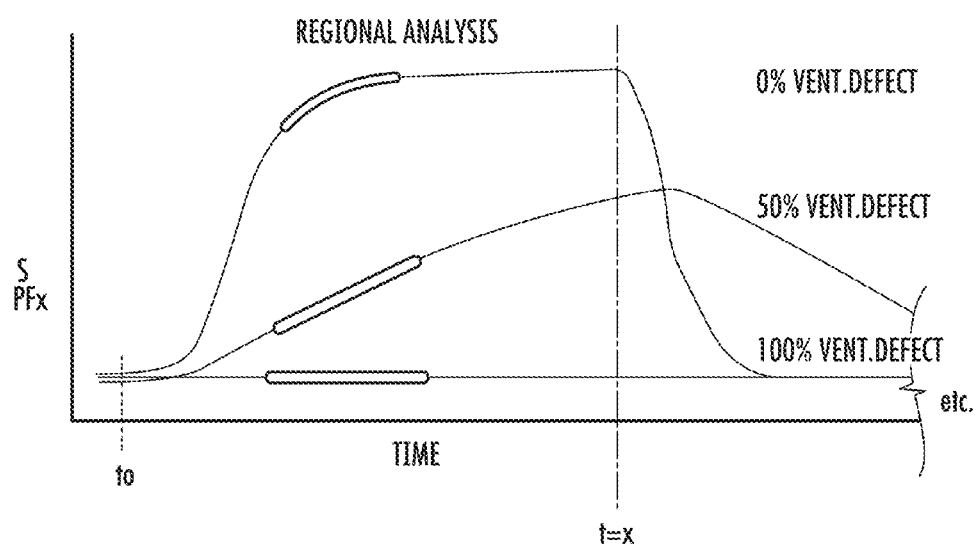
FIG. 18 is a graph of PFx signal over time for regional analysis of ventilation defects according to embodiments of the present invention.

FIG. 18 illustrates a regional analysis using data from a graph of $^{19}F$ PFx signal "S" over time of the PFx gas. At a defined time (t=x), a ventilation defect can be identified based on a defined range or threshold value. This defect can be based on the value at the defined time (or ranges of values), and/or may include the slope or area under the curve of a respective line. As shown, a substantially flat line from t=0 to t=x can indicate a major ventilation defect (shown as 100%) while the upper line with the larger value at time t=x indicates no ventilation defect. The intermediate line indicates a decrease in function, shown as a 50% ventilation defect. In practice, the time can incorporate a few hundred seconds of image acquisition of a temporal array of data (e.g., FIG. 22) and the ventilation defects can rank based on regions that show asymptotic local signal maxima (no ventilation defect).

Figure 19:
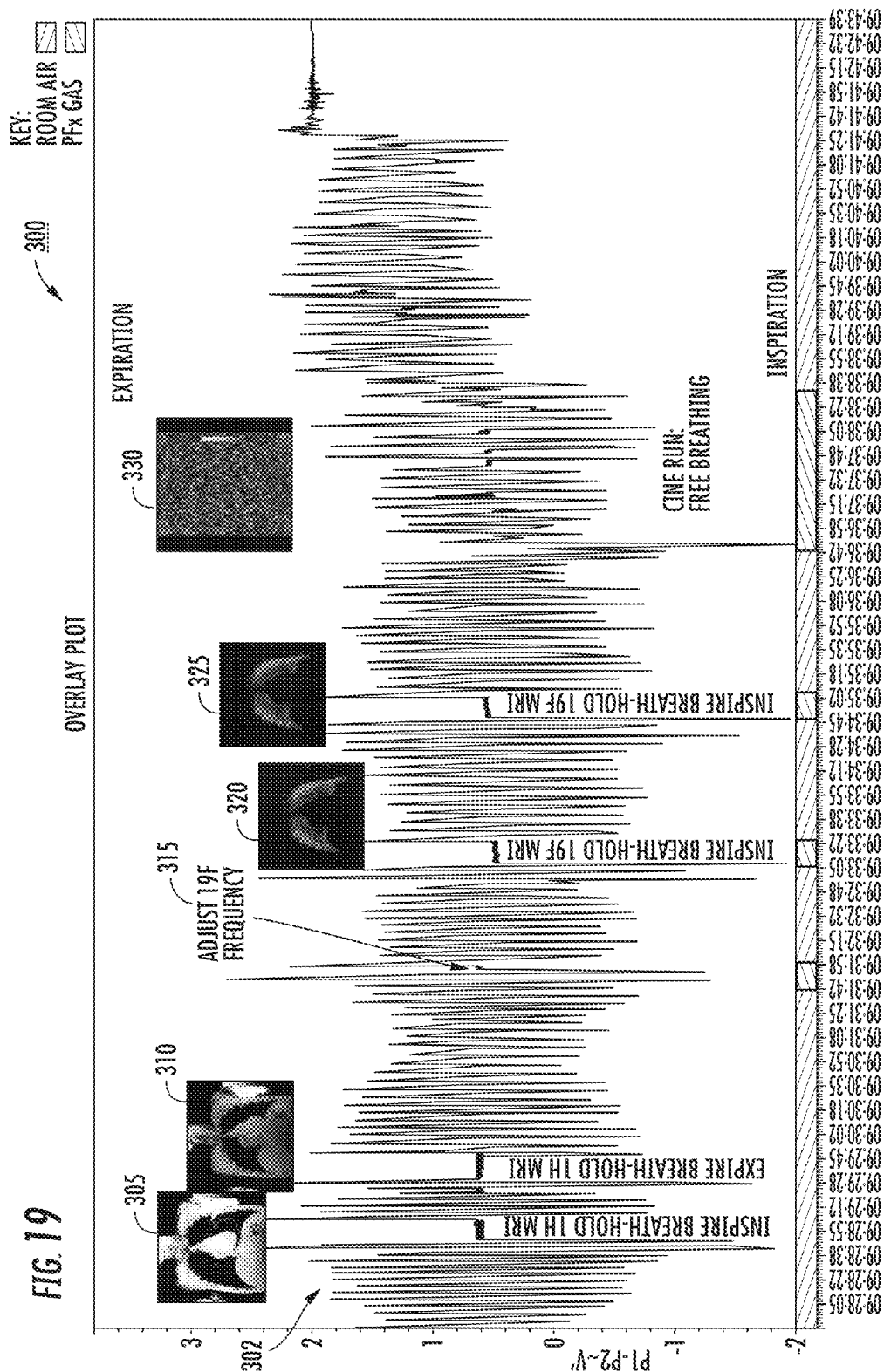
FIG. 19 is a screen shot of an example of a overlay plot of pneumotachometer output over time with interposed MRI images at noted timelines according to embodiments of the present invention.

FIG. 19 illustrates an example of an overlay plot or output display that can be provided to a clinician at a local worksite or a remote station. The display includes a time line of airflow data of the patient 302 using at least one pneumotachometer with an overlay of MRI images, including one or more of images 305, 310, 320, 325, 330, taken at a corresponding time during the recording (with both air and PFx gas intake). The images can be thumbnail images that are shown over the airflow data or may be provided in an adjacent panel or windows. A UI associated with a display that shows the overlay plot 300 can be configured to allow a user to select one image to enlarge it on the overlay or in a separate window for ease of viewing.

Air flow rate is determined directly from the calibrated pneumotachometer 34 and volume is determined by integrating air flow with respect to time. In practice, as the data is digitized the trapezoidal rule applies.

For example, as shown inspire and expire breath hold normal air 1H images, can be shown proximate to the time during the breath hold reflected by the airflow timeline. The inspire image can be before or after the expire image. The MRI frequency can be adjusted and may be marked on the overlay 300 as shown by text reference 315 (but arrows, different colors, or other indicia may also or alternatively be used). Inspire and Expire breath hold 19F MRI images may be obtained 320, 325 over sequential or non-sequential breatholds (FIG. 22, shows 8 sequential breathholds) and shown on the overlay plot 300. A cine run of MR images 330 during free breathing of the PFx gas/$O_2$ mixture can be obtained and also shown or be accessible via a thumbnail and/or viewing panel or window on the display shown as on the overlay plot 300.

Figure 20B:
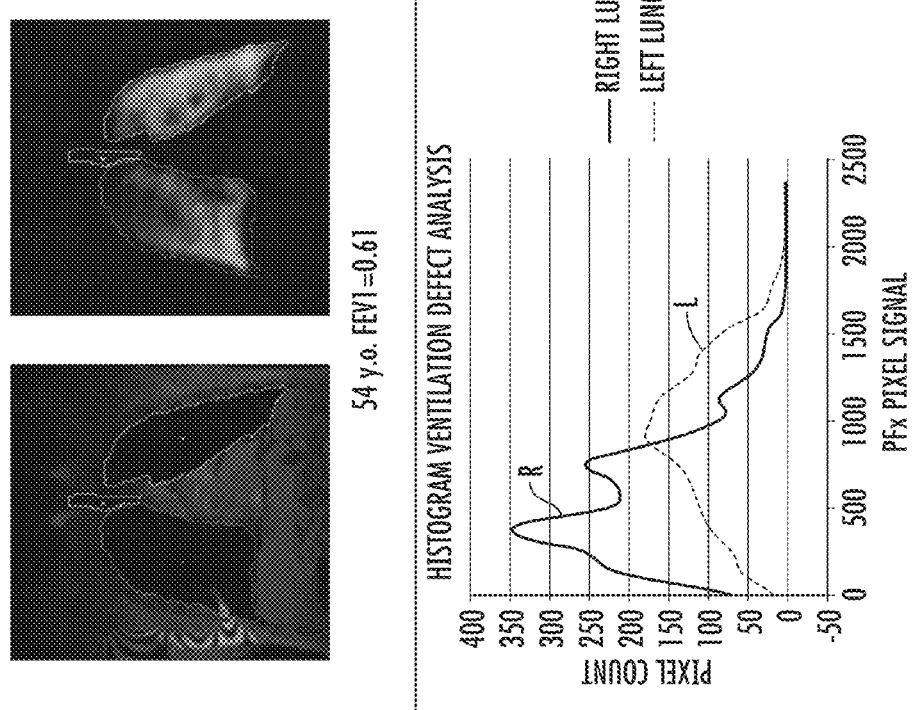
FIGS. 20A and 20B are images and associated graphs of pixel count versus PFx pixel intensity using a histogram ventilation defect analysis for different patients according to embodiments of the present invention. Notably, both of the patients have substantially the same FEV1 value but different defects.
Figure 20A:
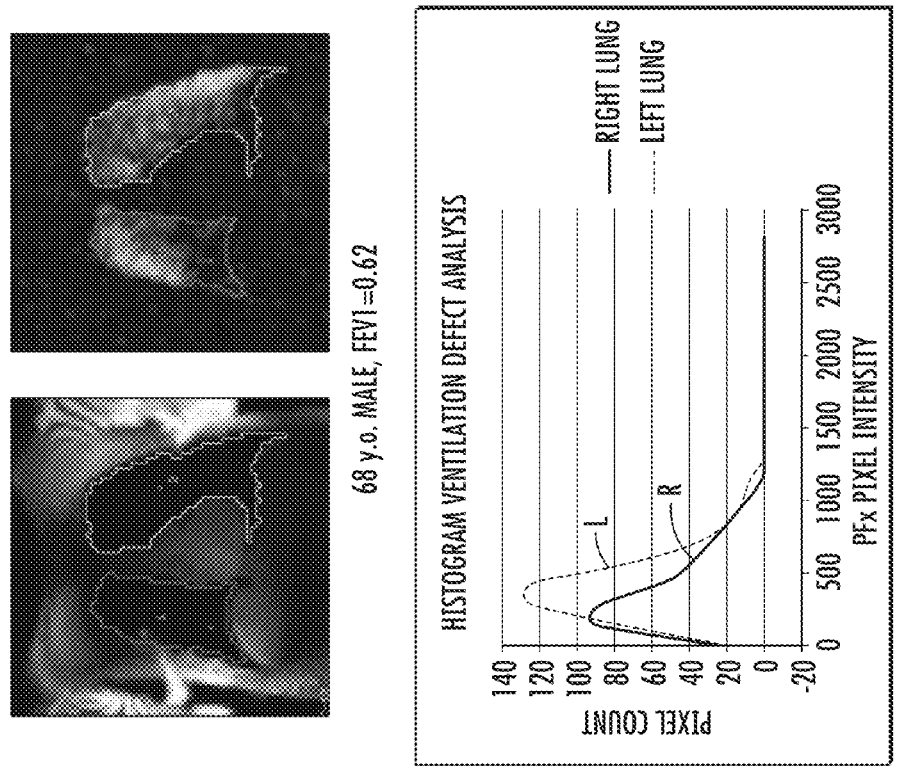

FIGS. 20A and 20B illustrate a respective graph of pixel count versus PFx pixel intensity for each of a right and left lung of two different patients. While the PEV1 of each patient is almost exactly the same, the one of the left is an FEV1 of 0.62 for a 68 year old while the one on the right is 0.61 for a 54 year old, the histogram ventilation defect analysis shows a large defect difference.

Certain embodiments are directed to generating a ventilation defect alpha numeric or numeric index that can be used to facilitate clinician and patient understanding or use of the PFx image data. The index can be right and left lung specific, e.g., an index for each lung of a patient such as R-10 (large right lung ventilation defect) and L-3 (lesser ventilation defect in the left lung).

Figure 21:
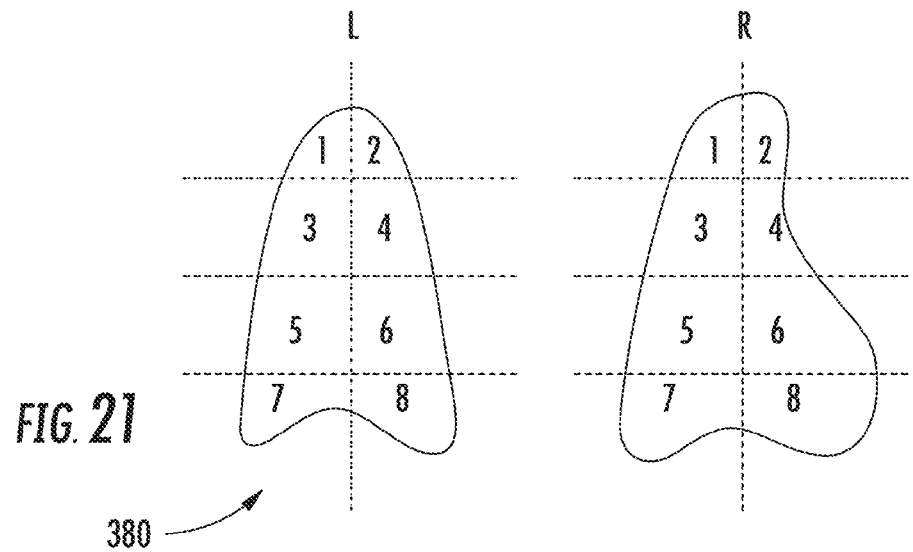
FIG. 21 is a schematic of a standardized compartment model of the lungs that can be used to identify lung ventilation defect indexes for different patients according to embodiments of the present invention.

The index can be provided as a series of indices for each lung based on a standardized compartmentalized model of the lung. An example of a compartmentalized model 380 of the lungs is shown in FIG. 21. The model can be a quadrant or other multi-compartment 2-D or 3-D model based on the PFx/$O_2$ gas MRI pixel signal. Each compartment of the model can be evaluated and/or populated using pixel intensity data and assigned an index that is provided on a scale that represents a low or no ventilation defect to a major or total ventilation defect. The scale can go from low to high or high to low. For example, the model can have between 1-20 compartments and a patient can have an associated number of measures, e.g., for twelve compartments each compartment can have a defined associated identifier such as R1-R12 (right lung) and L1-L12 (left lung), with each having an associated measure of ventilation defect, e.g., from 0-10 or 0-100 and the like. This same data can be provided in a visual "virtual" lung model or as a data set for a clinician to use. It is contemplated that a more regionalized quantitative assessment of ventilation defects can help treat or track disease progression relative to the global FEV1 measure currently used. The index or indices can be provided along with conventional FEV1 measures to facilitate clinician acceptance or use (and allow the clinician some historical evaluation information that may be helpful when deciding on a therapeutic course of action).

The index can be provided as an integrated index (e.g., alphanumerical or numerical) which indicates the defect rating in each defined region or as a global lung index (typically, at least one per lung). The indexes can be provided as a ventilation defect index map showing a spatial distribution (pixel wise) of the lungs. The distribution can be based on histogram data or other image signal data associated with 19F at equilibrium and/or wash-in and/or wash-out.

Embodiments of the present invention may take the form of an entirely software embodiment or (more likely) an embodiment combining software and hardware aspects, all generally referred to herein as a "circuit" or "module." Furthermore, the present invention may take the form of a computer program product on a computer-usable storage medium having computer-usable program code embodied in the medium. Any suitable computer readable medium may be utilized including hard disks, CD-ROMs, optical storage devices, a transmission media such as those supporting the Internet or an intranet, or magnetic storage devices. Some circuits, modules or routines may be written in assembly language or even micro-code to enhance performance and/or memory usage. It will be further appreciated that the functionality of any or all of the program modules may also be implemented using discrete hardware components, one or more application specific integrated circuits (ASICs), or a programmed digital signal processor or microcontroller. Embodiments of the present invention are not limited to a particular programming language.

Computer program code for carrying out operations of the present invention may be written in an object oriented programming language such as Java®, Smalltalk or C++. However, the computer program code for carrying out operations of the present invention may also be written in conventional procedural programming languages, such as the "C" programming language. The program code may execute entirely on the user's computer, partly on the user's computer, as a stand-alone software package, partly on the user's computer and partly on another computer, local and/or remote or entirely on the other local or remote computer. In the latter scenario, the other local or remote computer may be connected to the user's computer through a local area network (LAN) or a wide area network (WAN), or the connection may be made to an external computer (for example, through the Internet using an Internet Service Provider).

The present invention is described herein, in part, with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer-readable memory that can direct a computer or other programmable data processing apparatus to function in a particular manner, such that the instructions stored in the computer-readable memory produce an article of manufacture including instruction means which implement the function/act specified in the flowchart and/or block diagram block or blocks.

The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide steps for implementing some or all of the functions/acts specified in the flowchart and/or block diagram block or blocks.

The flowcharts and block diagrams of certain of the figures herein illustrate exemplary architecture, functionality, and operation of possible implementations of embodiments of the present invention. In this regard, each block in the flow charts or block diagrams represents a module, segment, or portion of code, which comprises one or more executable instructions for implementing the specified logical function(s). It should also be noted that in some alternative implementations, the functions noted in the blocks may occur out of the order noted in the figures. For example, two blocks shown in succession may in fact be executed substantially concurrently or the blocks may sometimes be executed in the reverse order or two or more blocks may be combined, depending upon the functionality involved.

Figure 7:
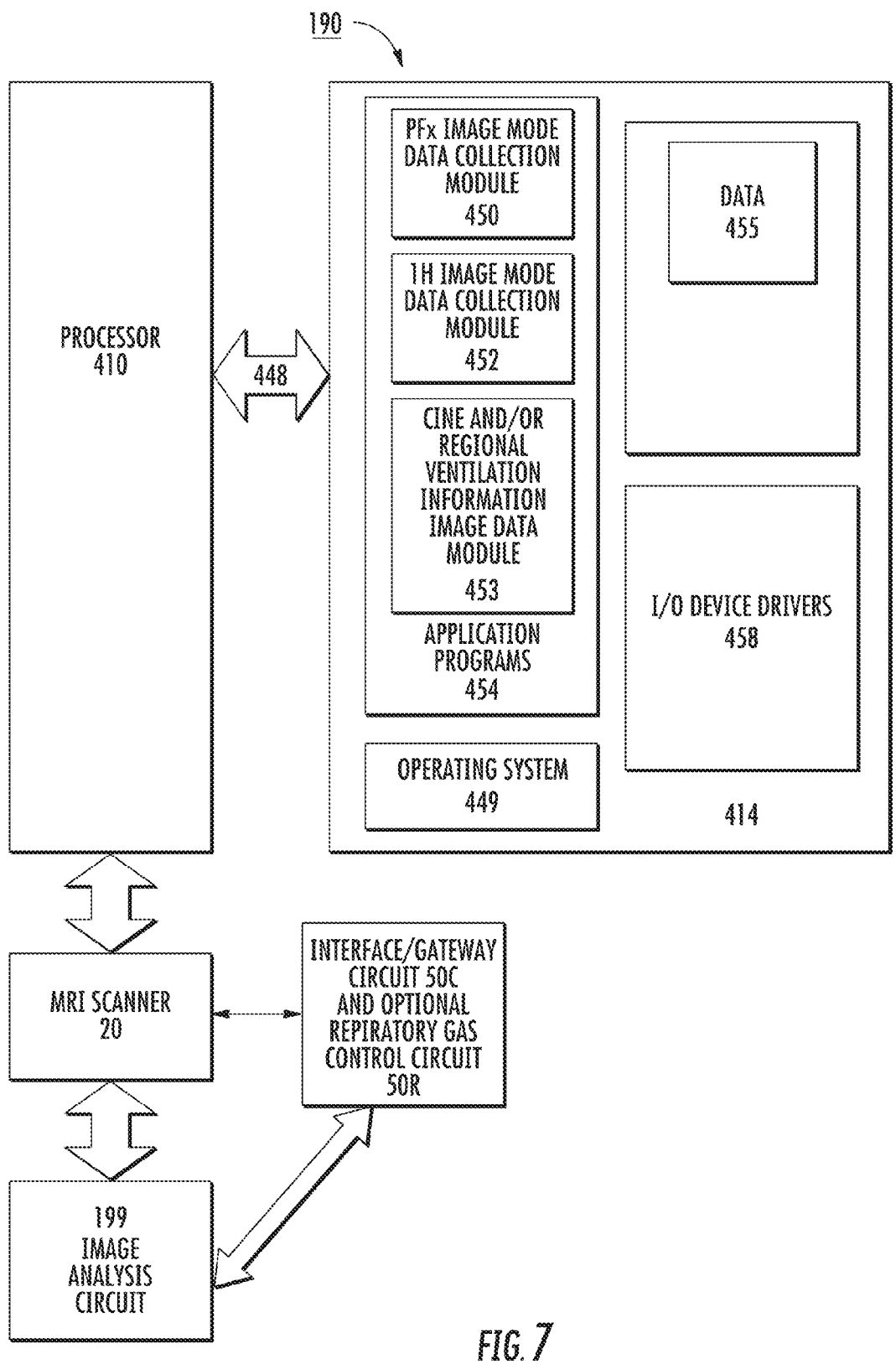
FIG. 7 is a schematic illustration of a data processing system that can be used to carry out embodiments of the present invention.

FIG. 7 is a schematic illustration of a circuit or data processing system 190 that can be used with the system 10. The circuits and/or data processing systems 190 data processing systems may be incorporated in a digital signal processor in any suitable device or devices. As shown in FIG. 7, the processor 410 communicates with an MRI scanner 20 and with memory 414 via an address/data bus 448. The processor 410 can be any commercially available or custom microprocessor. The MRI Scanner 20 and/or processor 410 can communicate with an image analysis circuit 199 and/or respiratory gating interface circuit 50C. The memory 414 is representative of the overall hierarchy of memory devices containing the software and data used to implement the functionality of the data processing system. The memory 414 can include, but is not limited to, the following types of devices: cache, ROM, PROM, EPROM, EEPROM, flash memory, SRAM, and DRAM.

FIG. 7 illustrates that the memory 414 may include several categories of software and data used in the data processing system: the operating system 449; the application programs 454; the input/output (I/O) device drivers 458; and data 455. The data 455 can include patient-specific image data. FIG. 7 also illustrates the application programs 454 can include a PFx Image Mode Data Collection Module 450, a 1H Image Mode Data Collection Module 452, and a Cine and/or Regional Ventilation Information Image Data or Analysis Module 453.

As will be appreciated by those of skill in the art, the operating systems 449 may be any operating system suitable for use with a data processing system, such as OS/2, AIX, DOS, OS/390 or System 390 from International Business Machines Corporation, Armonk, N.Y., Windows CE, Windows NT, Windows95, Windows98, Windows2000, WindowsXP or other Windows versions from Microsoft Corporation, Redmond, Wash., Unix or Linux or FreeBSO, Palm OS from Palm, Inc., Mac OS from Apple Computer, LabView, or proprietary operating systems. The I/O device drivers 458 typically include software routines accessed through the operating system 449 by the application programs 454 to communicate with devices such as I/O data port(s), data storage 455 and certain memory 414 components. The application programs 454 are illustrative of the programs that implement the various features of the data processing system and can include at least one application, which supports operations according to embodiments of the present invention. Finally, the data 455 represents the static and dynamic data used by the application programs 454, the operating system 449, the I/O device drivers 458, and other software programs that may reside in the memory 414.

While the present invention is illustrated, for example, with reference to the Modules 450, 452, 453 being application programs in FIG. 7, as will be appreciated by those of skill in the art, other configurations may also be utilized while still benefiting from the teachings of the present invention. For example, the Modules 450, 452, 453 and/or may also be incorporated into the operating system 449, the I/O device drivers 458 or other such logical division of the data processing system. Thus, the present invention should not be construed as limited to the configuration of FIG. 7 which is intended to encompass any configuration capable of carrying out the operations described herein. Further, one or more of modules, i.e., Modules 450, 452, 453 can communicate with or be incorporated totally or partially in other components, such as an MRI scanner 20, interface/gateway 50, image analysis circuit 199 and/or workstation 60.

The I/O data port can be used to transfer information between the data processing system, the workstation, the MRI scanner, the interface/gateway 50, the image analysis circuit 199 and/or another computer system or a network (e.g., the Internet) or to other devices or circuits controlled by the processor. These components may be conventional components such as those used in many conventional data processing systems, which may be configured in accordance with the present invention to operate as described herein.

The $^{19}F$ image data can be used to evaluate or assess pulmonary physiology and/or function. The image data can assess injury associated with and/or arising from disease states or conditions and other sources such as, for example, drugs used to treat cancer or other conditions, as well as chemical exposure (such as ingestion/inhalation of a poison or gas), environmental exposure, insect bites, snake venom, animal bites, viral, staff, or bacterial infections, as well as pulmonary status due to other disease states, infectious or otherwise, aging, trauma, and the like.

Embodiments of the invention can generate image data to assess, evaluate, diagnose, or monitor one or more of: a potential bioreaction to a transplant, such as lung transplant rejection, environmental lung disorders, pneumonitis/fibrosis, pulmonary hypertension, pulmonary inflammation such as interstitial and/or alveolar inflammation, interstitial lung diseases or disorders, pulmonary and/or alveolar edema, with or without alveolar hemorrhage, pulmonary emboli, drug-induced pulmonary disorders, diffuse lung disorders, chronic obstructive pulmonary disease, emphysema, asthma, pneumoconiosis, tuberculosis, pleural thickening, cystic fibrosis, pneumothorax, non-cardiogenic pulmonary edema, angioneurotic edema, angioedema, type I alveolar epithelial cell necrosis, hyaline membrane formation, diffuse alveolar damage such as proliferation of atypical type II pneumocytes, interstitial fibrosis, interstitial and/or alveolar infiltrates, alveolar septal edema, chronic pneumonitis/fibrosis, bronchospasm, bronchialitis obliterans, alveolar hemorrhage, aspiration pneumonia, hyercapnic respiratory failure, alveolitis/fibrosis syndrome, systemic lupus erythematosus, chronic eosinophilic pneumonia, acute respiratory distress syndrome, and the like.

The lung can be a target of drug toxicity which can be evaluated by embodiments of the present invention. It is known for example, that many medications, including chemotherapeutic drugs, anti-inflammatory drugs, anti-microbial agents, cardiac drugs and anticonvulsants can cause lung injury including lung toxicity that can be progressive and result in respiratory failure. See Diffuse Lung Disorders:

A Comprehensive Clinical-Radiological Overview, Ch. 19, Drug-Induced Pulmonary Disorders, (Springer-Verlag London Ltd, 1999), the contents of which are hereby incorporated by reference as if recited in full herein. Examples of drug-induced lung disorders that may be able to be evaluated according to embodiments of the present invention include, but are not limited to: pneumonitis/fibrosis, interstitial lung disease, interstitial or pulmonary honeycombing and/or fibrosis, hypersensitivity lung disease, non-cardiogenic pulmonary edema, systemic lupus erythematosus, bronchiolitis obliterans, pulmonary-renal syndrome, bronchospasm, alveolar hypoventilation, cancer chemotherapy-induced lung disease, pulmonary nodules, acute chest pain syndrome, pulmonary infiltrates, pleural effusion and interstitial infiltrates, angioedema, cellular atypia, diffuse reticular or reticulonodular infiltrates, bilateral interstitial infiltrates, reduced diffusing capacity, parenchymal damage with alveolar epithelial hyperplasia and fibrosis and/or atypia, early onset pulmonary fibrosis, late-onset pulmonary fibrosis, subacute interstitial lung disease.

Some of the above-conditions have been known to occur with specific drugs, such as mitomycin and bleomycin, and, in certain embodiments of the invention, the PFX gas mixtures can be used to evaluate a patient that is being treated with the potentially problematic drug to allow earlier intervention or alternate treatments should a lung exhibit a drug-induced disorder.

In some situations, patients can experience the onset of lung injury at the early onset of treatment with a therapeutic agent or in a certain environment. However, presentation of the injury can be delayed. In certain situations, the symptoms can present acutely with rapid deterioration. In either case, earlier identification of the problem can allow earlier intervention.

Non-Limiting Examples will be discussed below.

EXAMPLE 1

Breath-Hold Imaging

Figure 8:
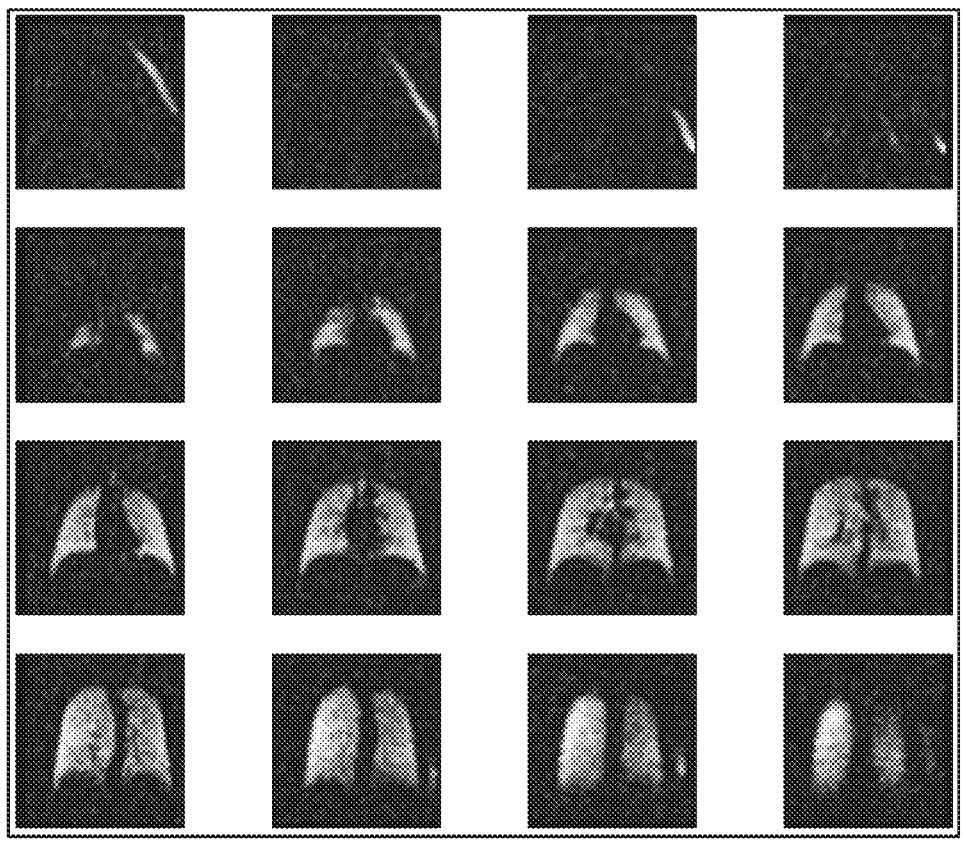
FIG. 8 is a reproduction of in vivo images 3D GRE (Gradient refocused echo) VIBE (Volumetric Interpolated Breath-hold Examination) of PFP of a pair of human lungs using a perfluorinated gas and oxygen gas mixture in a single breath hold.
Figure 9:
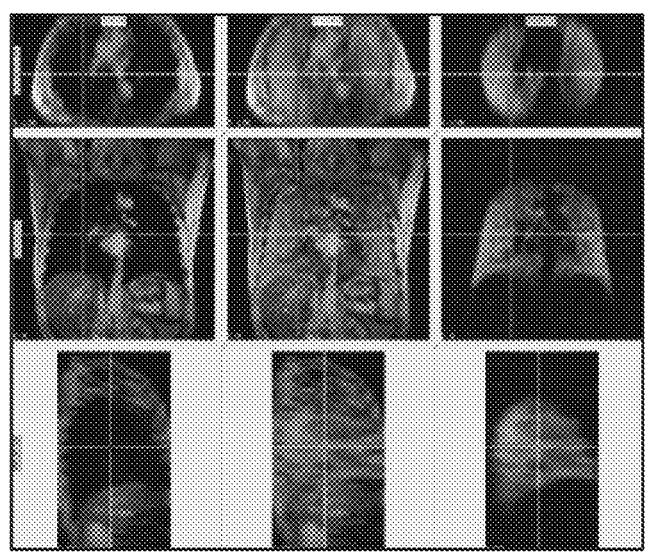
FIG. 9 is a panel of images of a patient's lung. The left images are $^1$H (base) images, the right images are PFx (match) images and the center images are 3D fusion images of $^1$H and PFx (typically shown color-coded). The top row of images corresponds to transverse slices, the center row of images corresponds to coronal slices and the bottom row of images corresponds to sagittal slices.

FIGS. 8 and 9 illustrate 3D in-vivo human lung images of a healthy 60 year old male obtained using MRI of a PFx/oxygen mixture. It is believed that this imaging methodology has the potential to be a 'game-changing' approach to evaluation and understanding of regional human lung ventilation as well as in the efficacy evaluation of pharmaceuticals involved in the treatment of lung disease. FIG. 8 is a panel of images obtained using a single breath hold of PFP. FIG. 8 shows 3D slice partitions of the $^{19}$F PFx images (scan time 15 seconds). Note the signal in the gas mixture delivery tube in the top frames of FIG. 8. It is contemplated that this signal data can be used as an external calibration standard for PFx signal.

FIG. 9 is a panel of three sets of images with the center set being a 3D fusion of $^1$H images (which are shown on the far left set of images as "base" images) co-registered with the PFx images (shown as the set on images on the far right). The left panel are $^1$H (base) images, the right images are PFx (match) images and the center images are 3D fusion images of $^1$H and PFx (typically shown color-coded). The top row of images corresponds to transverse slices. The center row of images corresponds to coronal slices and the bottom row of images corresponds to sagittal slices. The images shown in FIGS. 8 and 9 are 3D breath-hold images using PFP. The registered $^1$H images shown in FIG. 9 were obtained with the body coil concurrently with $^{19}$F signal obtained with the lung coil while the lung coil was actively proton blocked.

The PFP images were obtained using a 3D Gradient Refocused Echo (GRE) VIBE technique with a TR of 15 ms, a TE of 1.2 ms (non-selective excitation), pixel bandwidth of 200 Hz, 64×64 pts, FOV=35 cm and coronal slice thickness of 15 mm in a single 15 second breath hold. Voxel volume was 0.78 cm$^3$ with a nominal SNR of 15:1. One feature of imaging such agents is the lack of extraneous background signal allowing the use of non-selective excitation. Subjects were monitored for oxygen saturation continuously during the procedure with a fingertip pulse oximeter (In Vivo MVS 3155).

Conventional 15 second breath hold studies typically exhibit a small drop in oxygen saturation by pulse oximetry (SaO2). A similar drop of about 1-2% was observed during breath-hold imaging while breathing the PFx/O2 mixtures. It is believed that with agents like PFP with longer T1's (and longer T2*), very fast imaging may benefit from flip angle optimization (e.g., at a TR of about 5 ms, the optimum flip angle may be about 40 degrees).

NEX (number of excitations) can be balanced against pixel bandwidth to optimize SNR for different breathing patterns, free breathing and/or short versus long breath-holds, FEV type manuvers, etc.

It is contemplated that, due to the optimum relaxation conditions resulting from dominance of spin rotation relaxation on the PFx gas agents and the ability to get a signal from the incoming gas delivery system, embodiments of the present invention can allow a more quantitative analysis and display of lung ventilation.

EXAMPLE 2

MRI Cine Images of Lung Function

Cine images of breathing lungs can be generated as a "movie of breathing" that shows lung air spaces as they fill and evacuate during a respiratory cycle (including inhalation to exhalation) or during a FEV1 maneuver to visualize or show where the gas goes or stays and/or ventilation defects. The image data can be obtained over a plurality of respiratory cycles and the corresponding images (e.g., image slices) can be co-registered illustrating anatomy changes and ventilation data during the respiratory cycle.

The cine images can be gated cine images. That is, the respiratory waveform can be monitored and the image data registered (gated) to the part of the cycle during which it was obtained. A typical respiratory cycle (inhale to exhale) is about 2-5 seconds long. Several images can be taken, each in less than one second, and temporally registered or matched to the associated part of the respiratory cycle. The image data can be obtained over time and used to fill in the k-space (synchronized to the respiratory cycle). The signal data can be averaged to improve SNR or track ventilation information over the respiratory cycle.

In this context, 'gating' is taken to mean any of a variety of strategies to detect and follow the respiratory cycle. One example would be any of several types of respiratory bellows affixed about the chest and/or abdomen of the subject and further communicating with some form of pressure or motion transducer that allows the respiratory cycle to be monitored by the MRI system so that image acquisition can be synchronized with the respiration of the subject. In another embodiment the respiratory cycle may be monitored with optical or other means to detect chest wall or abdomen motion. In another embodiment so called 'navigator' signals from the MRI data may be used to track the respiratory cycle. In all cases such signals would interface to the MRI system for synchronization of the MRI acquisition to the respiratory cycle of the subject. This synchronization can take the form of acquiring a complete MRI acquisition in a portion of the respiratory cycle and/or segmenting the MRI acquisition over segments of the respiratory cycle and 'recombining' them during the reconstruction of the MRI images. One embodiment of this last approach is the basis for 'cine' type imaging.

EXAMPLE 3

Free-Breathing Scans $^{19}$F gas (and $^1$H) images of the human lung and airways can be obtained in free-breathing delivery to extract regional lung ventilation information. This imaging may be carried out so that the ventilation defects are shown or identified in near real-time. Particular disease states may make one of the PFx agents preferable over another such as where breathing cycle time for respiratory/gated imaging may be disease dependent.

The PFx gas agents will allow very rapid imaging with the possibility of near real time imaging of ventilation dynamics.

The image signal acquisition can be carried out to provide gated/cine images with free breathing strategies. Other cycle-based image generation techniques can also be used, such as, for example, spiral and propeller with passive "free-breathing" delivery of the PFx/O2 gas mixtures and room air to provide dynamic visualizations or cines of lung motion (which can include ventilation information/data for both inhale and exhale portions of the breathing cycle).

EXAMPLE 4

Global and Regional Ventilation Evaluation by $^{19}$F and $^1$H MRI

It is contemplated that a global and/or regional evaluation can be carried out in several manners including a spatial image analysis and/or in a histogram (local or global). The imaging session can be described as having "early phase", "equilibrium phase", "room air" phase and, where used, an "FEV1" maneuver phase.

The "early phase" is associated to the first few breaths or during a temporally early part of a "breath-hold" signal acquisition during (for the free breathing) or after (for the breath hold) delivery of the PFx/O2 gas mixture. The "equilibrium phase" is after the early phase. The FEV1 maneuver can be carried out while the patient is in a supine position on the scanner bed. The signal acquisition can be during the maneuver or at the end of a forced expiratory maneuver. The "room air" phase is associated to the period after the patient intakes room air rather than the PFx gas mixture. The signal acquisition typically occurs for several breathing cycles until $^{19}$F signal is no longer detectable.

Global ventilation defects can be identified by the overall sum of ventilation defects for both lungs during one or more of each of the different phases. In this embodiment, the total signal distribution in the segmented lung can be evaluated by histogram or 'tiles' evaluation for multimodal distribution. Regional ventilation can be evaluated using segmentation of the lung and by partition (reconstructed slice). Equilibrium image data and/or images can be compared to corresponding early-phase and/or room-air image data and/or images for regional ventilation evaluation. A ventilation defect can be identified in the signal data by a different pixel/voxel value relative to neighboring pixel/voxel values and/or changes in pixel/voxel intensity in subsequent image 'frames'.

Data from the room air phase can be used to evaluate gas-trapping in a regional as well as a temporal manner. Slope analysis or other mathematical interrogation can be used to identify the location and volume of the gas-trapping regions.

Figure 10:
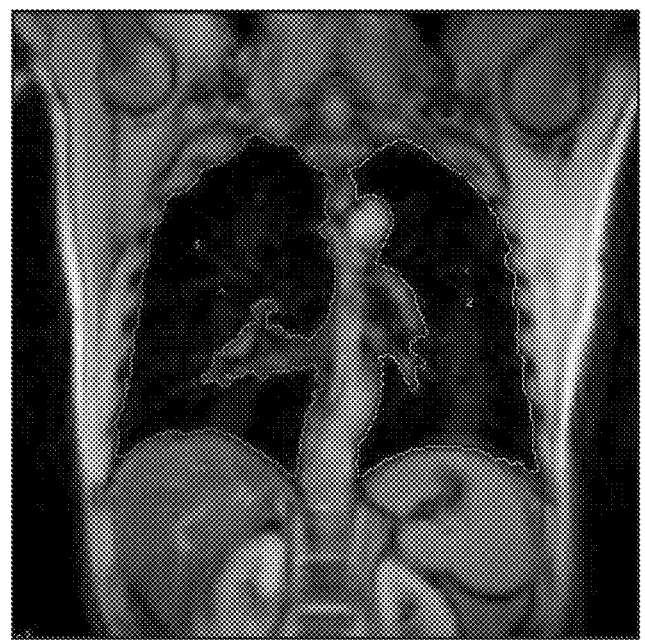
FIG. 10 is a image of the lungs showing regional lung morphometric information using 1H image data to demonstrate coverage of the lungs according to embodiments of the present invention.
Figure 11:
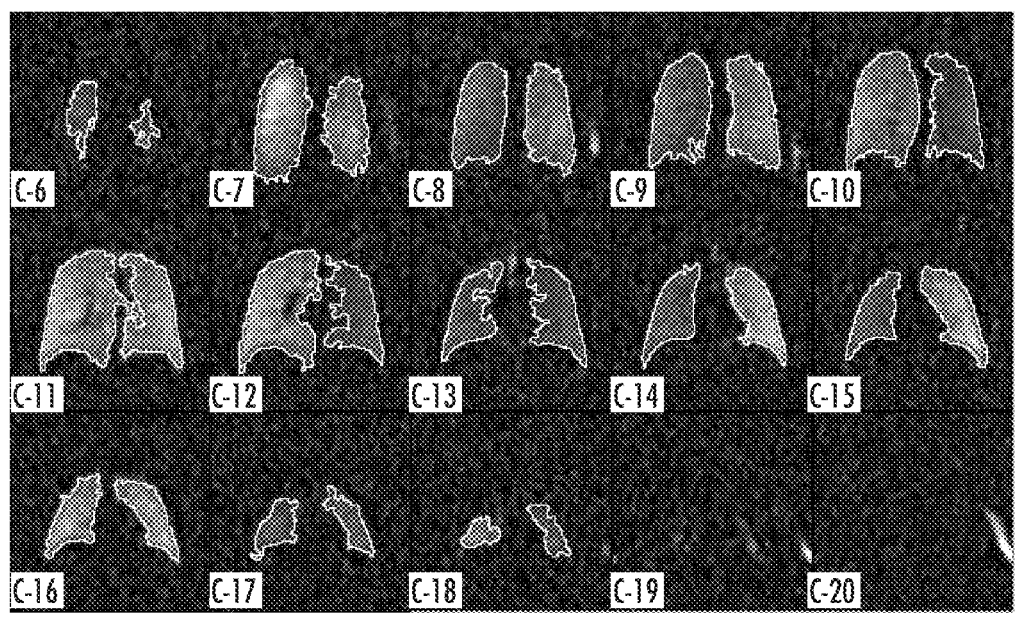
FIG. 11 is a visualization of a series of lung images obtained using PFx gas mixtures showing regional data of lung ventilation and/or function (e.g. ventilation defects, deficiencies, gas trapping and the like) (shown in panels C-6 through C-20) using PFx and oxygen gas mixtures according to embodiments of the present invention.

FIGS. 10 and 11 illustrate images that can indicate ventilation defects (and/or gas trapping) as well as other information regarding regional lung function. The PFx gas image data can be presented so that it is shown in one color and the anatomical structure can be shown in another (or several others). FIG. 10 illustrates an example of a hydrogen (1H) image that provides a morphologic/morphmetric framework for functional evaluation. FIG. 11 illustrates a series of color-coded PFx images during a breathing cycle as the PFx gas is taken in and exhaled from the lungs. These segmented images allow the calculation of ventilation defects and with temporal data, gas trapping. Again, because of the relaxation characteristics, it should be feasible to generate quantitative images of ventilation dynamics, ventilation defects and "gas trapping" in a matter of a few minutes of scanning with several liters of the gases. It is noteworthy that the medical grades of these gases in such mixtures with oxygen are currently in the price range of between about 7-15 dollars per liter. Thus, even multi-liter quantities for use as imaging contrast agents are not prohibitively expensive.

Airway spaces (e.g., alveolar spaces) can be imaged and biomarkers associated with different disease states, conditions or physiologies can be identified. Drug efficacy for treating different conditions may also be evaluated (for acute or chronic effect).

EXAMPLE 5

Gas Trapping and Histogram Analysis

From a ventilation information viewpoint, it should be easier to get at a more direct method of measuring gas trapping and should allow a temporal domain analysis of gas trapping not easily obtained with current imaging strategies.

Gas trapping should be readily and quantitatively evaluated by cycling between the inert PFx/O2 gas/oxygen mixture and room air (see, e.g., the discussion with respect to FIG. 4B above).

It is contemplated that, because one can cycle between the administration of PFx gas and room air, the loss of PFx signal over time can be monitored as a measure of "gas trapping." Unlike some perfluorinated compounds that have sensitivity to dissolved oxygen and have been used as an oxygen probe, both SF6 and PFP have a dominant spin rotation relaxation mechanism and are essentially insensitive to the paramagnetic effect of molecular oxygen (triplet ground state). This allows spin density imaging that is proportional to the amount of PFx. This action can be used for ventilation evaluation as discussed above and for the evaluation of gas trapping. This approach should allow evaluation of both the volume of gas trapping as well as the time course of the gas trapping. This latter temporal measure may provide a new dimension for the evaluation of gas trapping that is not currently available, even with high resolution CT (HRCT).

Figures 12A, 12B:
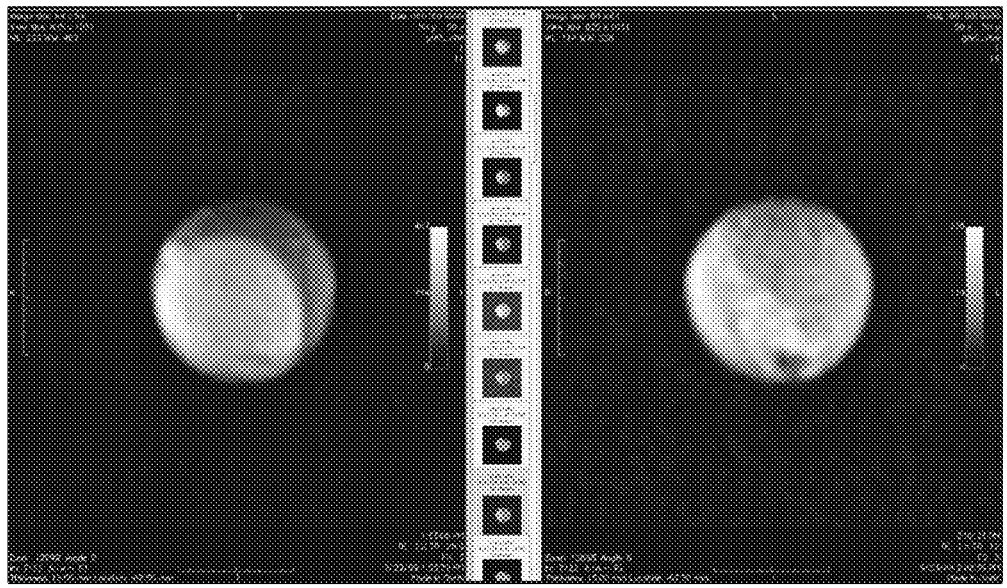
FIGS. 12A and 12B are examples of time-series images of a "leaking glove" phantom housed in an acrylic sphere which allowed PFx to leak into the sphere via a small hole in the glove. The images illustrate data analyzed spatially to show contrast between different concentrations of PFx analogous to 'gas trapping' according to embodiments of the present invention.

FIGS. 12A and 12B illustrate a "leaking glove" phantom which represents an example of temporal evaluation. In this example, a latex glove was inflated in an acrylic sphere with a small hole in the glove, allowing the glove to leak PFx into the sphere. FIGS. 12A and 12B (two exemplary time-separated images) shows contrast between two concentrations of PFx in the sphere. Note the increase in the signal intensity as the gas leaks from the glove into the acrylic sphere (this is analogous to what would be seen with gas trapping after changing to room air).

Figures 13A, 13B:
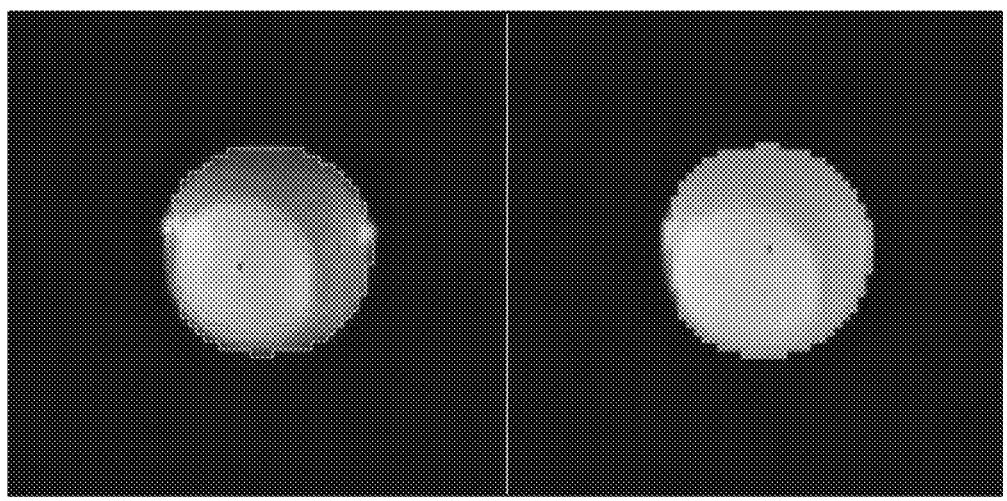
FIGS. 13A and 13B illustrate two ROIs (Region of Interests) using the leaking glove phantom.

FIGS. 13A and 13B illustrate two ROIs based on intensity from one frame of the 'leaking glove' phantom. The first ROI (Region 1, brighter ROI) is primarily on the interior of the object with a lighter shade than Region 2. The second ROI (Region 2) is primarily on the perimeter surrounding the Region 1 ROI and has a darker shade. The data can be analyzed spatially as shown in FIGS. 13A and 13B, such as with region growing. FIG. 13A shows two regions of interest 'grown' using a seeded approach while 13B shows a region of the entire 'object'.

Figure 14:
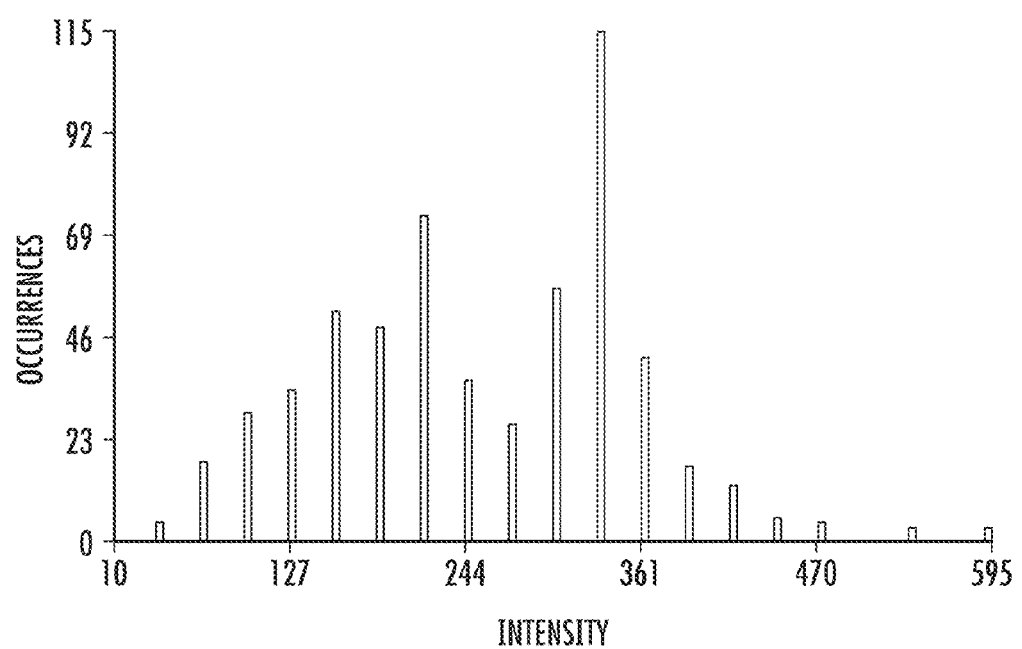
FIG. 14 is a graph of occurrences versus intensities of pixels/voxels of the object illustrating that the intensity data/concentration differences can be analyzed numerically according to embodiments of the present invention. This shows a 'modal' distribution of intensities analogous to gas trapping.

Alternatively, as shown in FIG. 14, the intensities of the object can be sampled (occurrences versus intensity). FIG. 14 is a vigintile plot of the intensities extracted from the whole object, clearly demonstrating two intensity distributions. Table 1 below illustrates the mean and SD intensity and volume of the two ROIs in the left image and for the whole object.

TABLE 1

Signal and Volume Data of Glove in Sphere Phantom

| Region | Signal Mean | Signal SD | Volume (cc) |
|---|---|---|---|
| Region A ROI on left image (FIG. 12A) | 353 | 38 | 159 |
| Region B ROI on left image (FIG. 12A) | 184 | 61 | 185 |
| Whole Object right image (FIG. 12B) | 262 | 98 | 344 |

The image data can be obtained over a plurality of breathing or respiratory cycles and the corresponding images (e.g., image slices) can be co-registered.

Ventilation defects may also be identified by evaluating co-registered images of pixels/voxels using a linear function. If the slope of the intensity of co-registered pixels/voxels in a ROI is substantially zero, then there is no change in intensity and a gas trap may be identified. Alternatively, if the slope is negative, then the region likely does not have a gas trap.

EXAMPLE 6

Spirometer Values Correlated with Regional Image Ventilation Data

Spirometric data can be collected in the supine position as MRI is carried out while the patient is in this position, as supine position will change resting functional residual capacity volume and likely influence FEV1/FVC. The spirometer measurements can be made in the MRI suite just before the MRI session using an MRI compatible portable spirometry system. The density of MRI gas mixtures will differ from the air density in the room. Spirometry can be carried out on a patient with both room air and the gas mixture (at least until an effect adjustment factor can be determined).

EXAMPLE 7

Clinical Trials

The question of regional ventilation in disorders such as COPD and other lung pathologies or status, such as cystic fibrosis and lung transplants, is becoming increasingly important. A recent editorial in the New England Journal of Medicine addressed the issue of using changes in FEV1 (Forced Expiratory Volume in 1 second) as an endpoint in treatment trials (Reilly 2008). The comments were related to the UPLIFT (Understanding Potential Long-Term Impacts on Function with Tiotropium) trial (tiotropium vs. placebo) [NCT00144339] (Tashkin, Celli et al. 2008). In this study, reported in the same issue, patients using standard respiratory medications (except inhaled anticholinergic drugs) were randomized to their existing treatment with either tiotropium or placebo and followed for a 4-year period. While the treatment group using tiotropium had improvements in lung function, QOL (quality of life) and fewer exacerbations in the 4-year study; there was no significant change in the rate of decline in FEV1 either before of after bronchodilation. In a separate study called TORCH (Towards a Revolution in COPD Health), trial patients were randomized to a combination treatment (fluticasone and salmeterol), each of the agents alone or placebo [NCT00268216] (Calverley, Anderson et al. 2007). TORCH patients were followed for a 3-year period where the primary outcome was death from any cause. The reduction in mortality did not reach statistical validity although there were benefits in secondary outcomes (e.g. frequency of exacerbations, spirometric values). The difference in FEV1 for the dual agent arm versus placebo was 0.092 liters (95% CI 0.075-0.108, p<0.001), although the mean baseline FEV1 for the treated and placebo group was 1.24 and 1.26 liters respectively, yielding a 7% difference in the FEV1, a difference not generally considered clinically relevant. The dominant question in the editorial and one facing studies of COPD is the heterogeneity of the disorder and the current lack of a good diagnostic tool for stratification/screening of potential subjects for a treatment study.

The image data provided by embodiments of the invention can be particularly suitable for diagnosing lung diseases or conditions in patients, monitoring animals in drug discovery programs, monitoring patients in and screening participants for clinical trials and assessing therapeutic efficacy of therapeutic treatments on lung physiology/conditions and diseases.

EXAMPLE 8

Assessing Regional Failure

In lung transplantation, evidence of regional failure is typically followed with bronchoscopy under sedation to evaluate pending failure of the transplant. In cystic fibrosis, a similar tactic exists for evaluation of the child's lungs using bronchoscopy under sedation. Embodiments of the invention can provide an alternative relatively simple, non-invasive measure of ventilation using MRI image data.

EXAMPLE 9

Histograms

Ventilation defects can be identified using at least one histogram of mean intensity voxels from MRI data of the perfluorinated gas. The histogram can represent a percentage versus mean intensity of voxels within a region of interest or identify clusters of voxels/pixels of similar intensity and/or those that have a statistically significant variance from "normal" intensity voxels/pixels.

The characteristic of the pixels/voxels that is evaluated via one or more histograms may include intensity, color, saturation and/or other characteristics of individual pixels/voxels as well as relative characteristics of multiple pixels/voxels, such as contrast ratios or the like. The evaluation can be carried out electronically and the results of the evaluation can be provided to a user or may be provided for further analysis. For example, a comparison of a first (baseline) image and a second image may be performed and a difference in average intensity may be provided as results to a user. Furthermore, a histogram of the characteristic and/or differences in the characteristic between the baseline and comparison images may be determined and provided as a result. Additionally, the histogram could be pattern matched to a library of histogram profiles that are characteristic of particular injuries, diseases and/or conditions. The results of the determination may, for example, be provided as part of a graphic user interface.

EXAMPLE 10

Identifying Biomarkers for Disease States

The image data provided by embodiments of the invention can be particularly suitable for identifying genotypes of a lung disease, such as COPD, or assessing whether the patient has large and/or small airway disease.

EXAMPLE 11

Lung Ventilation Defect Indexes

Lung specific or further detailed regional measures of ventilation defects (and severity) can be generated using a lung ventilation index, e.g., R-5, L10. A standardized compartmental model of the lungs can be used to define multiple indexes in defined locations of each lung representing degrees or measures of ventilation defects.

EXAMPLE 12

Display with Multiple MRI Lung Images and Flow Data Output

A workstation can have a display that can concurrently show multiple MRI lung images including "breath hold" inspire and expire images of room air and/or PFx gas, cine free breathing PFx gas F19 images and wash-in and/or wash-out PFx F19 images. The display can show the images in a timeline corresponding to a graph or output of pneumotachomoeter data.

EXAMPLE 13

Ventilation Defect Severity Analysis Using Wash-in and/or Wash-Out Parameters

Figure 23:
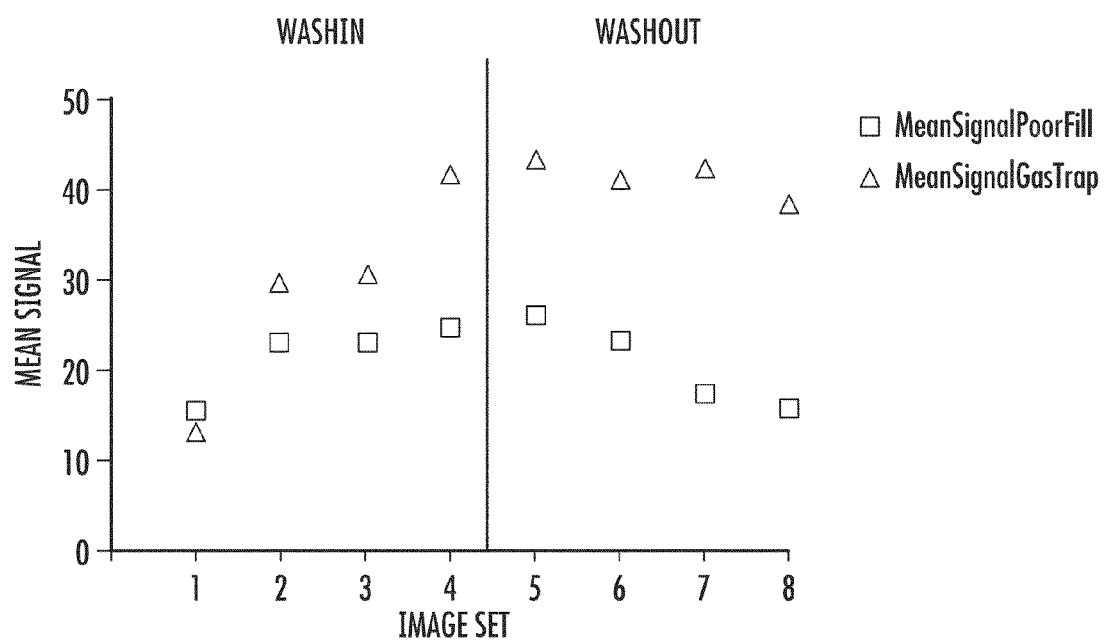
FIG. 23 is an example of a graph, mean signal over time (based on a series of images) of wash-in and wash out from a region of interest associated with images shown in FIG. 22.

FIG. 22 shows an array of images obtained during sequential breath holds while breathing the PFx mixtures to 'equilibrium'. Frames 1-5 are wash-in and frames 6-8 are wash-out after switching to room air. Note that the kinetics of wash-in and wash-out do not have to be equivalent. FIG. 23 shows an example of a 'wash-in'/out plot from a region of interest analysis of FIG. 22 that can indicate an intake defect (during wash in and/or at equilibrium) and/or gas trapping (during wash out) and the like.

The present invention finds use for both veterinary and medical applications as well as animal studies for drug discovery and the like. The present invention may be advantageously employed for diagnostic evaluation and/or treatment of subjects, in particular human subjects, because it may be safer (e.g., less toxic) than other methods known in the art (e.g., radioactive methods). In general, the inventive methods may be more readily accepted because they can avoid radioactivity or toxic levels of chemicals or other agents. Subjects according to the present invention can be any animal subject, and are preferably mammalian subjects (e.g., humans, canines, felines, bovines, caprines, ovines, equines, rodents, porcines, and/or lagomorphs), and more preferably are human subjects.

It is contemplated that embodiments of the present invention can be used to identify ventilation defect volume and location(s), ventilation defect severity, wash-in, wash-out, and/or ventilation dynamics which may be correlated to 1H data.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. In the claims, means-plus-function clauses are intended to cover the structures described herein as performing the recited function and not only structural equivalents but also equivalent structures. Therefore, it is to be understood that the foregoing is illustrative of the present invention and is not to be construed as limited to the specific embodiments disclosed, and that modifications to the disclosed embodiments, as well as other embodiments, are intended to be included within the scope of the appended claims. The invention is defined by the following claims, with equivalents of the claims to be included therein.

That which is claimed is:

1. A method of generating lung ventilation information of a subject, comprising:

providing a pressurized canister of a medical grade gas mixture of perfluorinated gas and oxygen holding the medical grade mixture in a gaseous phase;

electronically obtaining a series of $^{19}$F magnetic resonance imaging (MRI) images of lungs of a subject associated with an inhaled amount of the perfluorinated gas and oxygen mixture from the pressurized canister during wash in and wash out of the perfluorinated gas and oxygen mixture;

electronically obtaining $^1$H MRI images of the lungs of the subject before or after or before and after obtaining the series of $^{19}$F MRI images while the subject breathes room air;

electronically registering the obtained $^{19}$F MRI lung images to the obtained $^1$H MRI lung images of the subject;

electronically applying lung masks to the registered $^{19}$F images to define a perimeter of a lung cavity of a respective lung; and then electronically evaluating summary parameters of different volumes of the registered $^{19}$F lung images after applying the lung masks to generate lung ventilation information that identifies regional lung ventilation defects including gas trapping, wherein the obtaining, registering, applying and evaluating steps are carried out using at least one processor.

2. The method of claim 1, wherein the electronically evaluating the summary parameters evaluates 2D shape factors of the different volumes.

3. The method of claim 1, further comprising displaying a series of color-coded static lung images showing regional ventilation information over at least a portion of at least one respiratory cycle based at least in part on the evaluated summary parameters.

4. The method of claim 1, further comprising displaying lung ventilation information on a color-coded lung map of ventilation and/or perfusion with at least one of abnormalities, defects and deficiencies shown with at least one of a defined color(s), intensity or opacity based on the summary parameters to thereby make the at least one of the abnormalities, defects and deficiencies visually dominant.

5. The method of claim 1, further comprising electronically displaying a graph of $^{19}$F pixel intensity versus pixel count for each lung based on the pixels in the different volumes and different slices.

6. The method of claim 1, further comprising generating histograms of mean intensity of voxels within regions of interest to identify clusters of voxels or those that have a statistically significant variance from normal intensity voxels.

7. The method of claim 1, wherein the electronically evaluating comprises electronically generating data tables of pixel parameters for the different volumes with the tables comprising pixel centroids for respective slices in the different volumes.

8. The method of claim 1, further comprising electronically providing a visual output of a graphic analysis fit to a lung model of ventilation wash-in and wash-out using the obtained $^1$H and $^{19}$F MRI images and depicting functional information based on the summary parameters.

9. The method of claim 1, further comprising displaying a lung map as a rendered visualization of one or more selected summary parameters that shows at least one of ventilation and perfusion information in a manner that illustrates relative degrees or measures of function in at least one of different colors, opacities and intensities.

10. The method of claim 1, further comprising displaying three dimensional fusions of the obtained $^1$H and $^{19}$F MRI images, color-coded to show ventilation defects based on the summary parameters.

11. The method of claim 1, wherein the medical grade gas mixture is supplied at a pressure in the pressurized canister that is sufficiently low so that a dense gas component remains in a gaseous state under normal operating conditions of at least one of about 21 degrees C. or room temperature.

12. The method of claim 1, wherein the electronically evaluating the summary parameters evaluates a plurality of the following: pixel intensity, pixel count, histograms, summary statistics and 2-D shape factors.

13. The method of claim 1, wherein the electronically evaluating the summary parameters evaluates histograms of pixel intensity versus pixel count to identify ventilation defects.

14. The method of claim 1, further comprising quantitatively analyzing lung function and/or electronically assessing regional ventilation of the lungs and providing a visualization of a map of the lungs illustrating regional ventilation defects of the lungs.

15. The method of claim 1, further comprising quantitatively evaluating gas trapping by cycling between administration of the medical grade oxygen and gas mixture and administration of room air to the subject, wherein loss of $^{19}$F MRI signal over time associated with the different volumes and different slices during the cycling corresponds to a measure of gas trapping.

16. A method of obtaining lung information of a subject, comprising:
positioning a subject in a magnetic field associated with a high-field magnet of an MRI scanner;
cyclically delivering, in vivo, via inhalation, a medical grade gas mixture and room air to the subject while the subject is in the magnetic field of the MRI scanner, wherein the medical grade gas mixture comprises between 20-79% inert perfluorinated gas and at least 20.5% oxygen gas obtained from a pressurized canister of the medical grade gas mixture, wherein the medical grade gas mixture is supplied at low pressure in the pressurized canister so that a dense gas component remains in a gaseous state under normal operating conditions of about 21 degrees C. and/or room temperature;
electronically acquiring a series of $^{19}$F MRI lung space images associated with the inhalation of the cyclically delivered medical grade gas mixture and a series of $^1$H MRI lung images, wherein the series of $^{19}$F MRI lung space images includes images acquired while the subject breathes room air to obtain wash-out and/or gas trapping data associated with a depleneshing amount of the $^{19}$F MRI signal as the subject breathes room air, and wherein the series of $^1$H MRI lung images are acquired using the room air delivered to the subject before or after acquiring the series of $^{19}$F MRI lung space images or before and after acquiring the series of $^{19}$F MRI lung space images;
registering the acquired $^{19}$F MRI lung images to the acquired $^1$H MRI lung images of the subject;
applying lung masks to the registered $^{19}$FMRI images to define a perimeter of a lung cavity of a respective lung; and then
evaluating summary parameters by slice of a plurality of different volumes of the registered $^{19}$FMRI lung images after applying the lung masks to generate lung ventilation information that identifies regional lung ventilation defects including gas trapping,
wherein the acquiring, registering, applying and evaluating are carried out using at least one processor.

17. The method of claim 16, wherein the cyclical delivering is carried out so that a component ratio of the medical grade gas mixture that is drawn out of the pressurized canister remains constant, the method further comprising providing the pressurized canister with the medical grade gas mixture at the low pressure for the cyclical delivering with the medical grade gas mixture formulated to have a dew point of 0 degrees C. so that the medical grade gas mixture will not condense above this temperature.

18. The method of claim 16, wherein the evaluating the summary parameters evaluates a plurality of the following: pixel intensity, pixel count, histograms, summary statistics and 2-D shape factors.

19. The method of claim 18, further comprising electronically generating and displaying a visual output of a graphic analysis using the acquired $^{19}$F MRI images fit to a lung model of ventilation wash-in and wash-out depicting functional information of one or both lungs of the subject.

20. The method of claim 18, further comprising generating histograms of mean intensity of voxels within regions of interest to identify clusters of voxels that have a statistically significant variance from normal intensity voxels.

21. The method of claim 20, further comprising electronically evaluating the histograms to identify whether the subject is likely to have a ventilation and/or lung defect.

22. An MRI system, comprising:
an MRI scanner comprising a magnet with a magnetic field and at least one RF coil, the at least one RF coil being sized and configured to reside about lungs of a human patient; and
a gas delivery system comprising:
a pressurized canister of a medical grade gas mixture comprising perfluorinated gas in a level that is between 20-79% and oxygen gas in a level that is at least 20.5%, wherein the pressurized canister is at a sufficiently low pressure to hold the gas mixture in a gaseous state at room temperature;
a gas flow path in communication with the pressurized canister of the medical grade gas mixture comprising at least one conduit extending from the canister to a free-breathing dispensing member adapted to reside over, on or in a respective patient while the patient resides inside the magnetic field to deliver the medical grade gas mixture;
at least one oxygen sensor in communication with the gas flow path of the medical grade gas mixture; and
at least one processor in communication with and/or onboard the MRI scanner, wherein the at least one processor:

(i) obtains a series of $^{19}$F magnetic resonance imaging (MRI) images of lungs of the patient associated with the medical grade gas mixture during wash in and wash out of the perfluorinated gas and oxygen mixture;
(ii) obtains $^1$H MRI images of the lungs of the patient associated with room air inhaled by the patient before or after or before and after the series of $^{19}$F magnetic resonance imaging (MRI) images of lungs of the patient are obtained;
(iii) registers the obtained $^{19}$F MRI lung images to $^1$H MRI lung images of the patient;
(iv) applies lung masks to the registered $^{19}$F images to define a perimeter of a lung cavity of a respective lung; and then
(v) evaluates summary parameters from a plurality of slices of a plurality of different volumes of the registered $^{19}$F lung images after the lung masks are applied to generate lung ventilation information that identifies regional lung ventilation defects including gas trapping.

23. The system of claim 22, wherein the evaluated summary parameters comprise 2D shape factors of the slices of the different volumes.

24. The system of claim 22, wherein the at least one processor determines a time constant for the medical grade gas mixture to calibrate signal intensity based on a sample of an input of the delivered gas mixture and an exhaled sample of the delivered gas mixture to thereby define a global exchange of oxygen.

* * * * *

UNITED STATES PATENT AND TRADEMARK OFFICE
CERTIFICATE OF CORRECTION

PATENT NO. : 9,724,015 B2
APPLICATION NO. : 14/987356
DATED : August 8, 2017
INVENTOR(S) : Charles et al.

It is certified that error appears in the above-identified patent and that said Letters Patent is hereby corrected as shown below:

In the Specification

Column 23, Line 3: Please correct "a valve 30v" to read -- a valve $30v_1$ --

Column 29, Line 56: Please correct "Unix or Linux or Free BSO" to read -- Unix or Linux or Free BSD --

Signed and Sealed this
Fifth Day of June, 2018

Andrei Iancu
*Director of the United States Patent and Trademark Office*